US005895788A

United States Patent [19]
Wideman, Jr. et al.

[11] Patent Number: 5,895,788
[45] Date of Patent: Apr. 20, 1999

[54] USE OF L-ARGININE AND SALTS THEREOF IN DRINKING WATER FOR THE PREVENTION AND/OR TREATMENT OF PULMONARY HYPERTENSION SYNDROME IN AVIANS

[75] Inventors: Robert F. Wideman, Jr.; Walter G. Bottje, both of Fayetteville, Ark.; Michael T. Kidd, Chesterfield, Mo.

[73] Assignee: The Board of Trustees of the University of Arkansas, Little Rock, Ark.

[21] Appl. No.: 08/792,875

[22] Filed: Jan. 31, 1997

Related U.S. Application Data

[60] Provisional application No. 60/010,878, Jan. 31, 1996.
[51] Int. Cl.$^6$ .................................................. A61K 31/155
[52] U.S. Cl. ............................................................... 514/565
[58] Field of Search ............................................... 514/565

[56] References Cited

U.S. PATENT DOCUMENTS

| | | | |
|---|---|---|---|
| 5,158,883 | 10/1992 | Griffith | 435/240.2 |
| 5,213,815 | 5/1993 | O'Brien | 424/935 |
| 5,217,997 | 6/1993 | Levere et al. | 514/565 |

OTHER PUBLICATIONS

Wideman et al., Poultry Science, vol. 74, No. 2, pp. 323–330, 1995.

Taylor, et al "Dietary Arginine Influence Rous Sarcoma Growth in a Major Histocompatibility B Complex Progressor Genotype", *Society for Experimental Biology and Medicine*, 1992, pp. 38–41.

Subcommittee on Poultry Nutrition, Committee on Animal Nutrition, Board of Agriculture, "Nutrient Requirements of Poultry", *National Research Council*, 9$^{th}$ Ed., 1994, pp. 27–42.

Wideman Jr., et al. "Preventing Ascites with Pulmonary Vasodilators" Proceedings of the Meeting Arkansas Nutrition Conference, Sep. 13, 14, 15, 1994.

Owen, et. al. Effect of Age of Exposure and Dietary Acidification or Alkalization on Broiler Pulmonary Hypertension Syndrome, 1994, J. Appl. Poultry Res. 3:244–252.

*Primary Examiner*—Richard L. Raymond
*Attorney, Agent, or Firm*—J. M. (Mark) Gilbreth; Robert W. Strozier; Gilbreth & Strozier, P.C.

[57] ABSTRACT

A method of treating or preventing pulmonary hypertension syndrome in avians, generally including administering a drinking water containing L-arginine compound to the avian.

17 Claims, 66 Drawing Sheets

Chamber Assignments for Nutri-Quest Arginine Water Treatment Experiment

| 12F<br>Arg HCl<br>Level 1 | 12R<br>Tap Water |
|---|---|
| 11F<br>Arg Free Base<br>Level 1 | 11R<br>Tap Water |
| 10F<br>Arg HCl<br>Level 2 | 10R<br>Tap Water |
| 9F<br>Arg Free Base<br>Level 2 | 9R<br>Tap Water |
| 8F<br>Arg HCl<br>Level 3 | 8R<br>Tap Water |
| 7F<br>Arg Free Base<br>Level 3 | 7R<br>Tap Water |

Chamber 7 Door → (at 7F)

Chamber Divider (between 7F and 7R)

\* 100 chicks/chamber

F = Front

R = Rear

FIG. 1

BRONCHUS CLAMP BROILERS, CHAMBER 9

9F = Arginine Free Base at: 6.0 g/L (Days 1-14)
7.0 g/L (Days 15-28)
7.6 g/L (Days 29-49)
9R = Tap Water 11F = Arginine Free base at: 3.0 g/L (Days 1-14)
3.4 g/L (Days 15-28)
3.8 g/L (Days 29-49)
11R = Tap Water 12F = Arginine HCl at: 3.6 g/L (Days 1-14)
4.1 g/L (Days 15-28)
4.6 g/L (Days 29-49)
12R = Tap Water

FIG. 39

USE OF L-ARGININE AND SALTS THEREOF IN DRINKING WATER FOR THE PREVENTION AND/OR TREATMENT OF PULMONARY HYPERTENSION SYNDROME IN AVIANS

RELATED APPLICATION DATA

This application clamis priority from U.S. Provisional application Ser. No. 60/010,878 filed Jan. 31, 1996.

BACKGROUND OF THE INVENTION

1. Field of the Invention

The present invention relates to treatment of avians. In another aspect, the present invention relates to the use of L-arginine for the treatment of avians. In even another aspect, the present invention relates to the administration of L-arginine to avians through drinking water for the treatment of or prevention of pulmonary hypertension syndrome, also commonly known as ascites in poultry.

2. Description of the Related Art

Pulmonary hypertension syndrome was reported as early as 1968, and is a condition characterized by mortality with the accumulation of fluid (ascites fluid) in the abdomen of the bird. Ascites fluid accumulation in the body cavity may also be caused by tumor growth in the abdominal cavity. Pulmonary hypertension syndrome is caused by a high resistance to blood flow through the lungs. This excessive resistance of blood flow through the lungs causes an adverse effect on the heart, and hence pulmonary hypertension syndrome. As used hereinafter, "ascites" and "pulmonary hypertension syndrome" will be used interchangeably with the understanding that this form of ascites in poultry is in no way related to tumor growth.

Pulmonary hypertension syndrome poses a serious problem to young fast growing poultry all over the world. First associated with flocks raised at high altitude, it is now recognized that other factors, such as cold temperatures, rapid growth, respiratory distress, high salt intake, and poor ventilation, also encourage pulmonary hypertension syndrome. Death from pulmonary hypertension syndrome results due to an enlarged heart, specifically including dilation and hypertrophy of the right ventricle. Congestive heart failure develops leading to liver damage, and kidney lung and intestinal problems, and compression of the air sac with abdominal fluids. While traditionally, male birds were at greater risk than females because of their faster growth rate, the conditions of modern poultry farming have caused female birds to suffer almost equally.

Pulmonary hypertension syndrome was originally confined to countries such as Bolivia, Columbia, Mexico, Peru, and South Africa, where poultry are traditionally raised at high altitude. It has now been reported in virtually all countries with intensive poultry production practice using modern broiler strains.

The commercial impact of pulmonary hypertension syndrome can be devastating. In fact, mortality among some United States poultry flocks can commonly amount to 5% of birds "started", and in some cases can range to over 30% of birds started. This results in millions of dollars lost due to ascites.

It has been reported that there has been a marked increase in the incidence of pulmonary hypertension syndrome in low altitude countries such as the United Kingdom, Italy, Germany, Australia and Mauritius. It has also been reported that recent evidence tends to show that ascites is now increasing during warmer weather and is now appearing at a younger age in poultry.

U.S. Pat. No. 5,217,997, issued Jun. 8, 1993 to Levere et al. discloses the use of L-arginine or a pharmaceutically acceptable salt thereof in the treatment of hypertension, bronchial asthma, and high vascular disorders in mammals. Such high vascular resistance disorders in mammals include primary or secondary vasospasm, angina pectoris, cerebral ischemia and preeclampsia of pregnancy. As disclosed, about 1 mg to about 1500 mg per day of the L-arginine or a pharmaceutically acceptable salt thereof is administered to the mammal.

U.S. Pat. No. 5,158,883, issued Oct. 27, 1992 to Griffith, discloses a method of treating mammal cells using amino arginine to block nitric oxide formation in-vitro. Typical dosages are administered in a nitric oxide synthesis inhibiting amount, generally in the range of about 10 µg/kg to 100 mg/kg.

U.S. Pat. No. 5,213,815, issued May 25, 1983 to O'Brien, discloses a method of treating and preventing ascites in poultry by administering a combination of Eyebright herb and Brewer's yeast to poultry. Prevention of ascites is accomplished by adding Brewer's yeast to poultry food at a rate of about 40 grams per 160 pounds of poultry, starting from "day old" and continuing through the last day of "grow out". Treatment of ascites is accomplished by supplementing the Brewer's yeast with Eyebright herb at a rate of 500 mg per 160 pounds poultry per day for seven days.

"Dietary Arginine Influences Rous Sarcoma Growth in a Major Histocompatibility B Complex Progressor Genotype", Taylor et al., Society for Experimental Biology and Medicine, 1992, at 38–41, discloses administering five week-old chickens feed having either 0.92% or 2.40% L-arginine content to lower tumor growth. While the article reports lower tumor growth from feed high in L-arginine, it discloses that mortality was not significantly different between a low and high L-arginine diet. Additionally, this article is silent regarding treatment of chickens having pulmonary hypertension syndrome, is silent regarding administration of L-arginine prior to five weeks after hatching.

The "Nutrient Requirements of Poultry", by the Subcommittee on Poultry Nutrition, Committee on Animal Nutrition, Board of Agriculture, National Research Council, 9th Ed., 1994, at 27–42, recommends providing broilers with feed having 1 to 1.25 wt % arginine, turkeys with feed having 0.5 to 1.6 wt % arginine, and ducks feed having from 1 to 1.1 wt % arginine.

However, in spite of these advancements in the prior art, none of these prior art references disclose or suggest the administration of L-arginine to avians for the treatment and/or prevention of pulmonary hypertension syndrome.

Thus, there is still a need for a method of treating and/or preventing pulmonary hypertension syndrome in avians.

These and other needs in the art will become apparent to those of skill in the art upon review of this specification, including its drawings and claims.

SUMMARY OF THE INVENTION

It is an object of the present invention to provide for a method of treating avians.

It is another object of the present invention to provide for a method of administering L-arginine to avians.

It is even another object of the present invention to provide for a method of administering L-arginine to avians to treat and/or prevent pulmonary hypertension syndrome.

These and other objects of the present invention will become apparent to those of skill in the art upon review of this specification, including its drawings and claims.

According to an embodiment of the present invention there is provided a method of treating pulmonary hypertension syndrome in an avian. The method includes administering to the avian having pulmonary hypertension syndrome, drinking water comprising a sufficient amount of an L-arginine compound to treat pulmonary hypertension syndrome.

According to another embodiment of the present invention there is provided a method of treating pulmonary hypertension syndrome in a chicken. The method generally includes orally administering to the chicken having pulmonary hypertension syndrome a drinking water comprising a sufficient amount of an L-arginine compound to treat the pulmonary hypertension syndrome, wherein the administration of the L-arginine compound commences before the avian is five weeks old.

According to even another embodiment of the present invention there is provided a method of treating avians. The method first includes monitoring the avians for pulmonary hypertension syndrome or conditions known to cause pulmonary hypertension syndrome. The second step includes administering a drinking water comprising L-arginine compound to the avians once monitoring of the first step indicates presence of pulmonary hypertension syndrome or conditions known to cause pulmonary hypertension syndrome.

BRIEF SUMMARY OF DRAWINGS

FIG. 1 Summary of environmental design for example 1, which tests the tolerance of broilers for levels of Arginine in drinking water.

FIG. 39 Summary of environmental design for example 2 which tests the efficacy of drinking water supplementation with Arginine for preventing ascites in broilers.

DETAILED DESCRIPTION OF THE INVENTION

Figure 2:
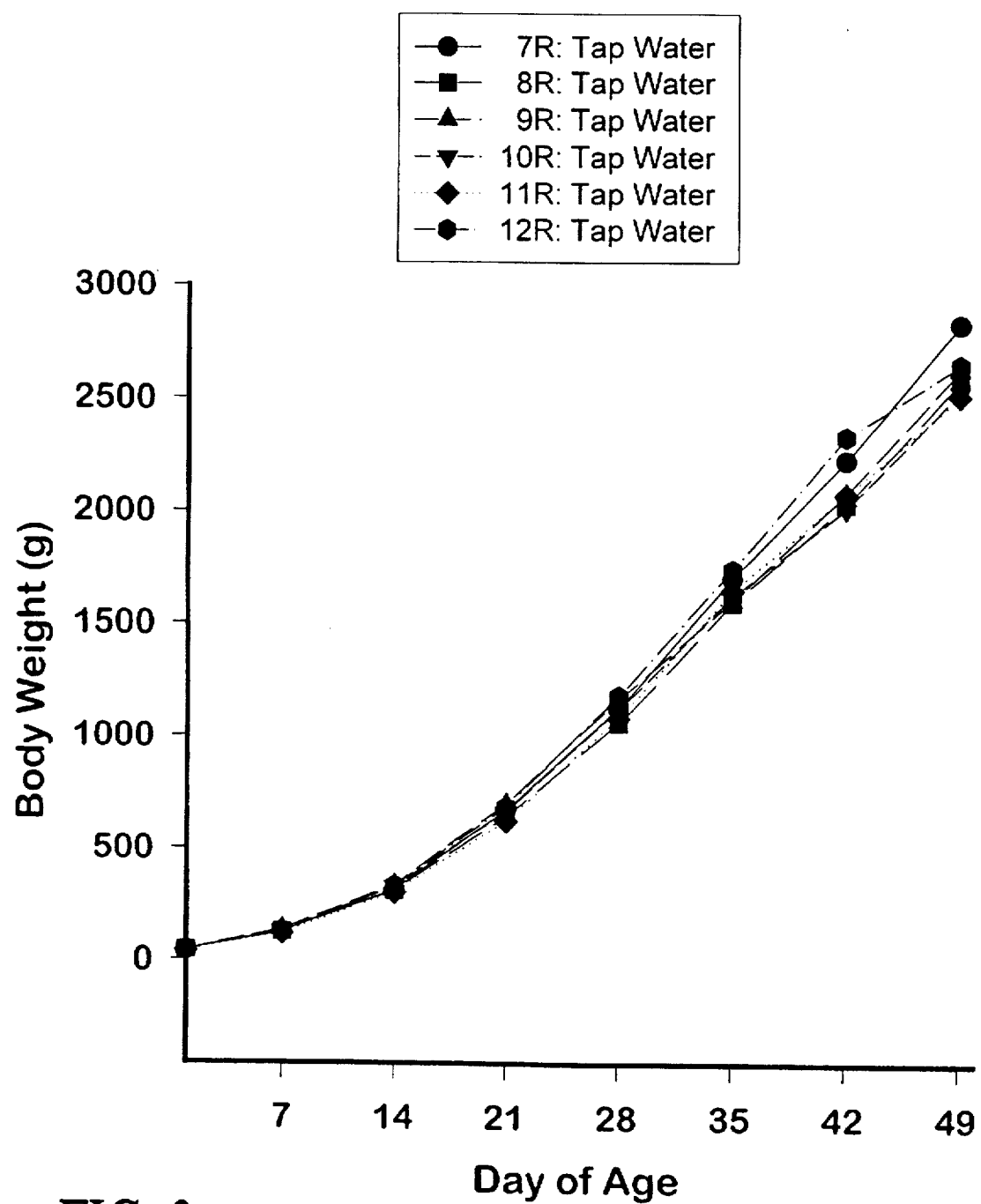
FIGS. 2–17 Growth curves for all broilers illustrating effects of increasing levels of Arginine for example 1.

One embodiment of the method of the present invention generally includes the administration of an L-arginine compound to avians through drinking water.

The amount of L-arginine compound to be utilized in the practice of the present invention, will be that amount suitable to treat and/or prevent pulmonary hypertension syndrome. Generally, the amount of L-arginine compound to be utilized in the practice of the present invention, will depend upon the size and type of avian, the specific form of the arginine compound utilized, the method of administration, pen conditions, as well as other factors.

Generally, when incorporated into the drinking water, the amount of L-arginine compound in the drinking water may be any amount that provides the desired effect of treating and/or preventing pulmonary hypertension syndrome, and that does not cause any undue negative effects.

While incorporated into the drinking water, the L-arginine compound will generally comprise at least about 0.01 weight percent of the water. Preferably, the L-arginine compound will comprise at least about 0.1 weight percent of the drinking water. More preferably, the L-arginine compound will comprise at least about 0.25 weight percent of the drinking water, even more preferably at least about 0.5 weight percent of the drinking water, and most preferably at least about 1.0 weight percent of the drinking water.

Also, it is envisioned that the concentration of L-arginine in the drinking water can be varied according to the developmental stage of the avian. For example, as the avian ages, it is believed that less L-arginine compound will be necessary to prevent and/or treat pulmonary hypertension syndrome. Thus, the concentration of L-arginine in the drinking water could be decreased with the increasing age of the avian.

The upper level for the amount of L-arginine compound to be utilized in the drinking water will generally be controlled by economic factors, by any undue effects caused by L-arginine (at present inventors know of none), toxicity levels, and by physical limitations, i.e., solubility of the L-arginine compound in the drinking water. While amounts of L-arginine compound above the solubility level may be utilized, it is generally preferred to utilize amounts of L-arginine below the solubility level to facilitate intake by the avians, which is about 18 wt % L-arginine compound in water at ambient temperature.

One advantage of incorporating the L-arginine compound into the drinking water, is that it may be added quickly should its need arise. In contrast, commercial chicken operations generally formulate chicken feed in two week batches, so L-arginine compound cannot be easily added to the feed, but will generally be added to the next batch, which might be up to two weeks away.

L-arginine compounds suitable for use in the practice of the present invention, include any form of L-arginine, any substituted L-arginine, and any compound incorporating a form of L-arginine, provided that the desired effect of treating ascites is obtained. Examples of suitable L-arginine compounds include L-arginine (free base), substituted L-arginines, organo L-arginines, L-arginine salts, and any other suitable form of L-arginine. Preferably, the L-arginine compound comprises L-arginine in a free base form.

Suitable anions for salts of L-arginine which may be utilized include bromide, fluoride, iodide, borate, hypobromite, hypochlorite, nitrite, nitrate, hyponitrite, sulfate, disulfate, sulfite, sulfonate, phosphate, diphosphate, phosphite, phosphonate, diphosphonate, perchlorate, perchlorite, oxalate, malonate, succinate, lactate, carbonate, bicarbonate, acetate, benzoate, citrate, tosylate, permanganate, manganate, propanolate, propanoate, ethandioate, butanoate, propoxide, chromate, dichromate, selenate, orthosilicate, metasilicate, pertechnetate, technetate, dimethanolate, dimethoxide, thiocyanate, cyanate, isocyanate, and the like. The suitable cation for most salts is hydrogen, however, other cations such as sodium, potassium and the like would be acceptable in the preparation of such a salt. It would advantageous if the specific salt form selected allowed a pH close to neutral.

The inventors believe that the L-arginine compound is most effective at preventing pulmonary hypertension syndrome if administration is commenced as soon after hatching as possible. Obviously, economic factors may dictate a much more limited use of the L-arginine compound. If the administration of L-arginine compound is not commenced immediately after hatching, then it is preferred that commencement of administration of the L-arginine compound begin at least before the avians are five weeks old, and preferably before the avians are three weeks old.

As an alternative, pen conditions could be monitored, and at the onset of conditions likely to encourage pulmonary hypertension syndrome, or once it is recognized that birds in the flock are suffering from hypertension syndrome, L-arginine compound could be administered to the flock. For example, once temperatures drop below the avian's thermoneutral zone, about 85° F. for hatchling chicks, about 70° F. for 5 week old chicks, and about 68° F. for 6 week old chicks, the incidence of pulmonary hypertension syndrome will increase. As another example, once temperatures drop, the chicken houses are closed up and heated, with ventilation of fresh air reduced to preserve heat. Conditions of poor ventilation result in increased rates of pulmonary hypertension syndrome. Exposure to agents of respiratory distress, i.e. certain bacteria, dusts, ammonia and viruses, are also known to cause pulmonary hypertension syndrome. Finally, in some instances, feed is obtained which is high in salt, i.e., bakery products such as pretzel flour. High salt diets are also linked to an increase in pulmonary hypertension syndrome.

The present invention is believed to be suitable for treating any avian suffering from pulmonary hypertension syndrome. Generally, such avians which may be treated by the present invention includes chicken, turkey, duck, pheasant, quail, geese, ostrich and emu. Preferably, the present invention is utilized in the treatment of chicken, turkey and duck. Most preferably, the present invention is utilized in the treatment of chicken.

EXAMPLES

The following examples are provided merely to illustrate the present invention, and are not intended to limit the scope of the claims.

Example 1

The Tolerance of Broilers for Low, Medium and High Levels of Drinking Water Supplementation with Arginine.
Experimental Design Six environmental chambers were divided in half, with 50 male broiler chicks per half as illustrated in FIG. 1. FIG. 1 shows the chamber assignments with 7F–12F depicting the front half of each chamber and with 7R–12R depicting the rear half of each chamber. A single 23% crude protein, 3,000 kcal/kg ME broiler "starter diet" was provided ad libitum for the seven week duration of the experiment. Nipple waterers were used. Referring to FIG. 1, Birds in the rear half of each chamber were supplied with tap water, whereas birds in the front half were supplied with low, medium, or high levels of arginine free base or arginine HCl. Specifically, Table 1 shows level 3 Arginine free base for chamber 7F, Table 2 shows the level 3 Arginine HCl for chamber 8F, Table 3 shows level 2 Arginine free base for chamber 9F, Table 4 shows the level 2 Arginine HCl for chamber 10F, Table 5 shows level 1 Arginine free base for chamber 11F, Table 6 shows the level 1 Arginine HCl for chamber 12F.

Figure 3:
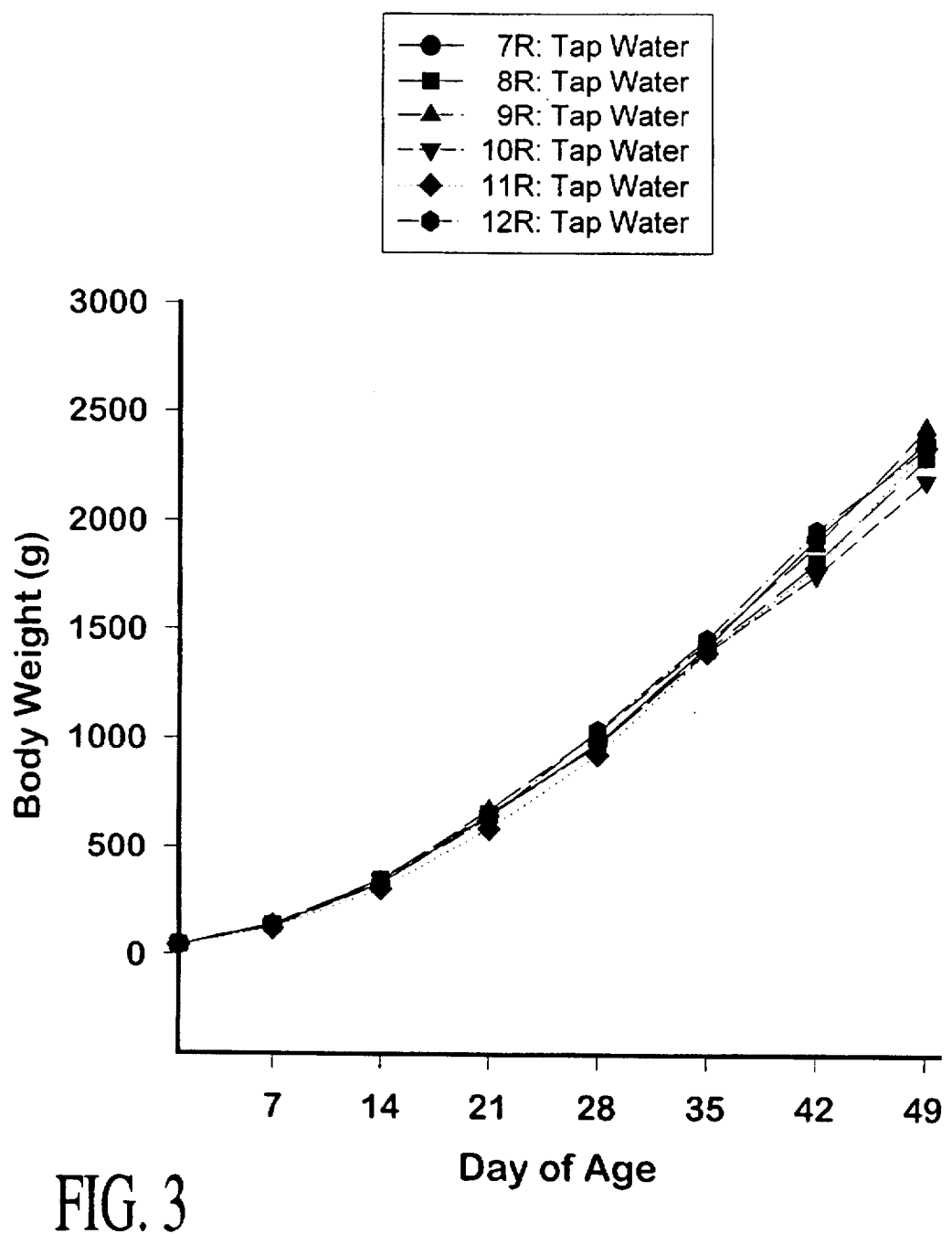
Figure 4:
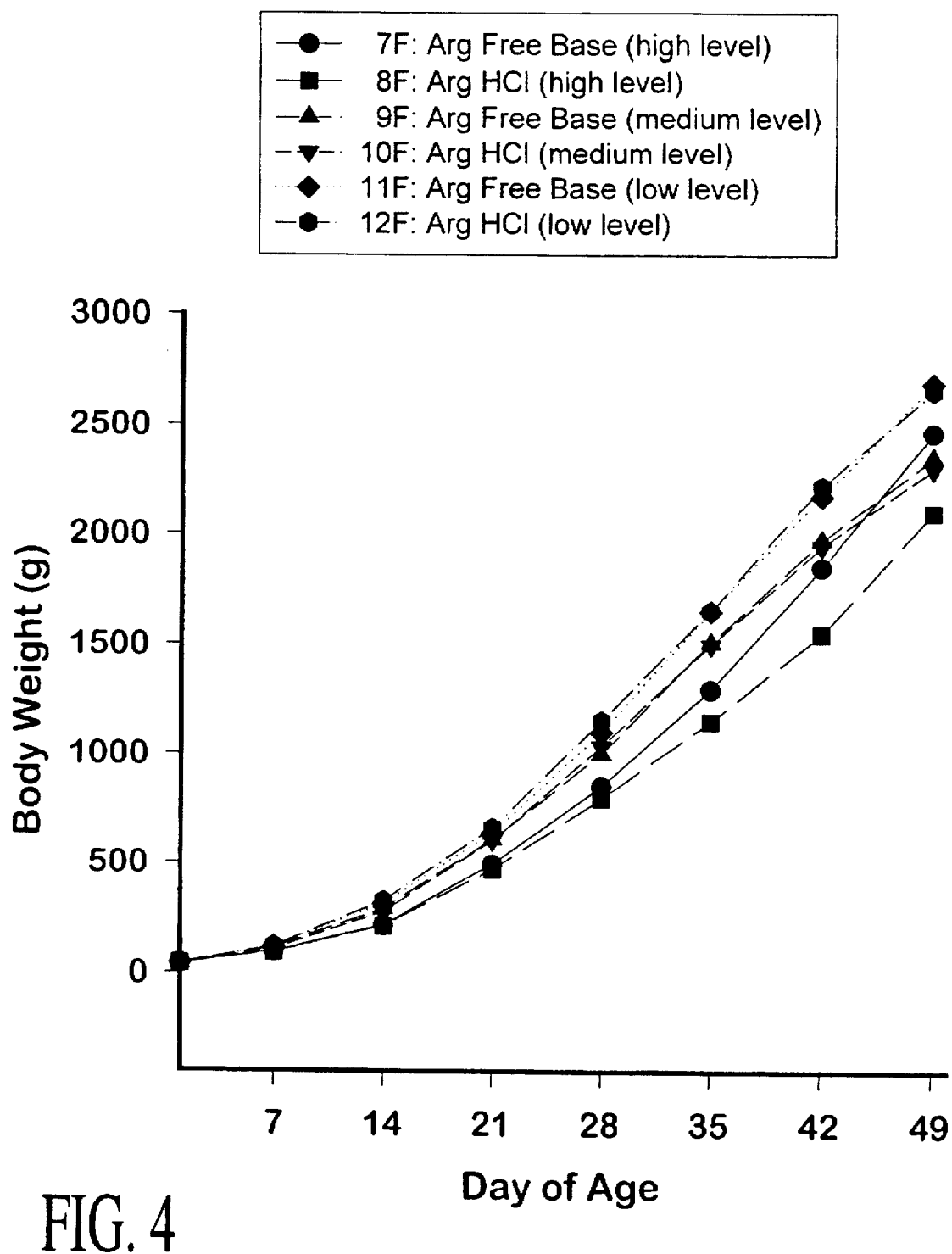
Figure 5:
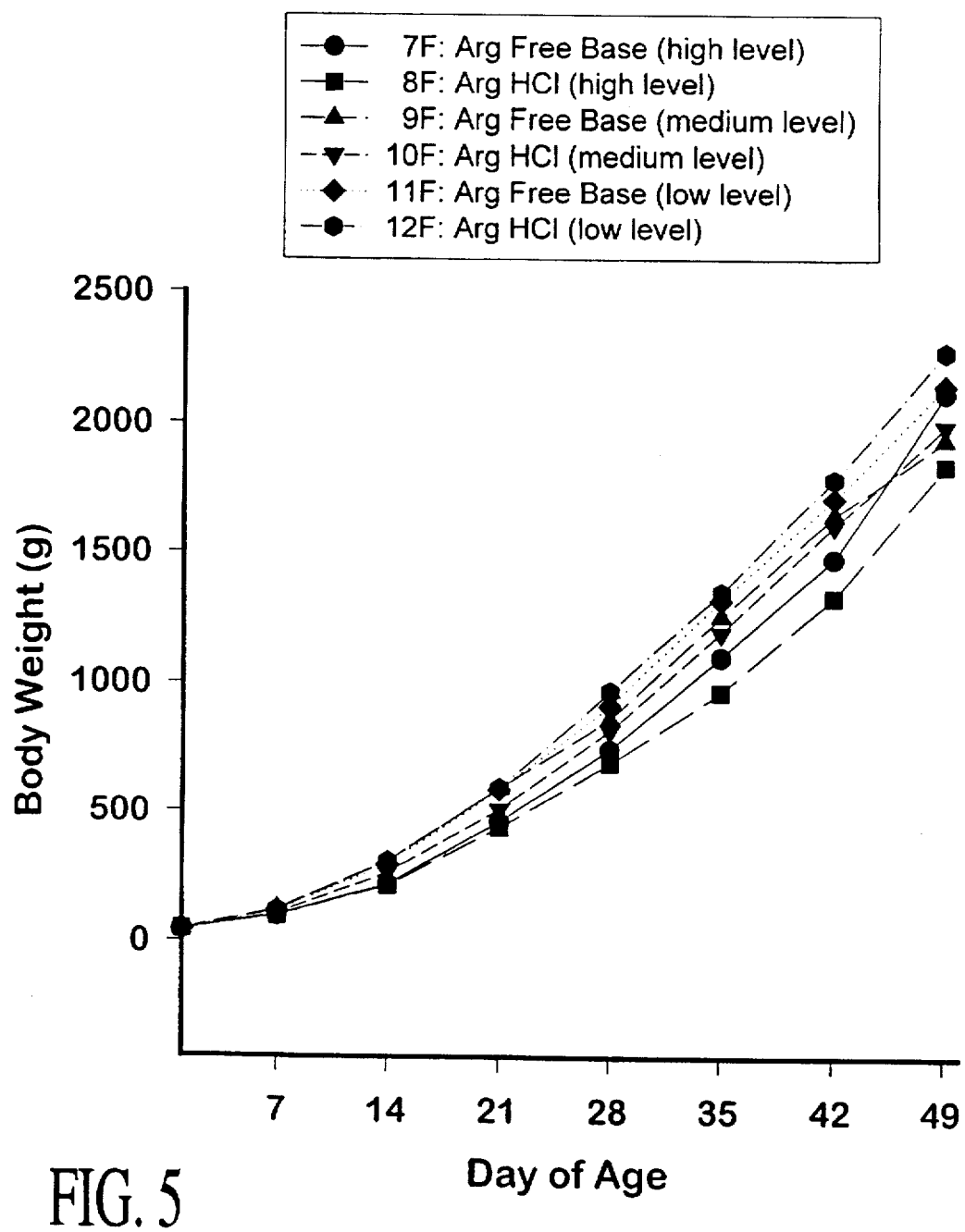
Figure 6:
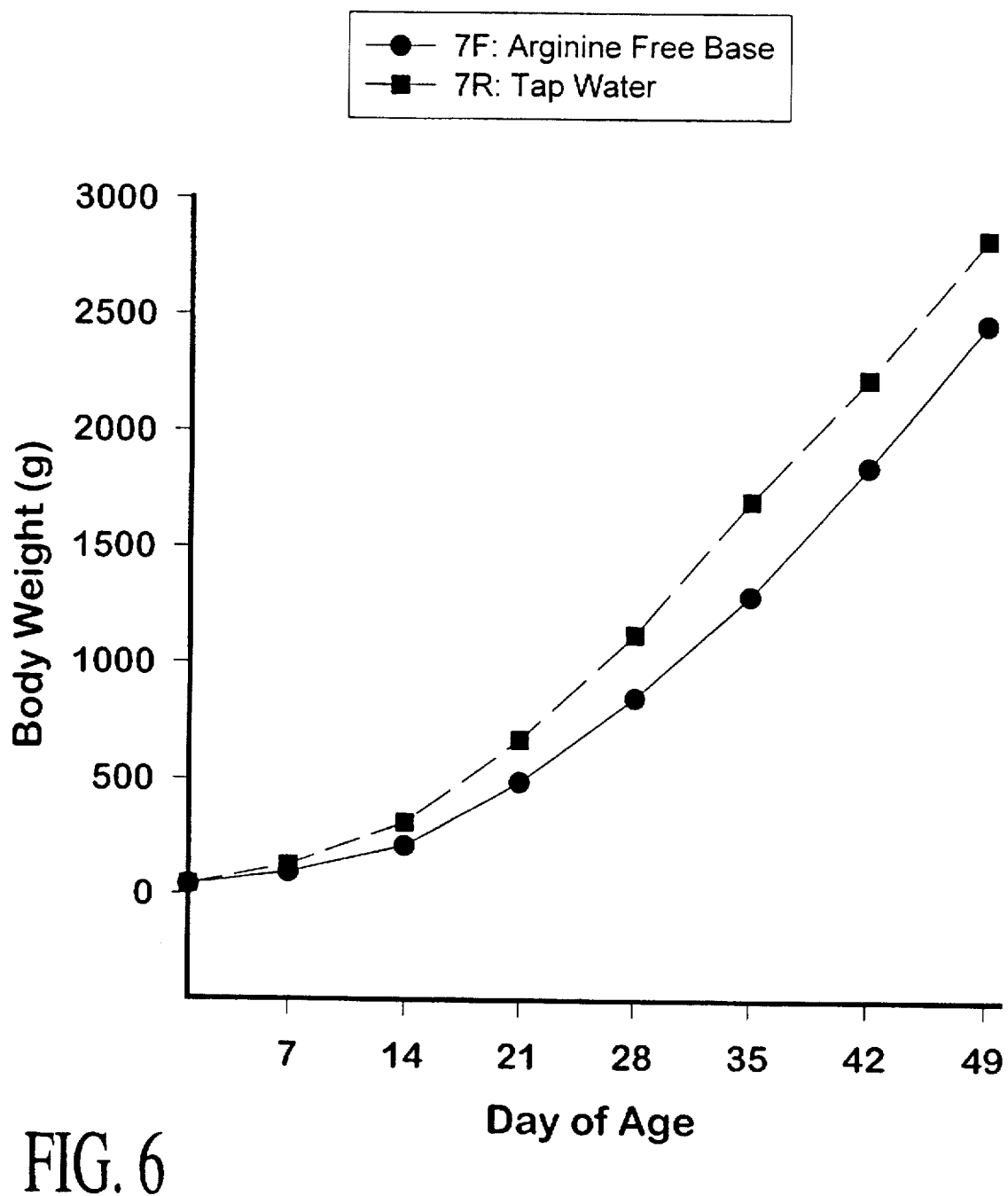
Figure 7:
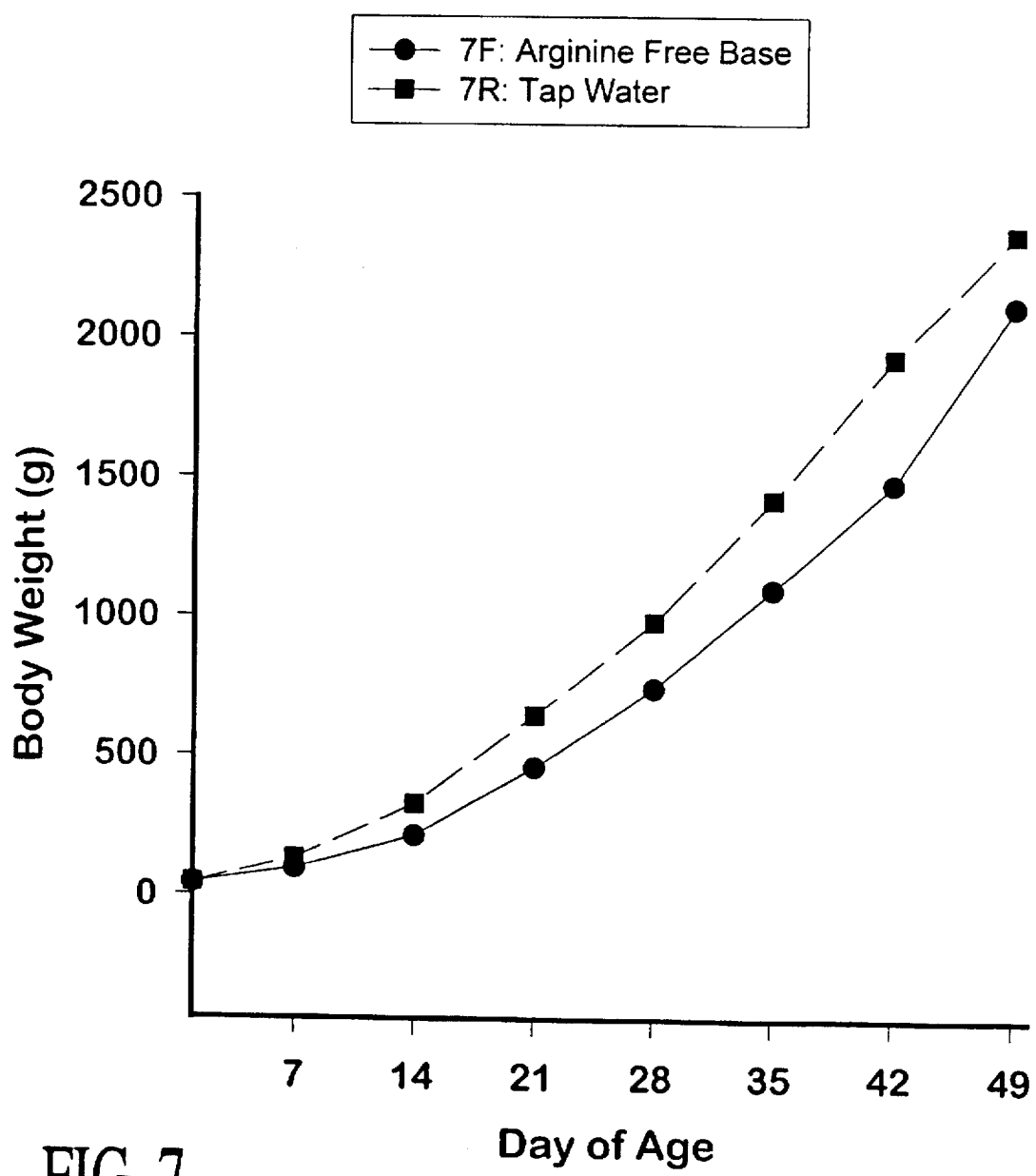
Figure 8:
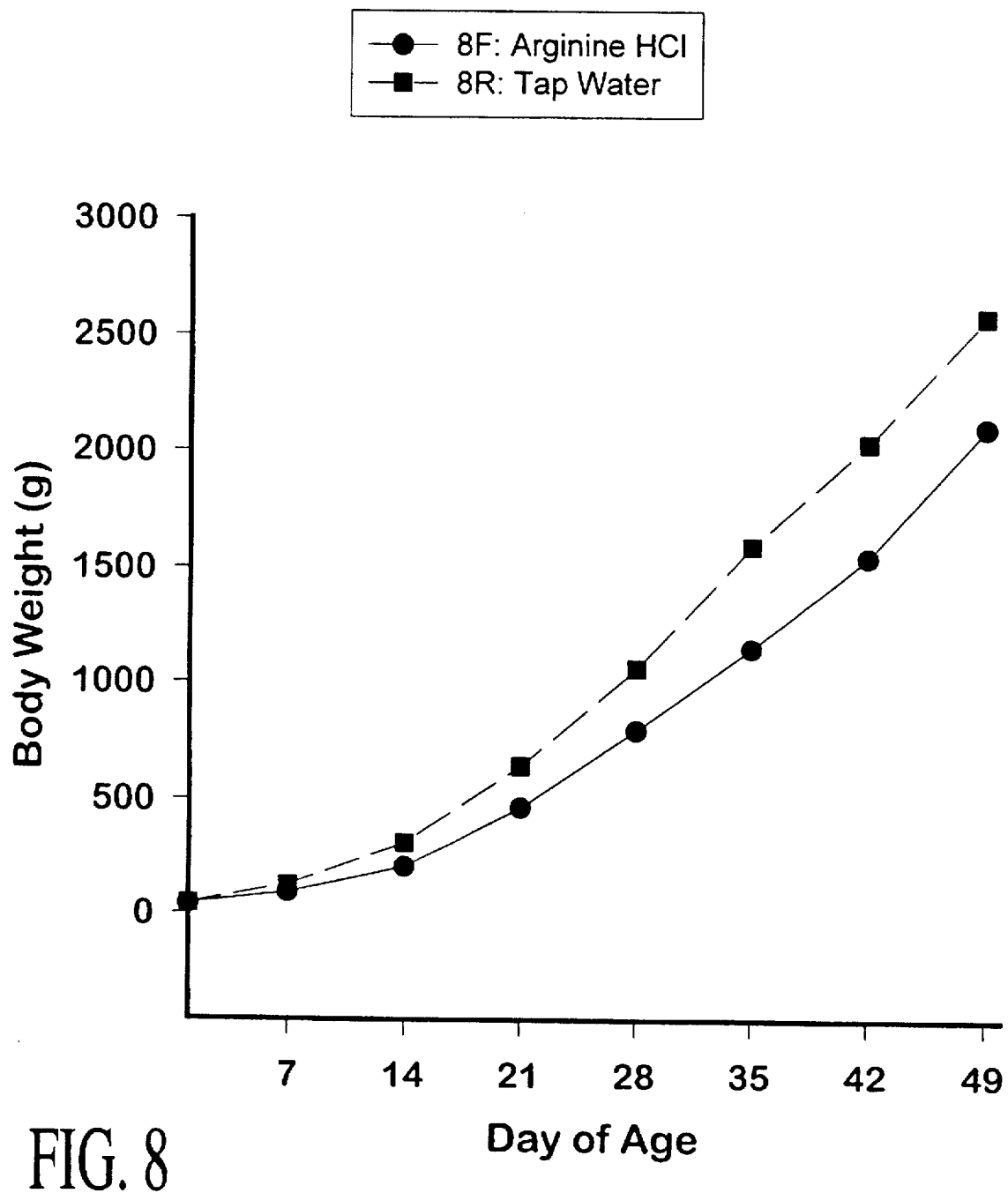
Figure 9:
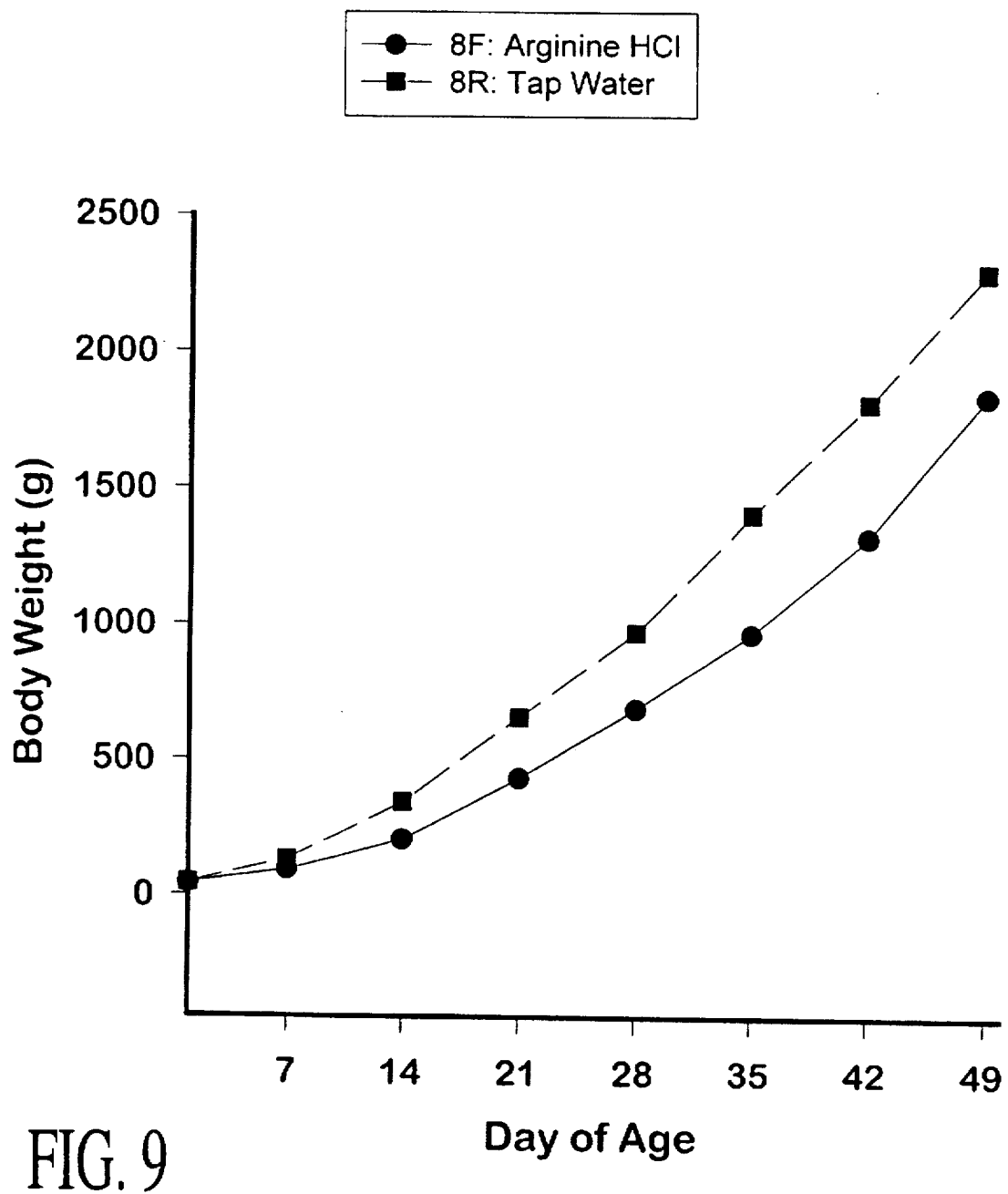
Figure 10:
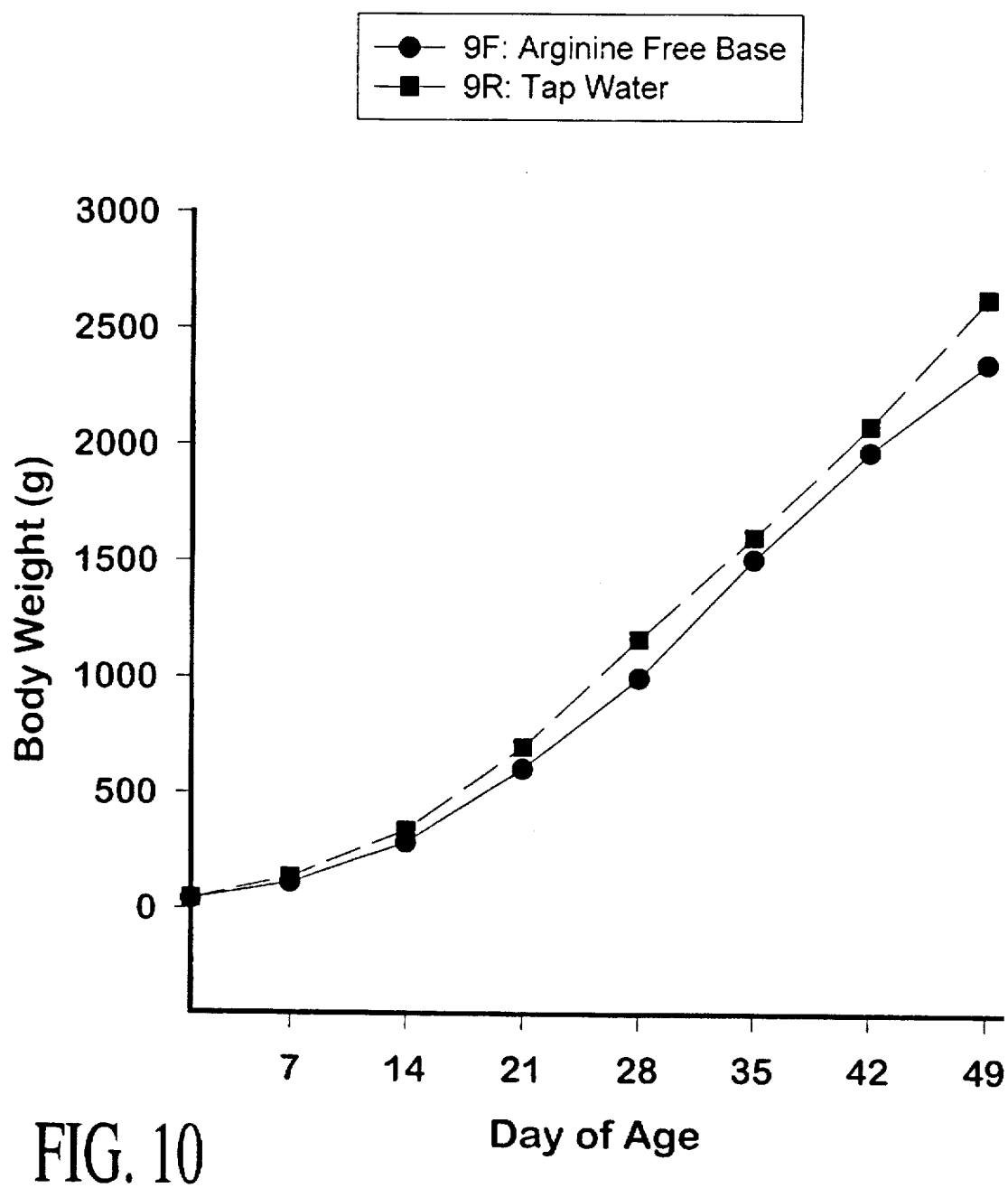
Figure 11:
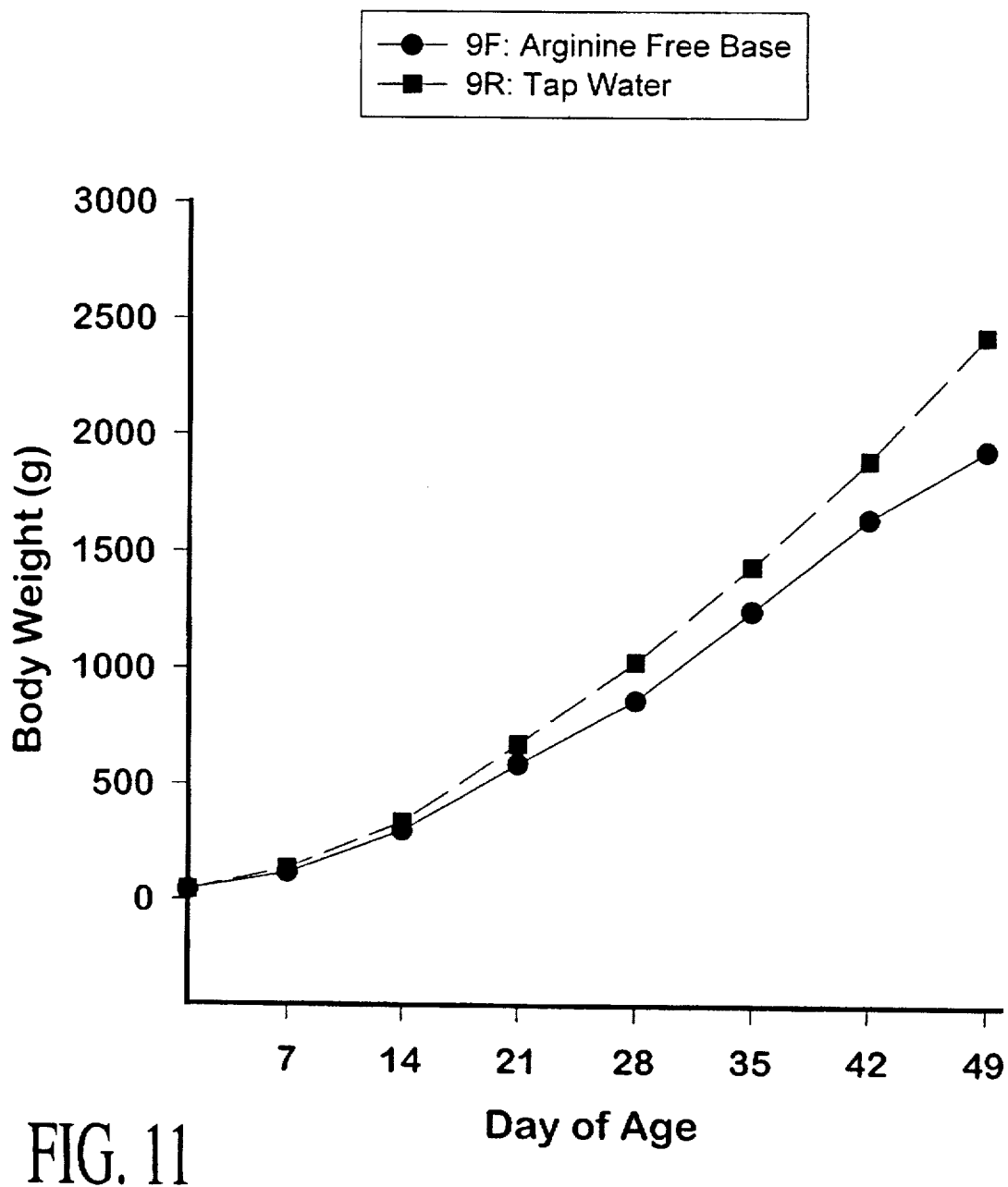
Figure 12:
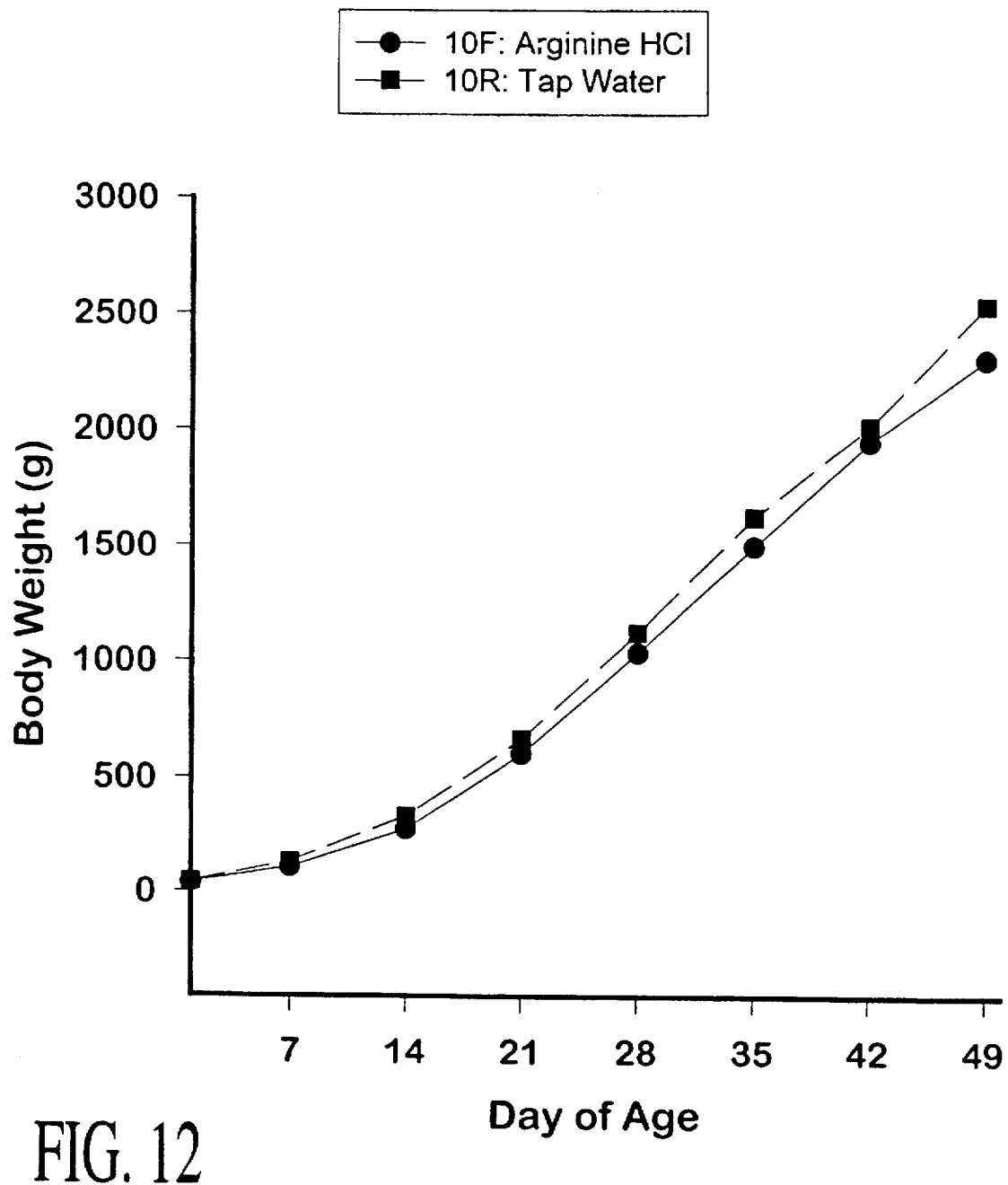
Figure 13:
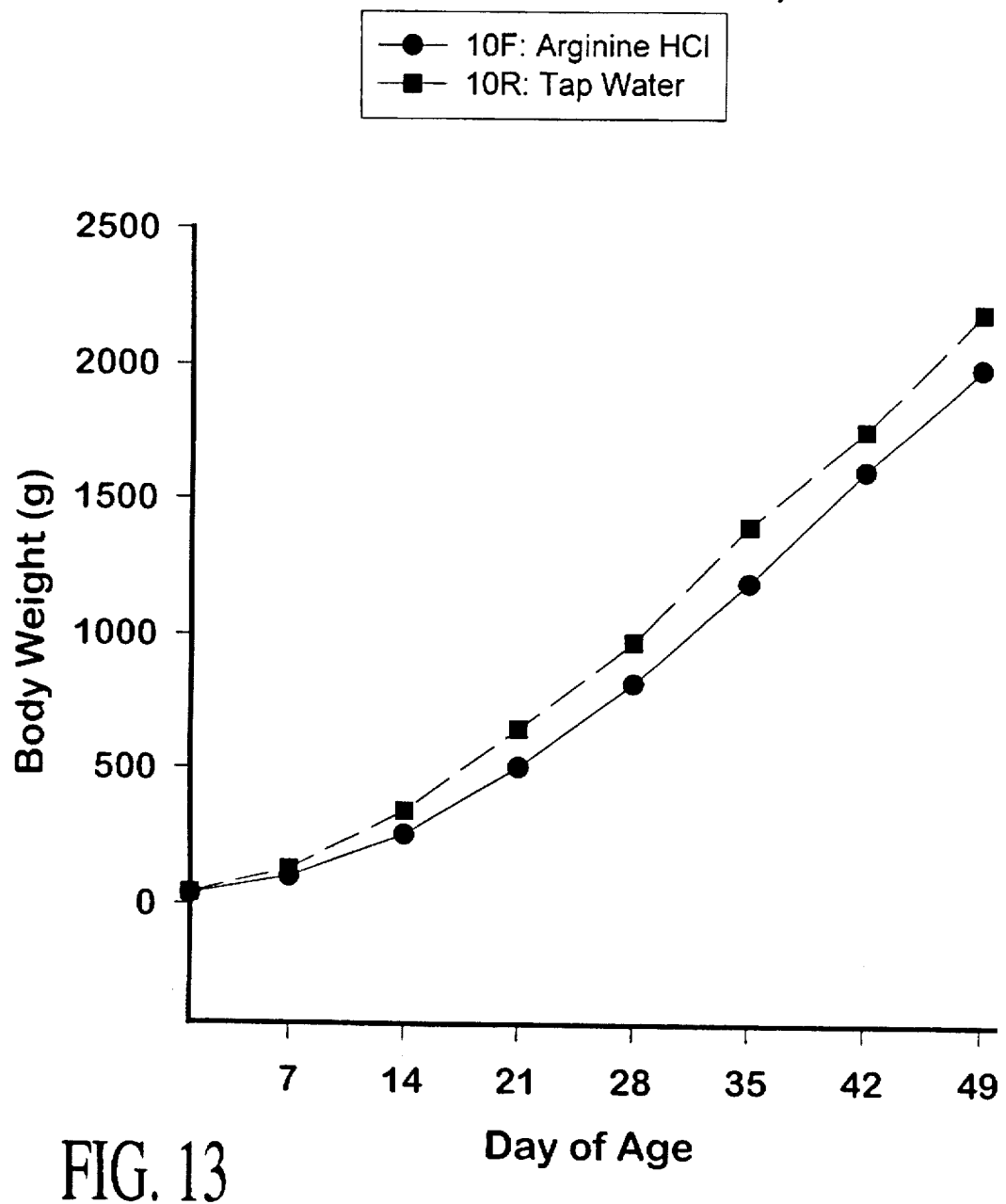
Figure 14:
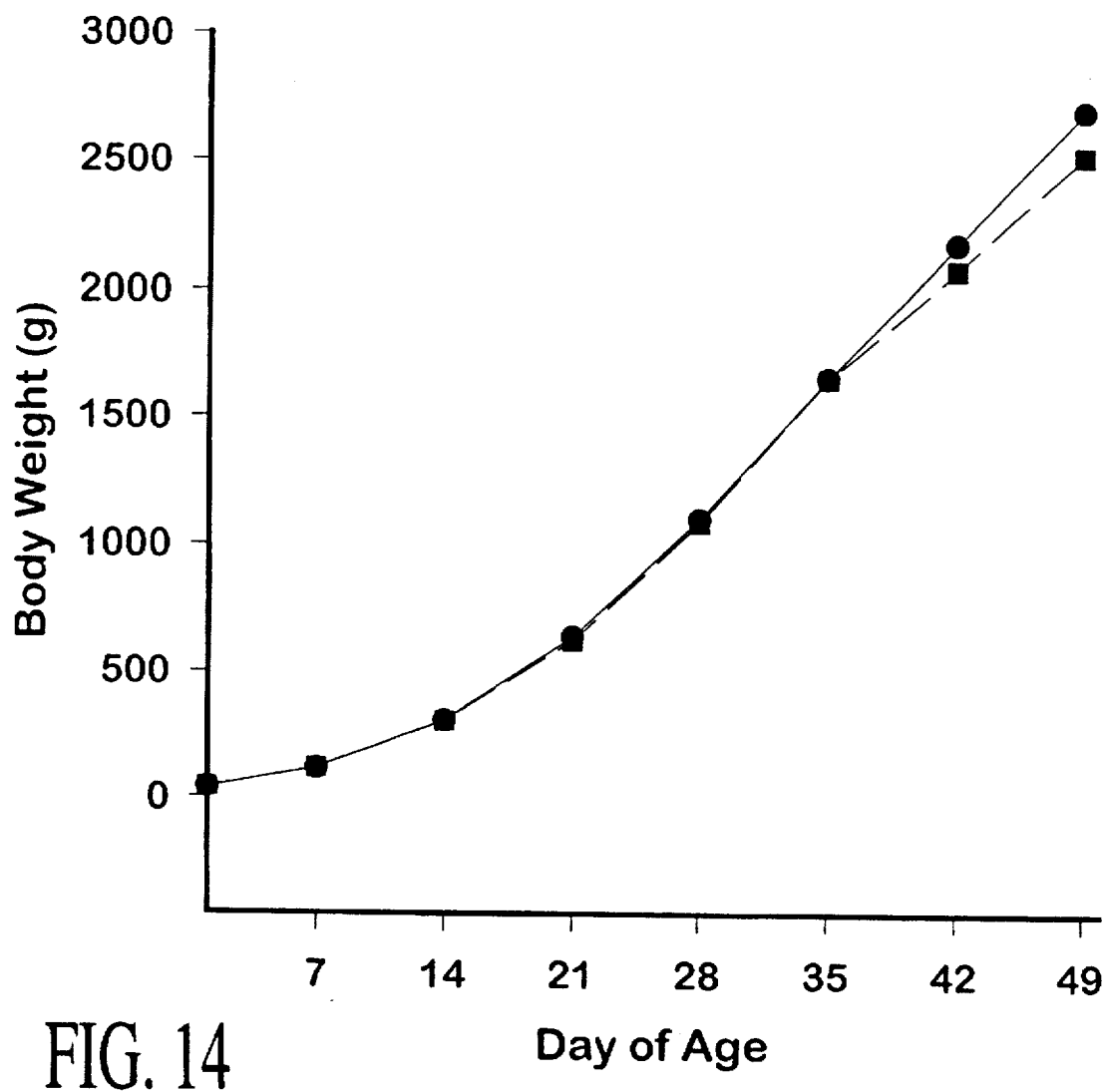
Figure 15:
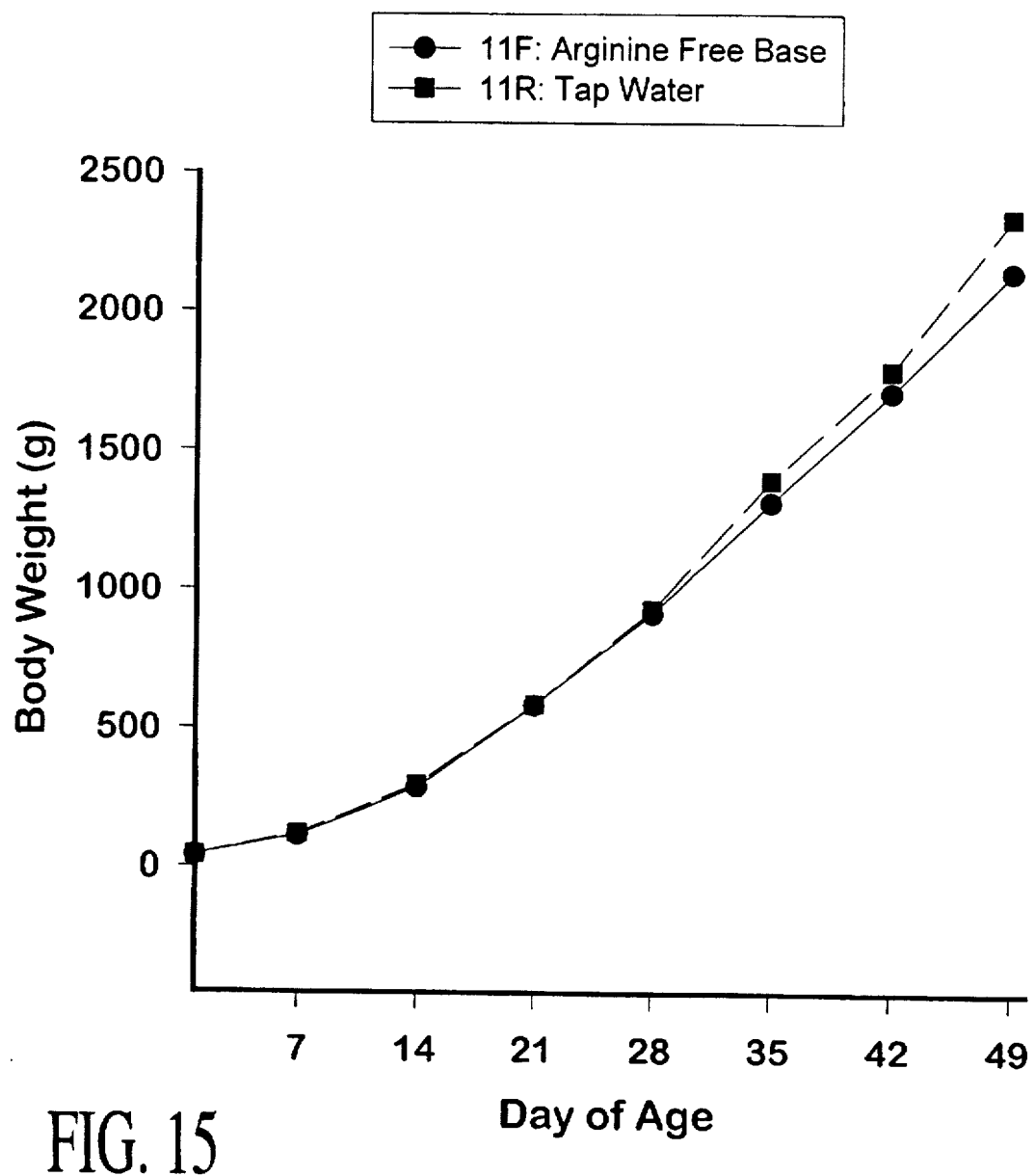
Figure 16:
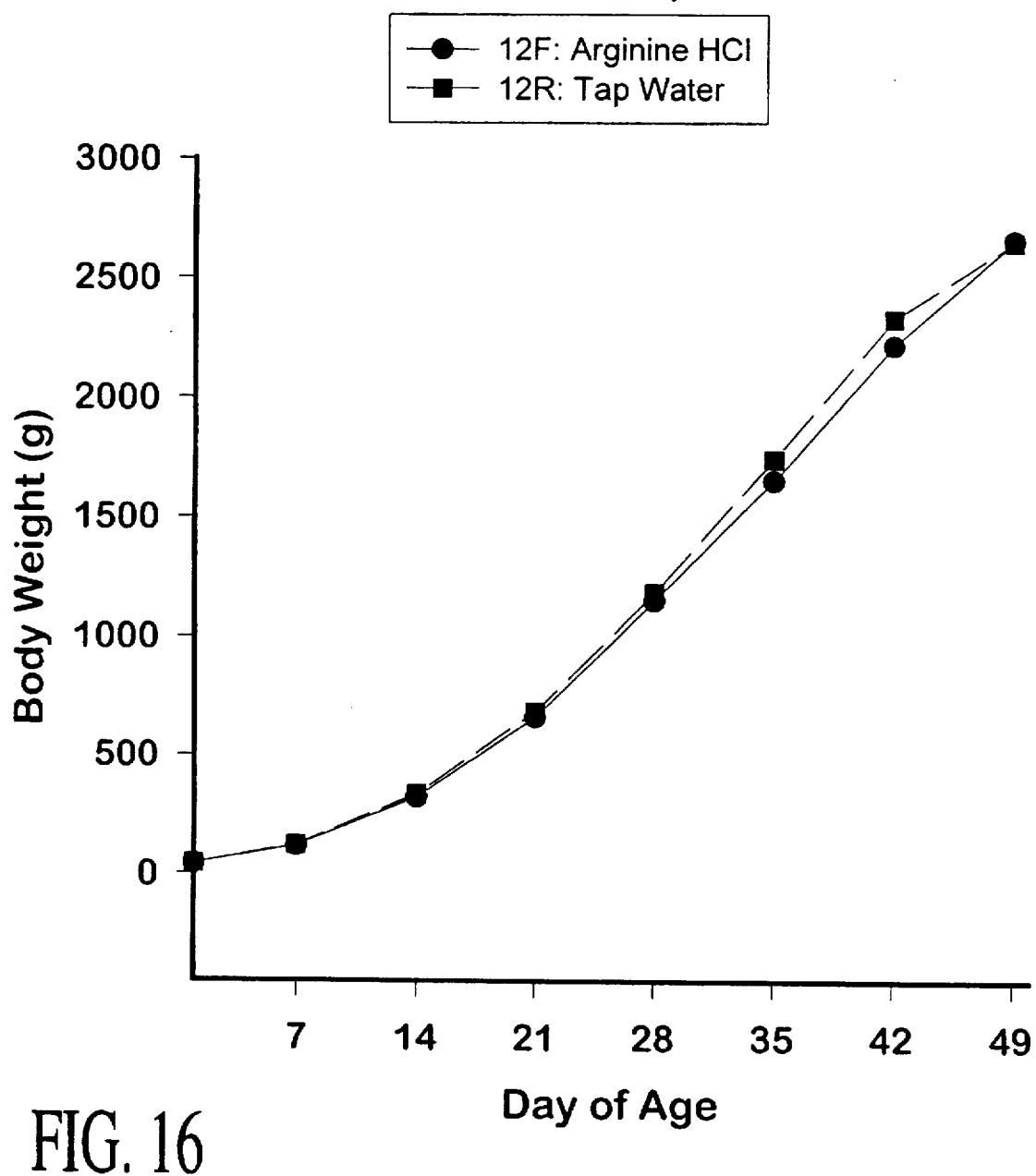
Figure 17:
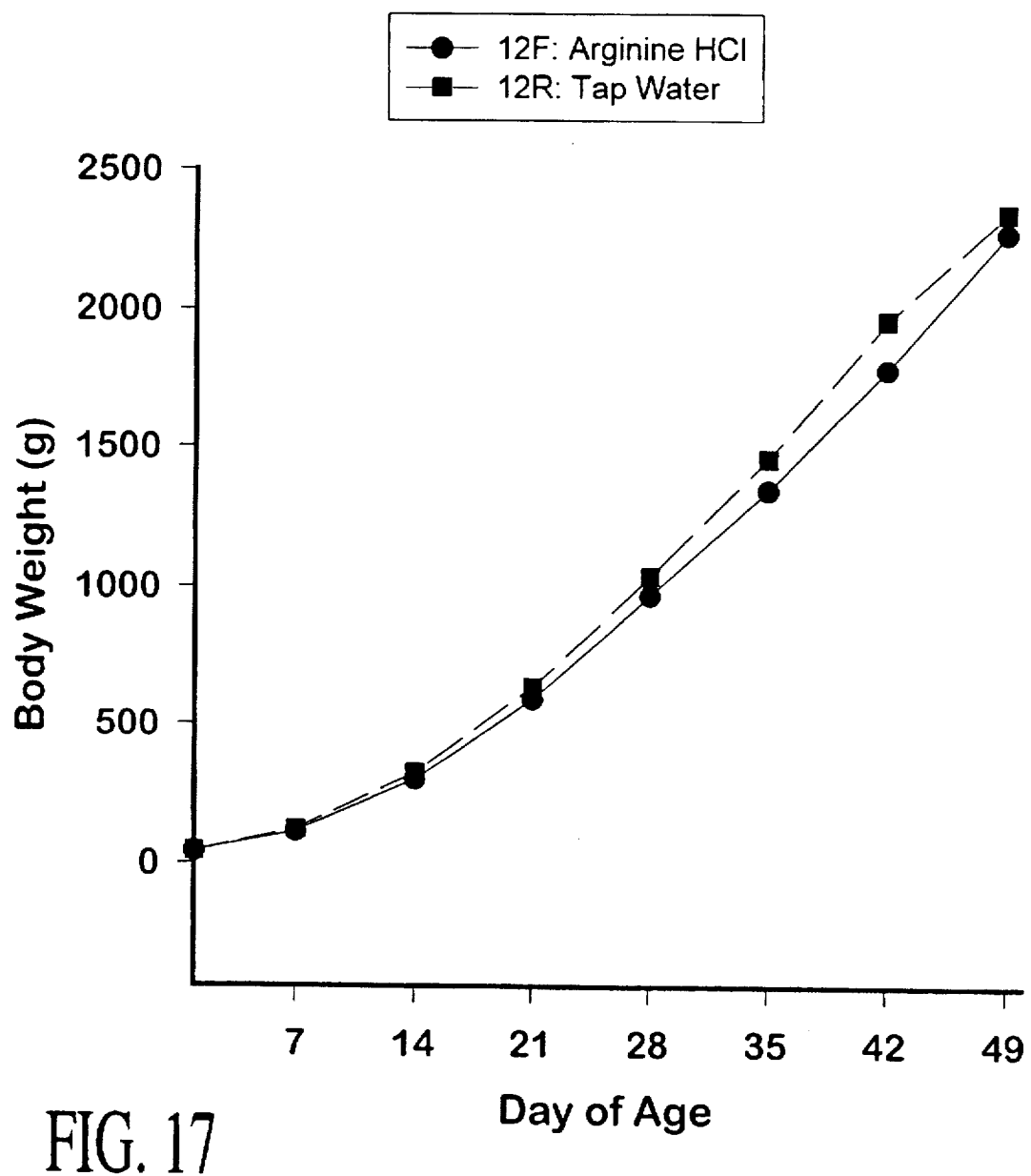
Figure 18:
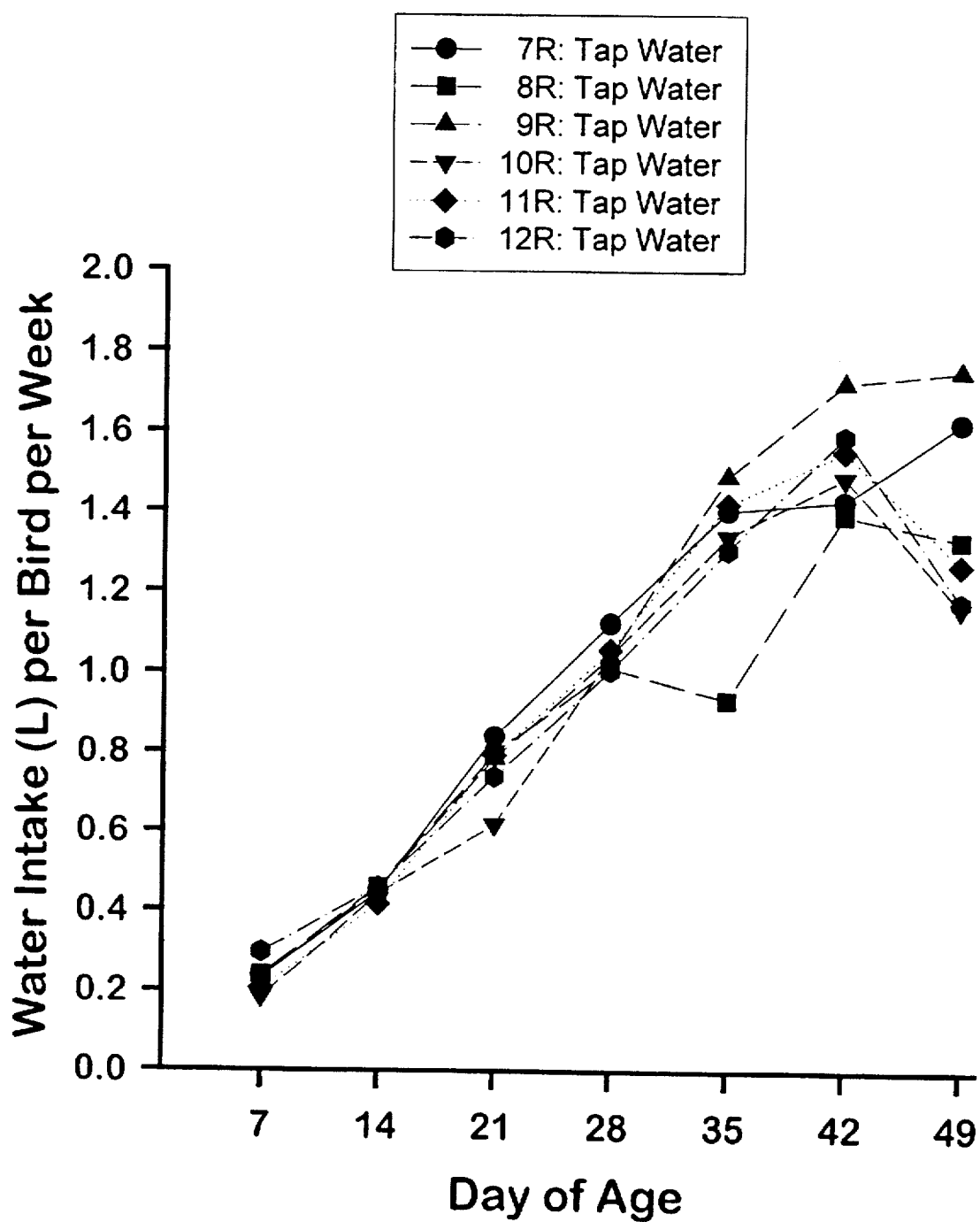
FIGS. 18–25 Water intake Curves illustrating water intake per bird for example 1.
Figure 19:
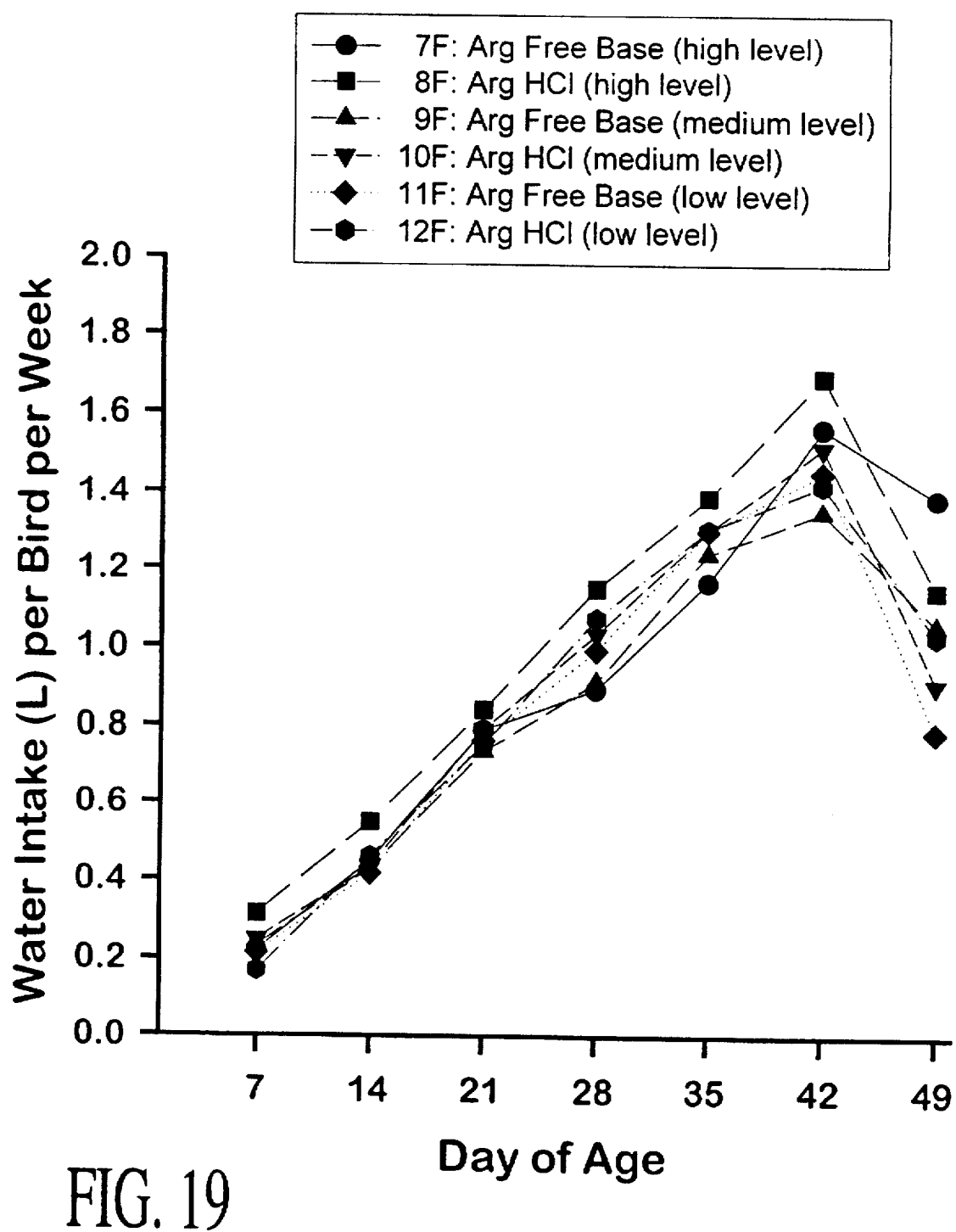
Figure 20:
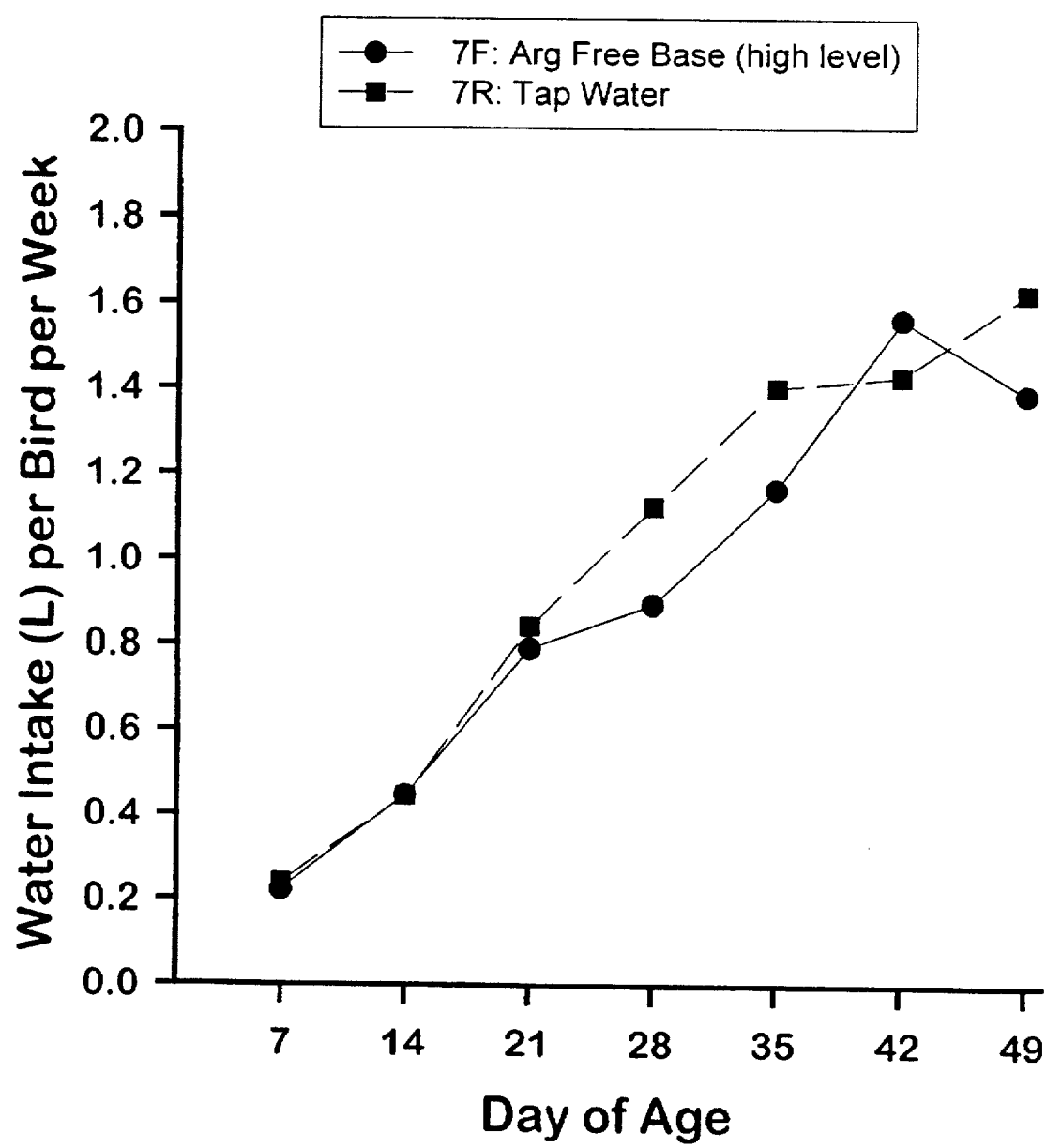
Figure 21:
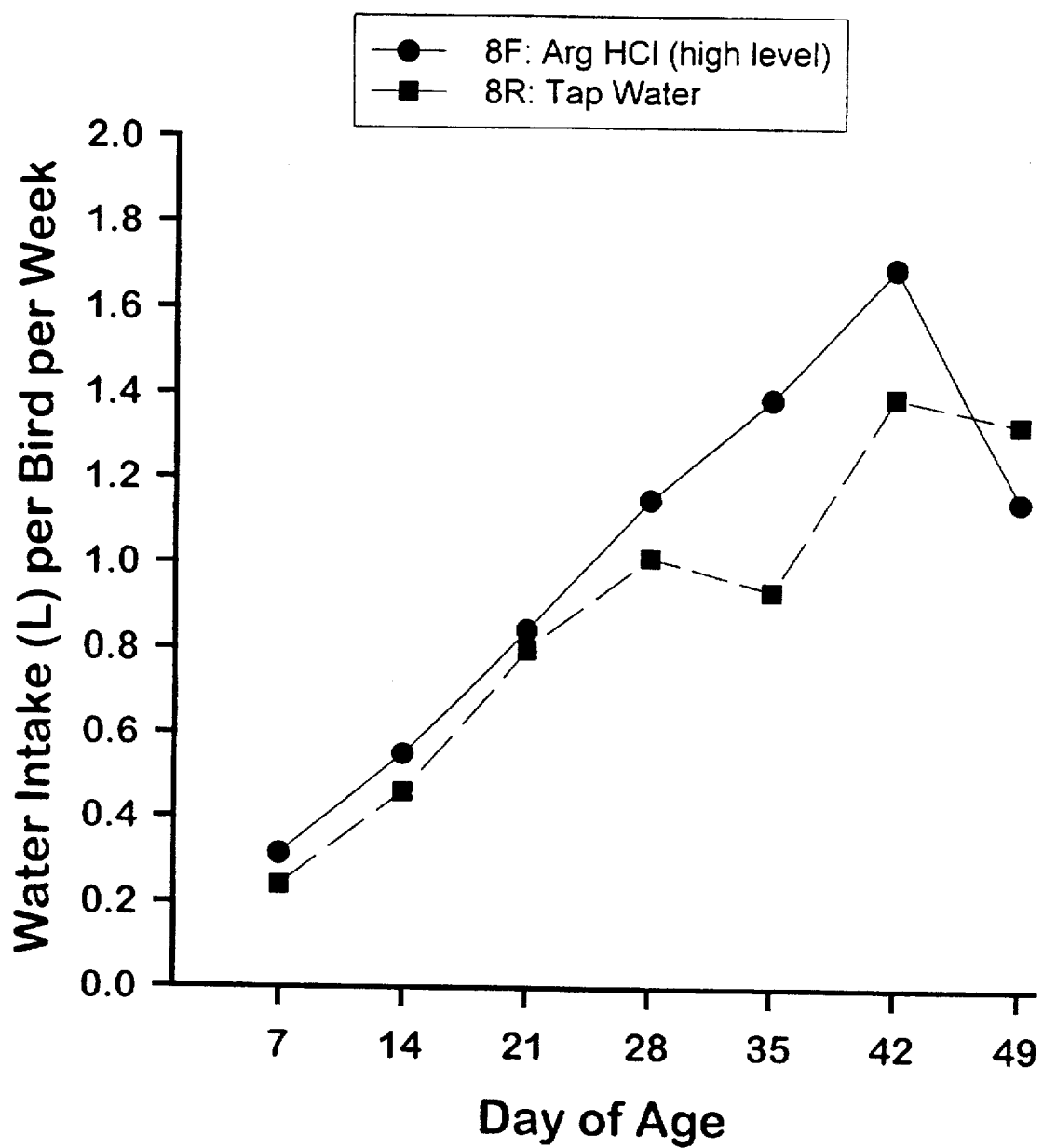
Figure 22:
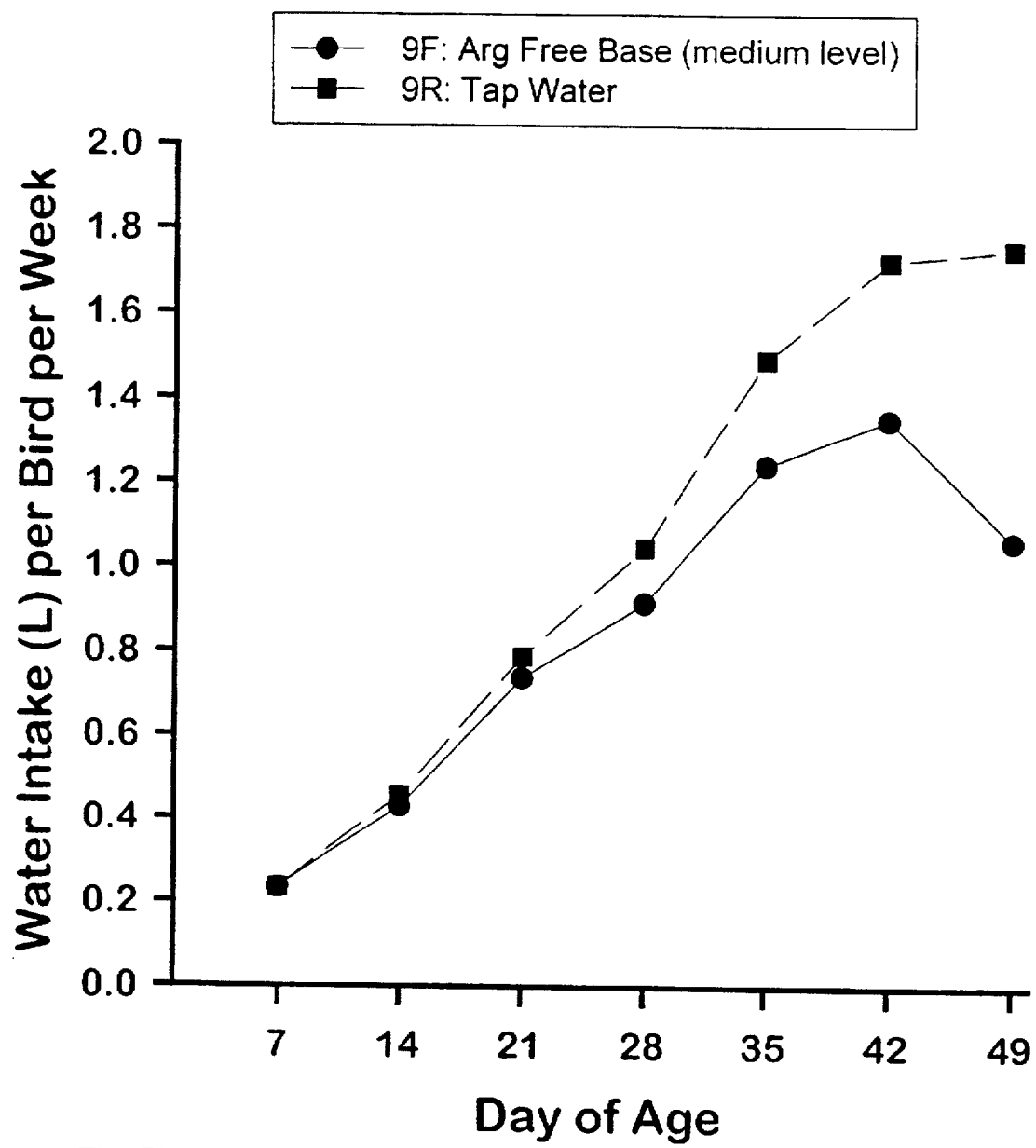
Figure 23:
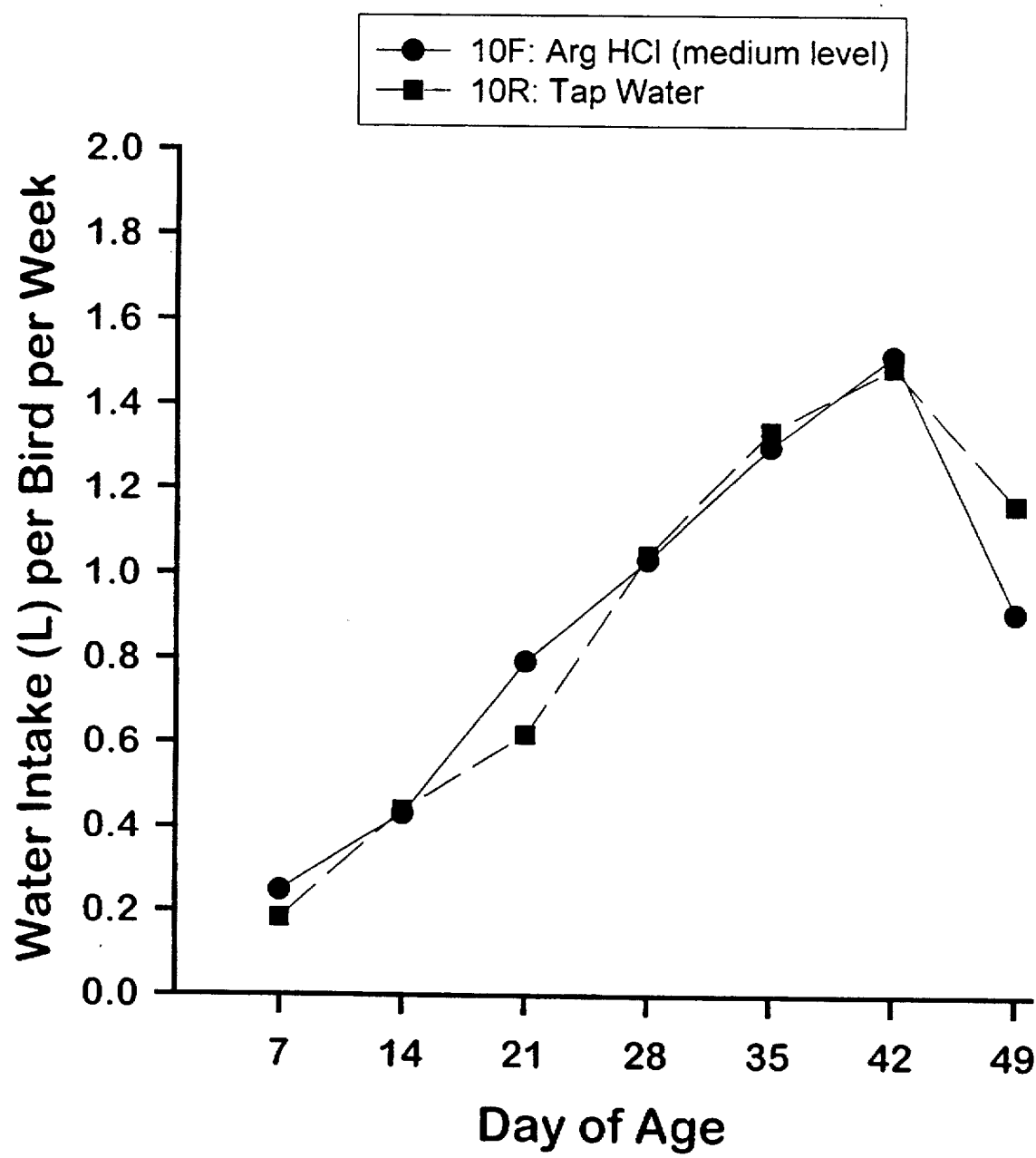
Figure 24:
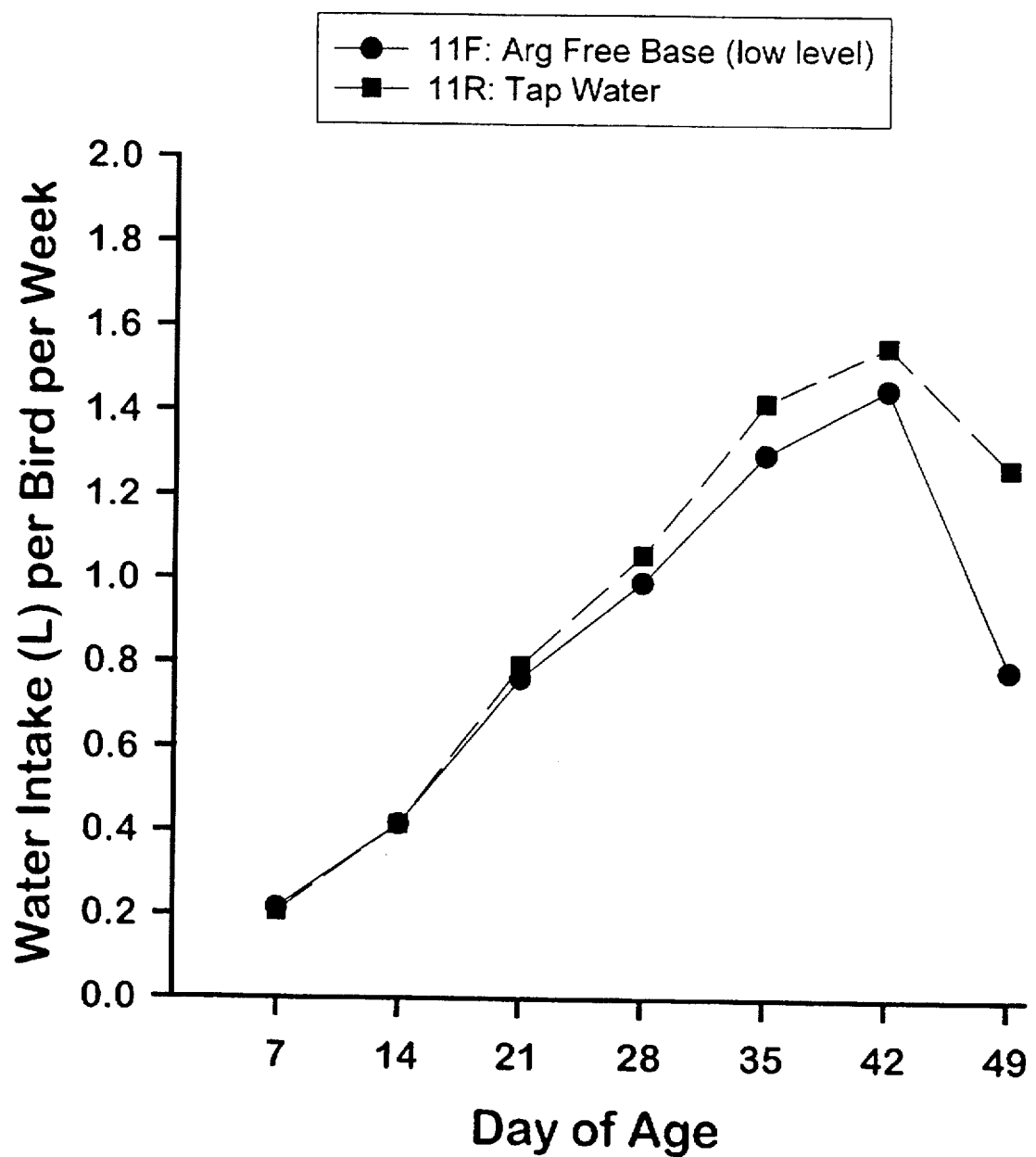
Figure 25:
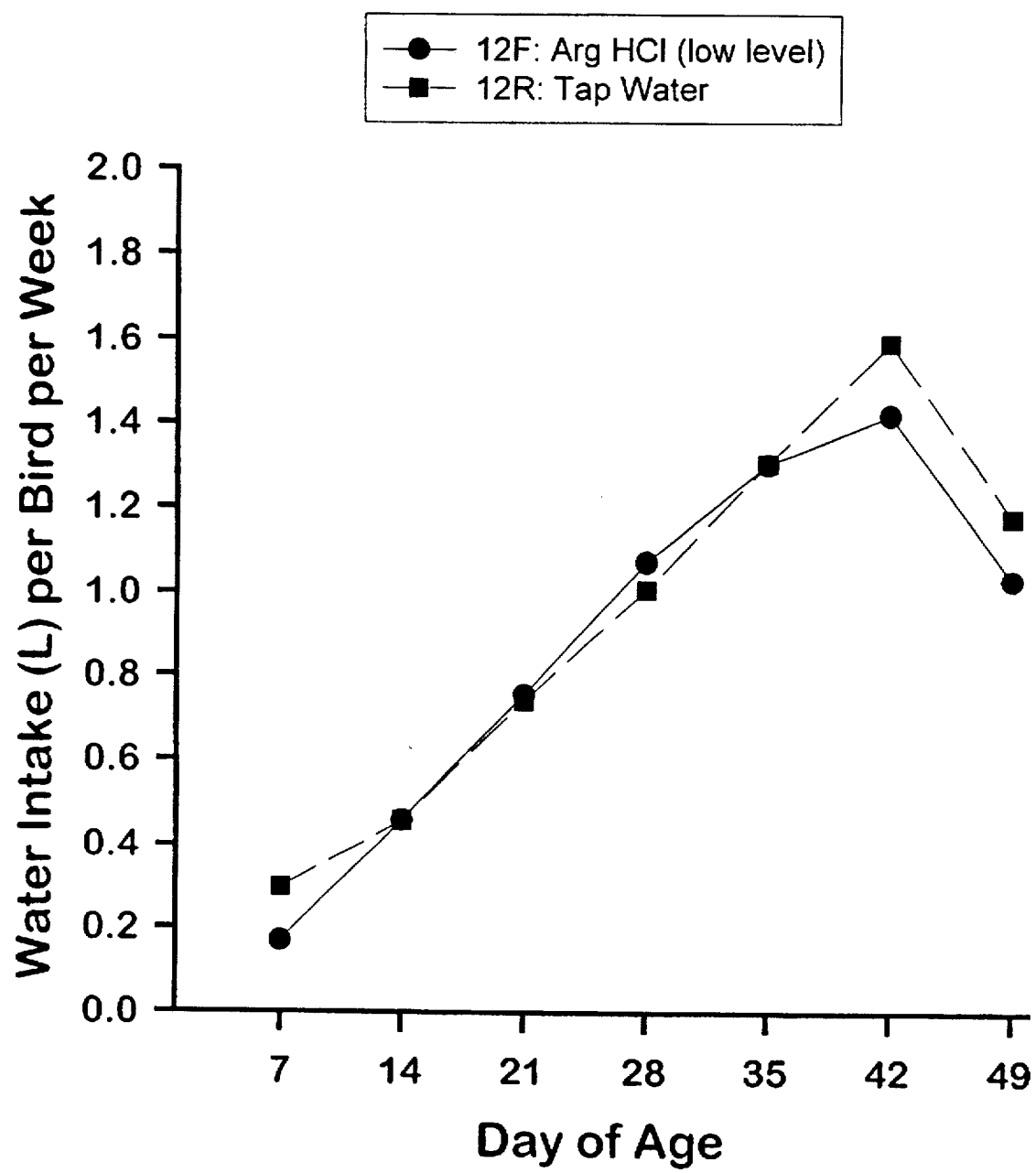
Figure 26:
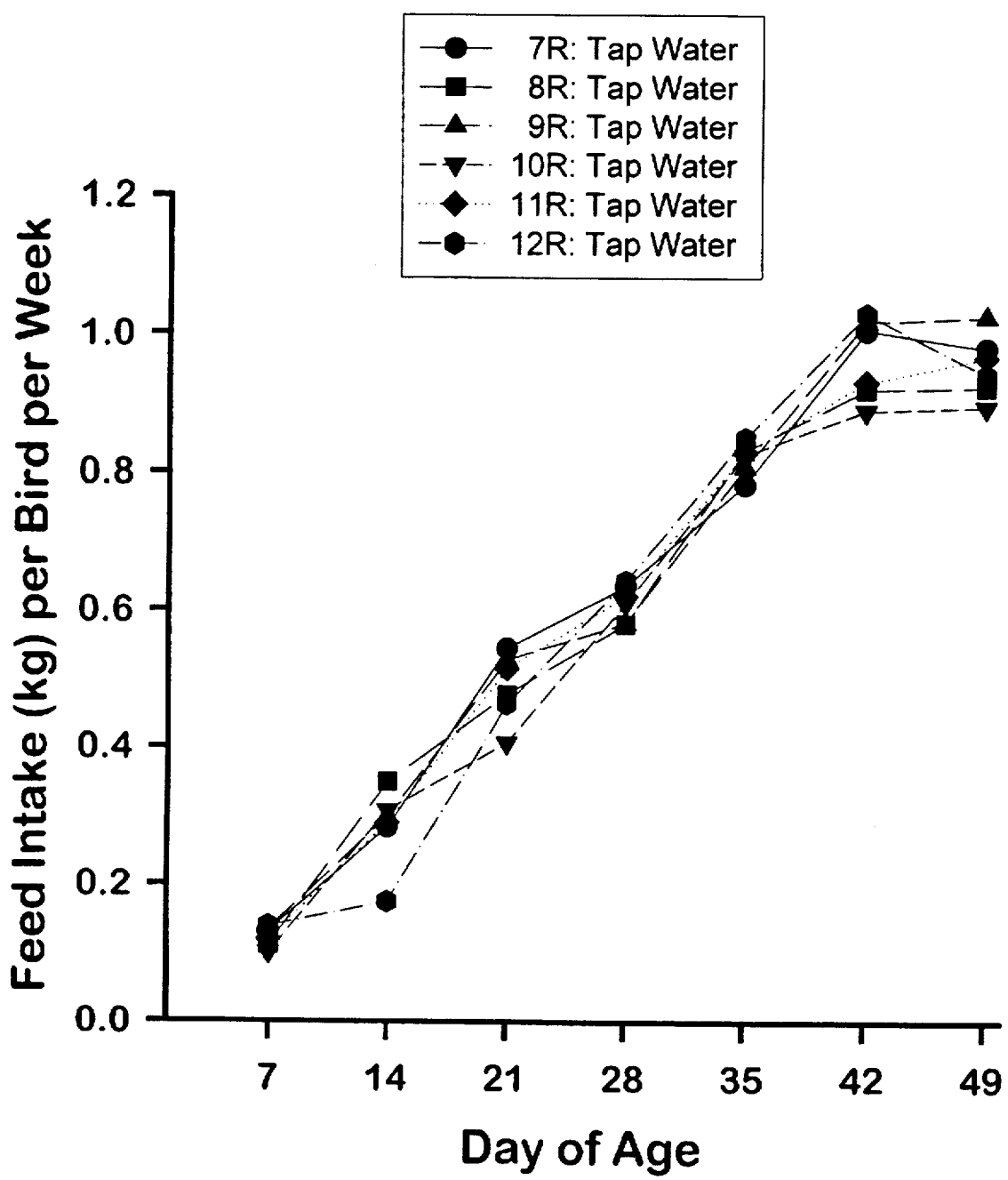
FIGS. 26–33 Feed intake Curves illustrating feed intake per bird for example 1.
Figure 27:
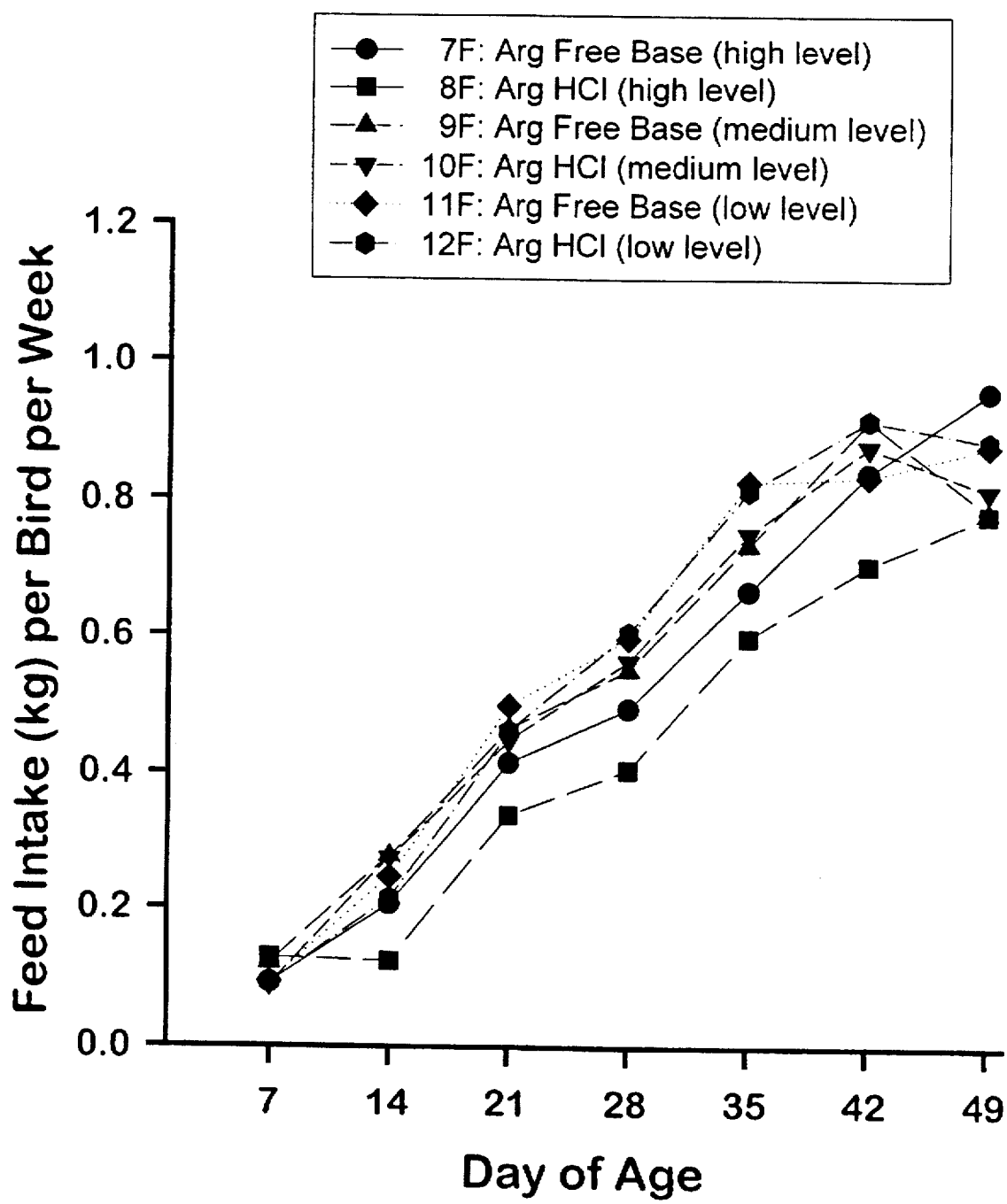
Figure 28:
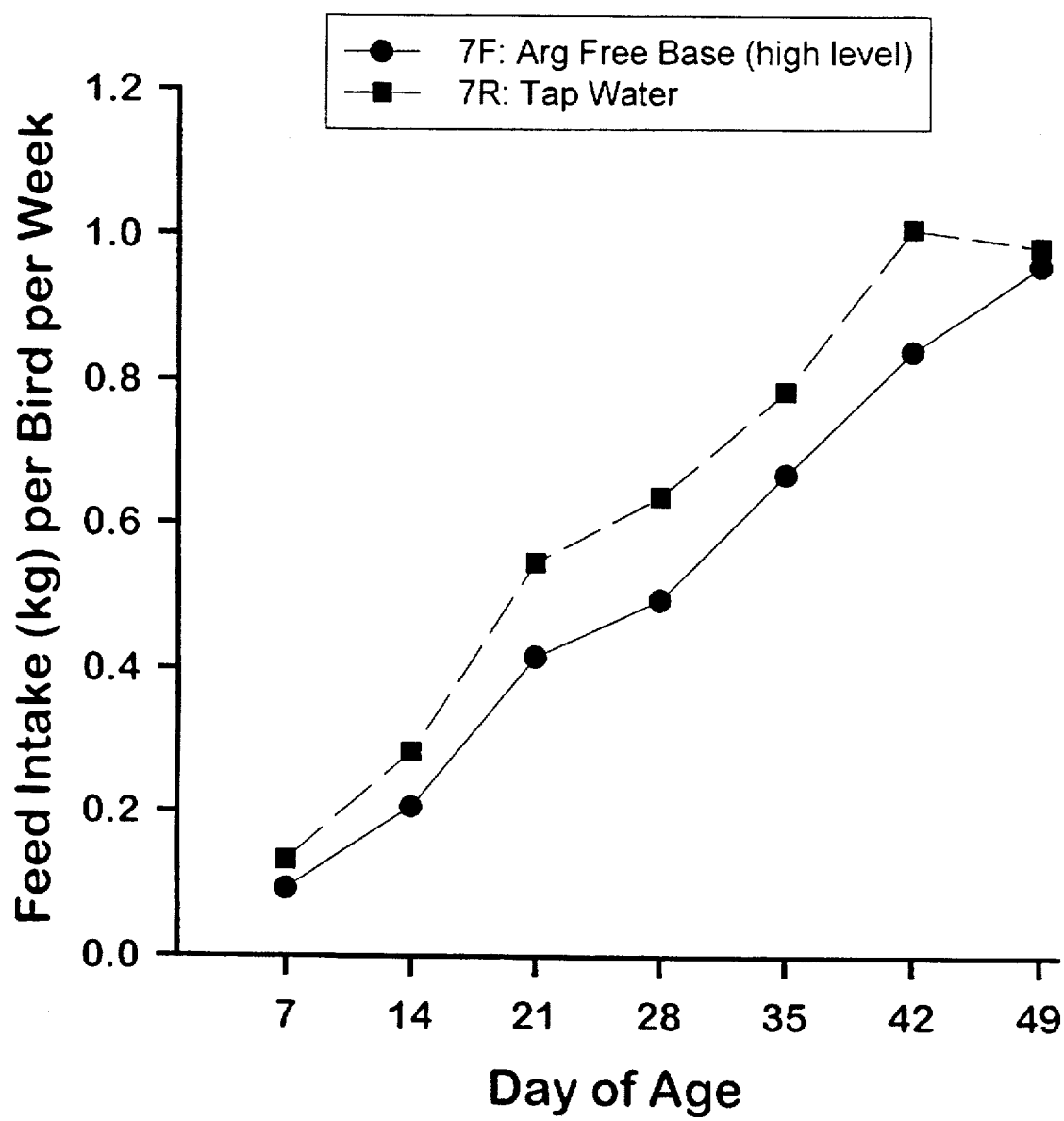
Figure 29:
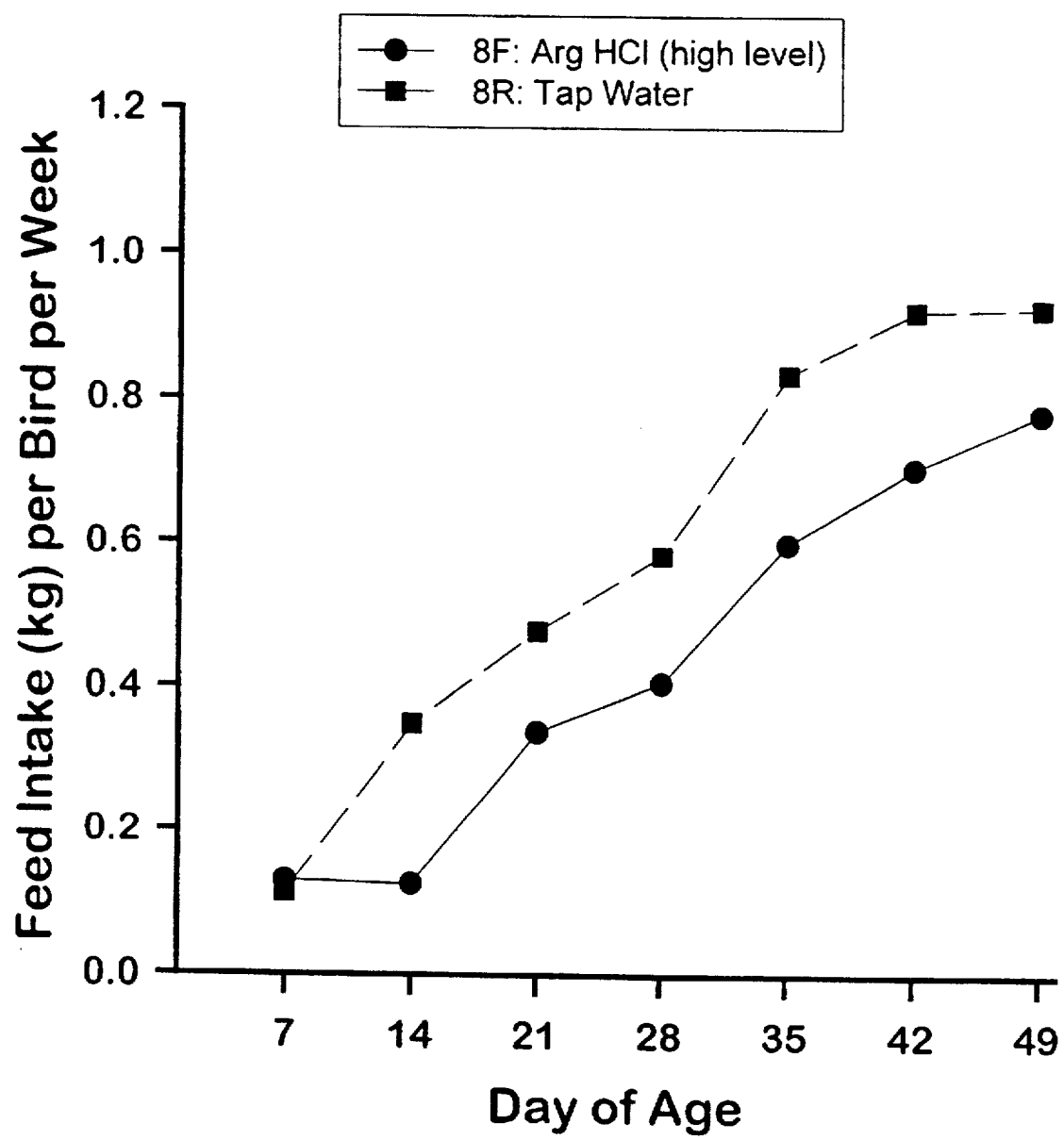
Figure 30:
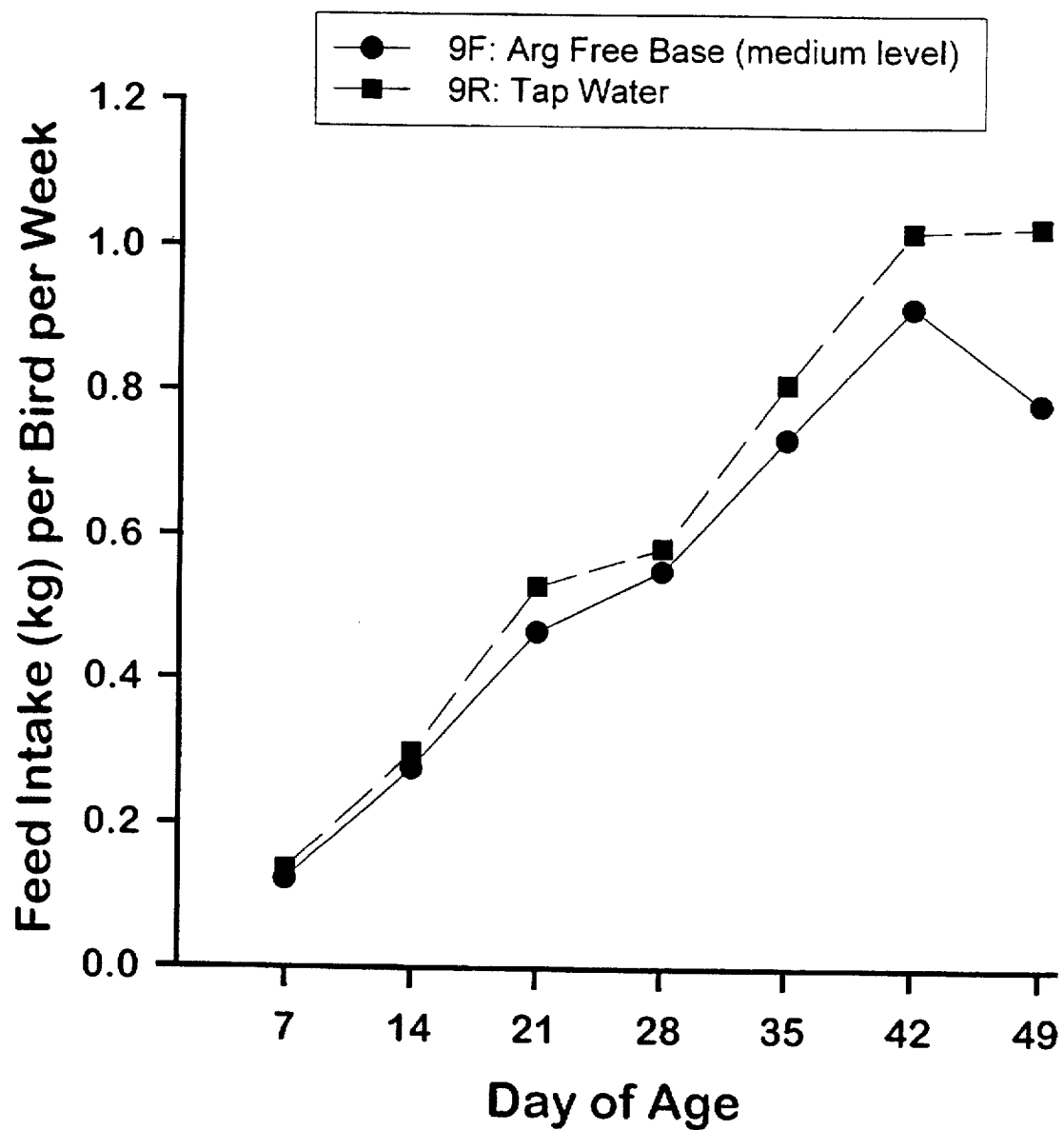
Figure 31:
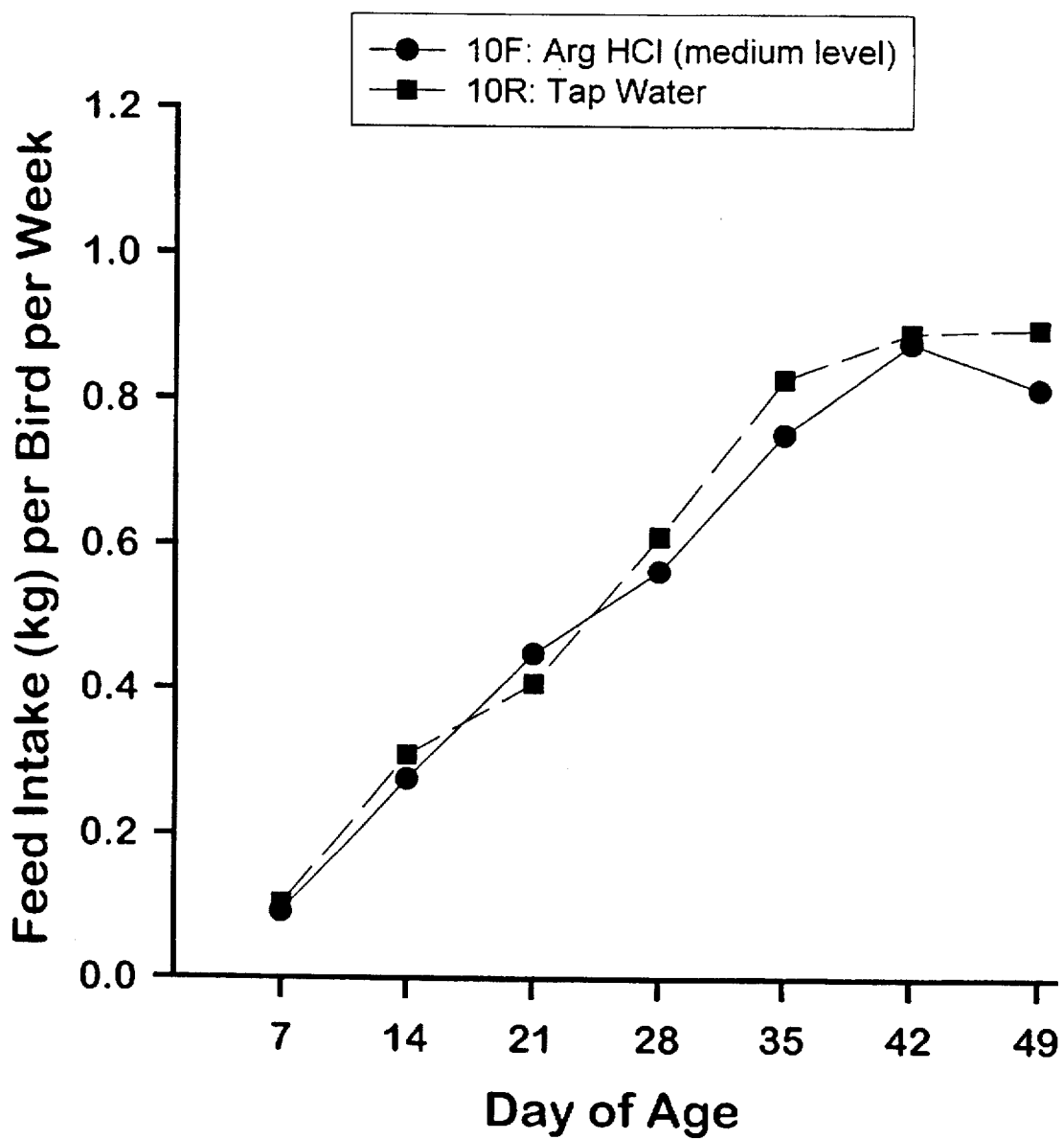
Figure 32:
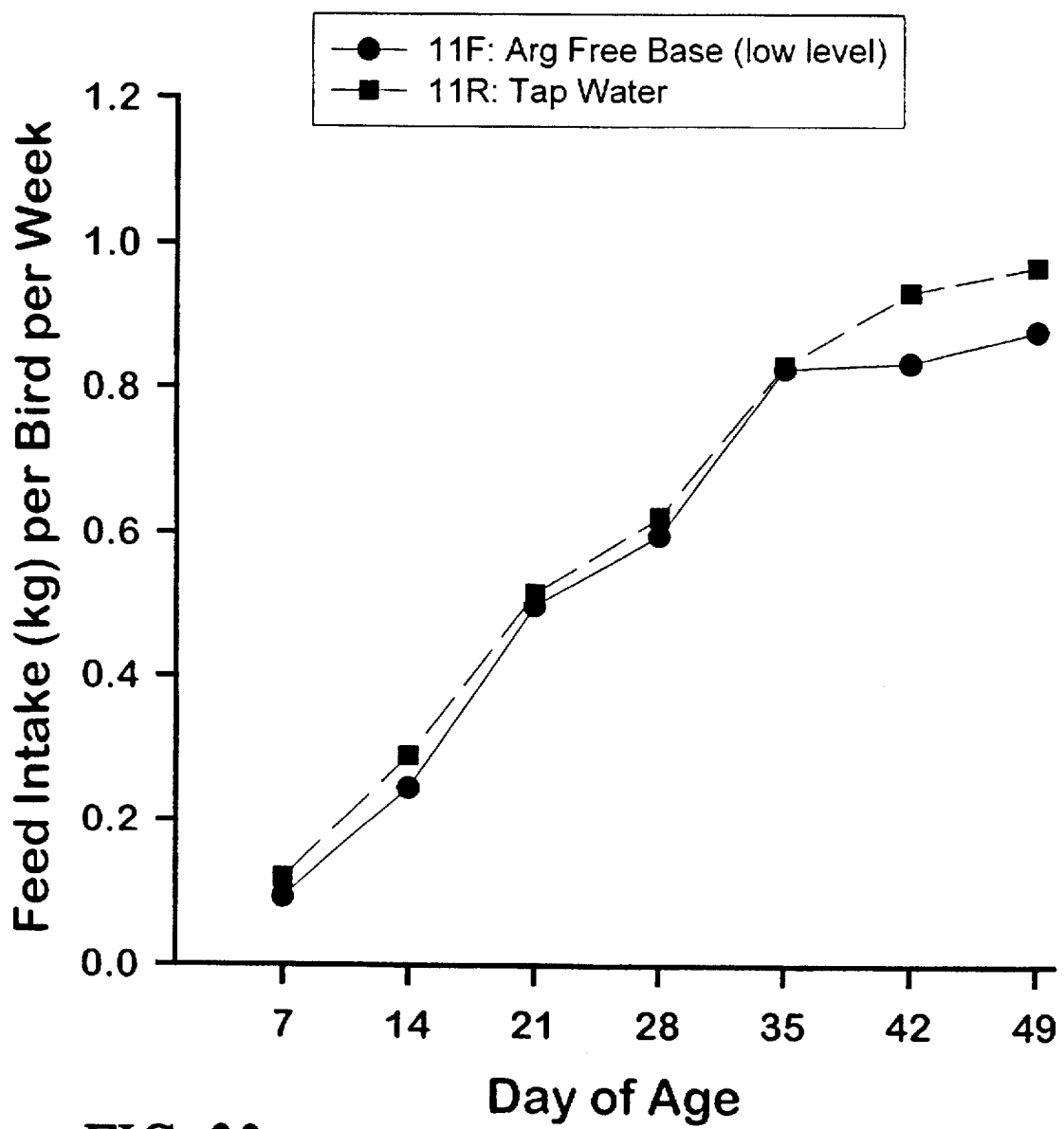
Figure 33:
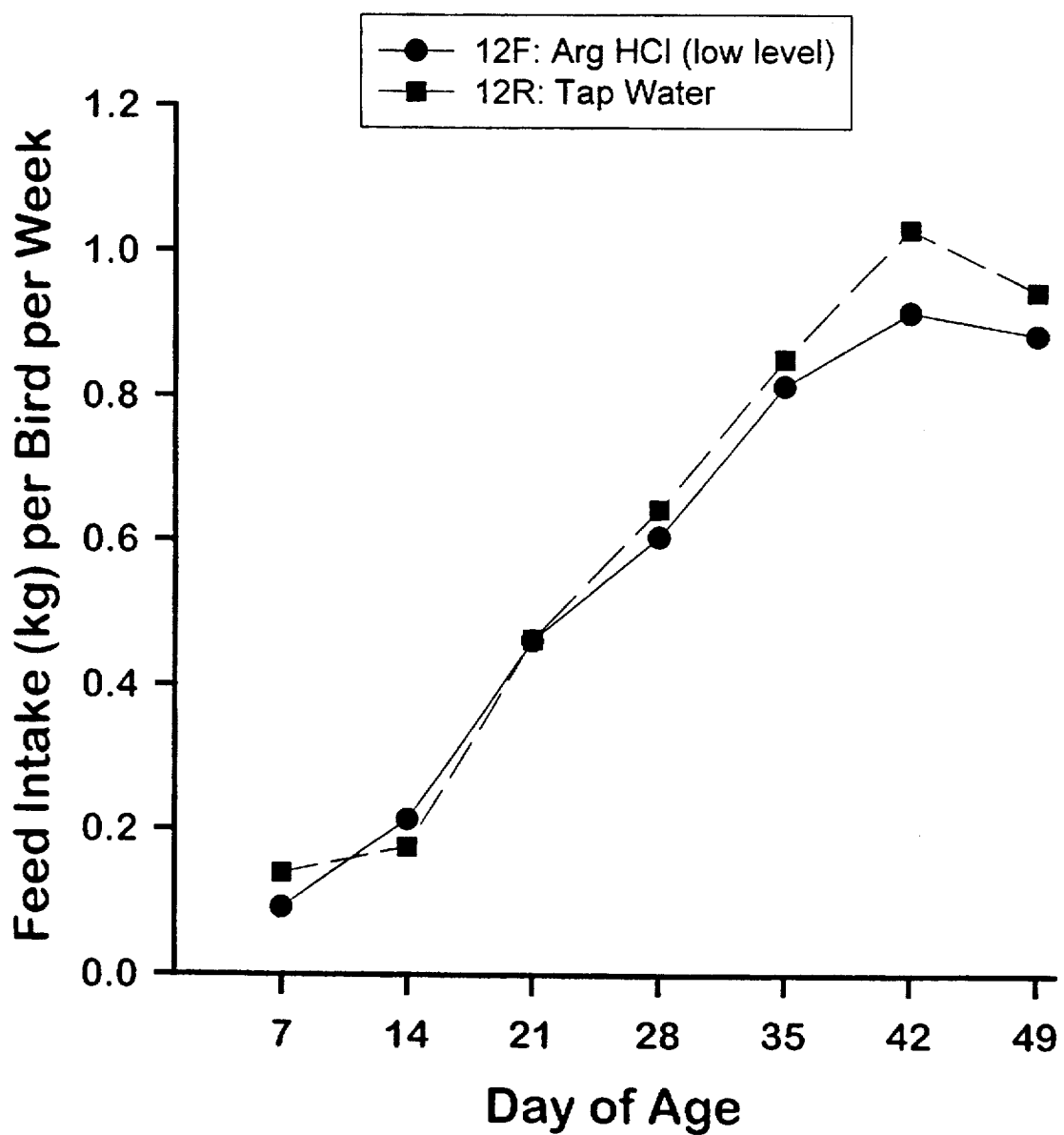
Figure 34:
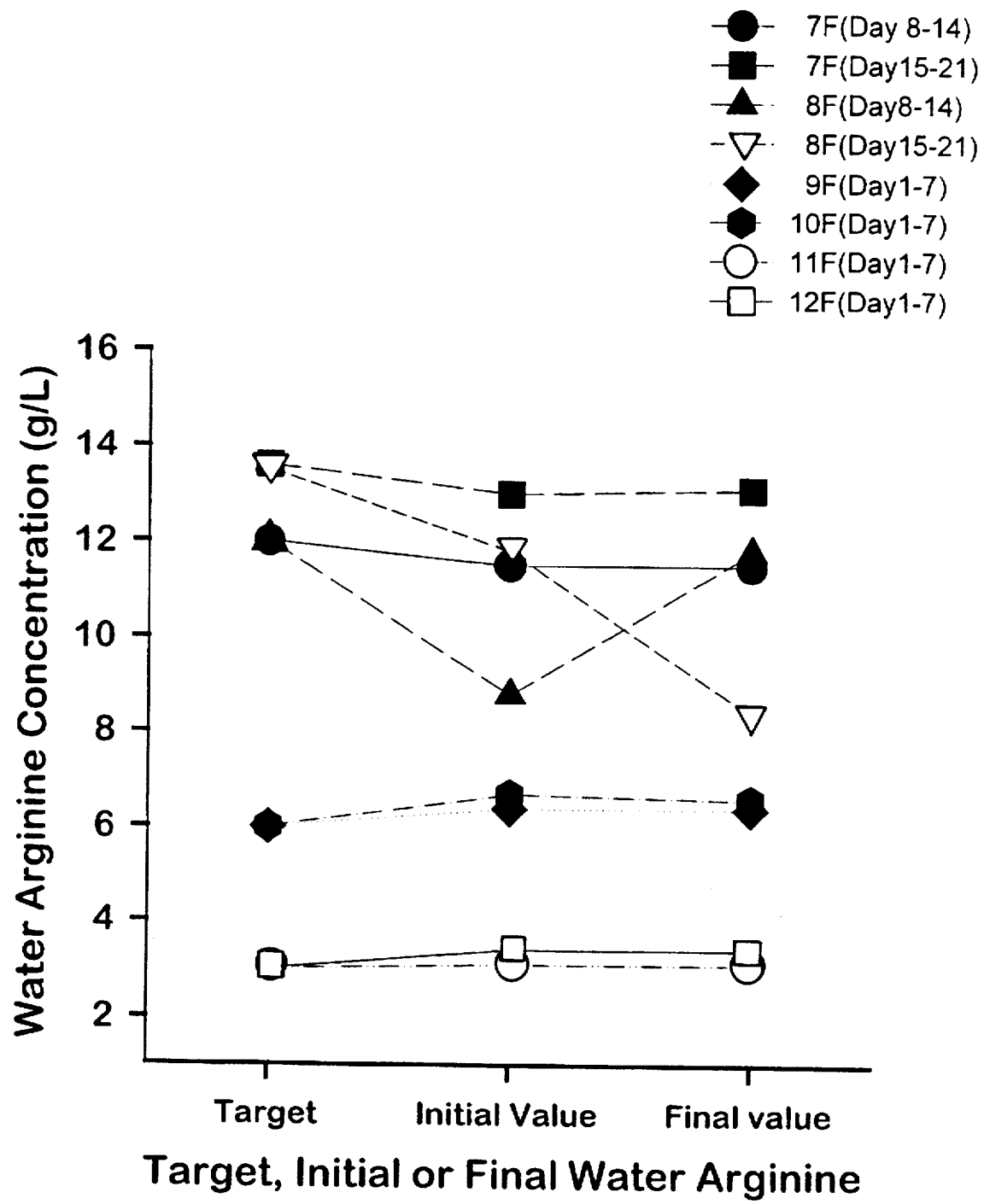
FIG. 34 Plot showing Water Arginine Concentration compared to the Target, Initial and Final water Arginine value for example 1.
Figure 35:
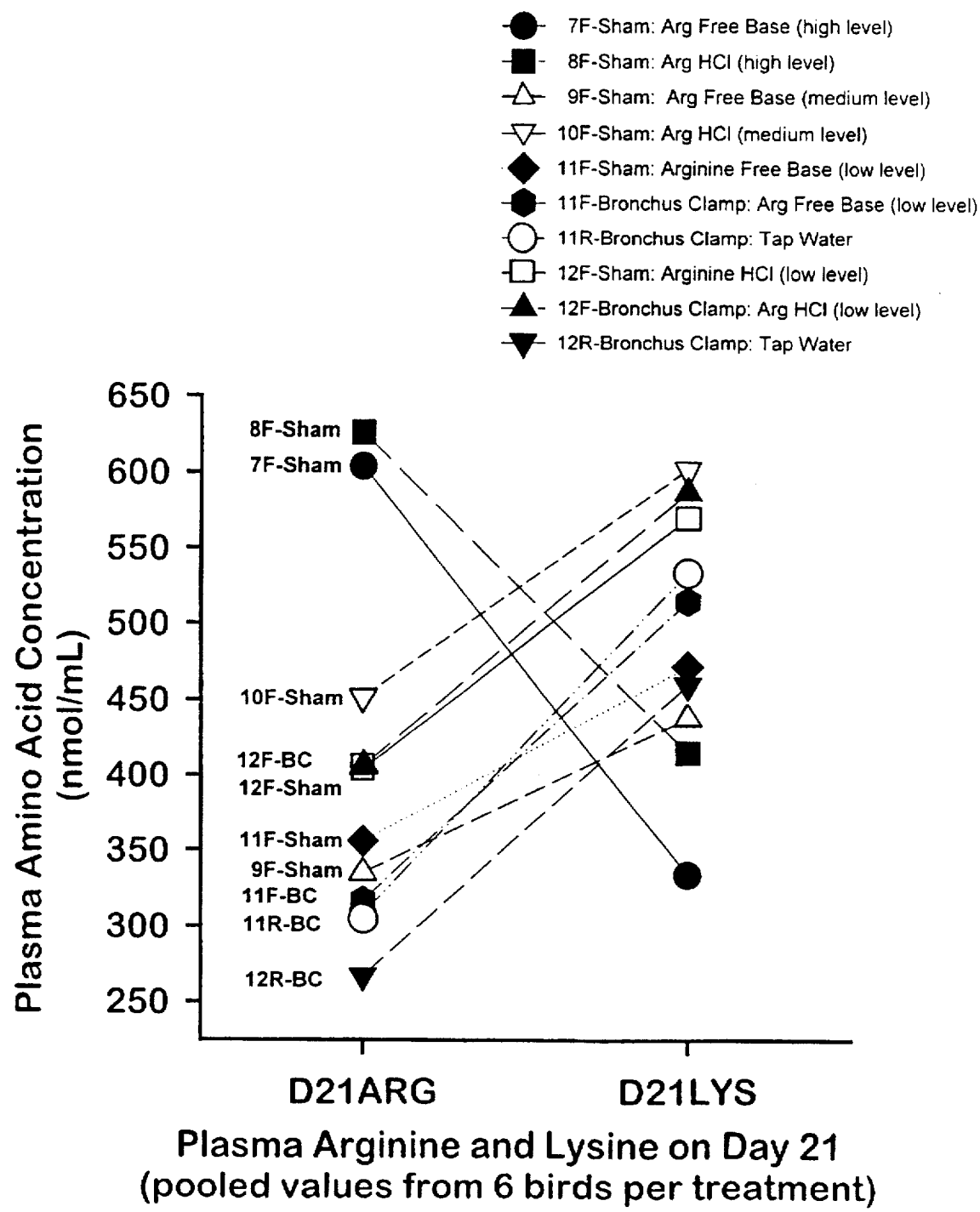
FIGS. 35–36 Plasma amino acid concentration plotted against Plasma Arginine and Lysine on Day 21, and Day 49 for example 1.
Figure 36:
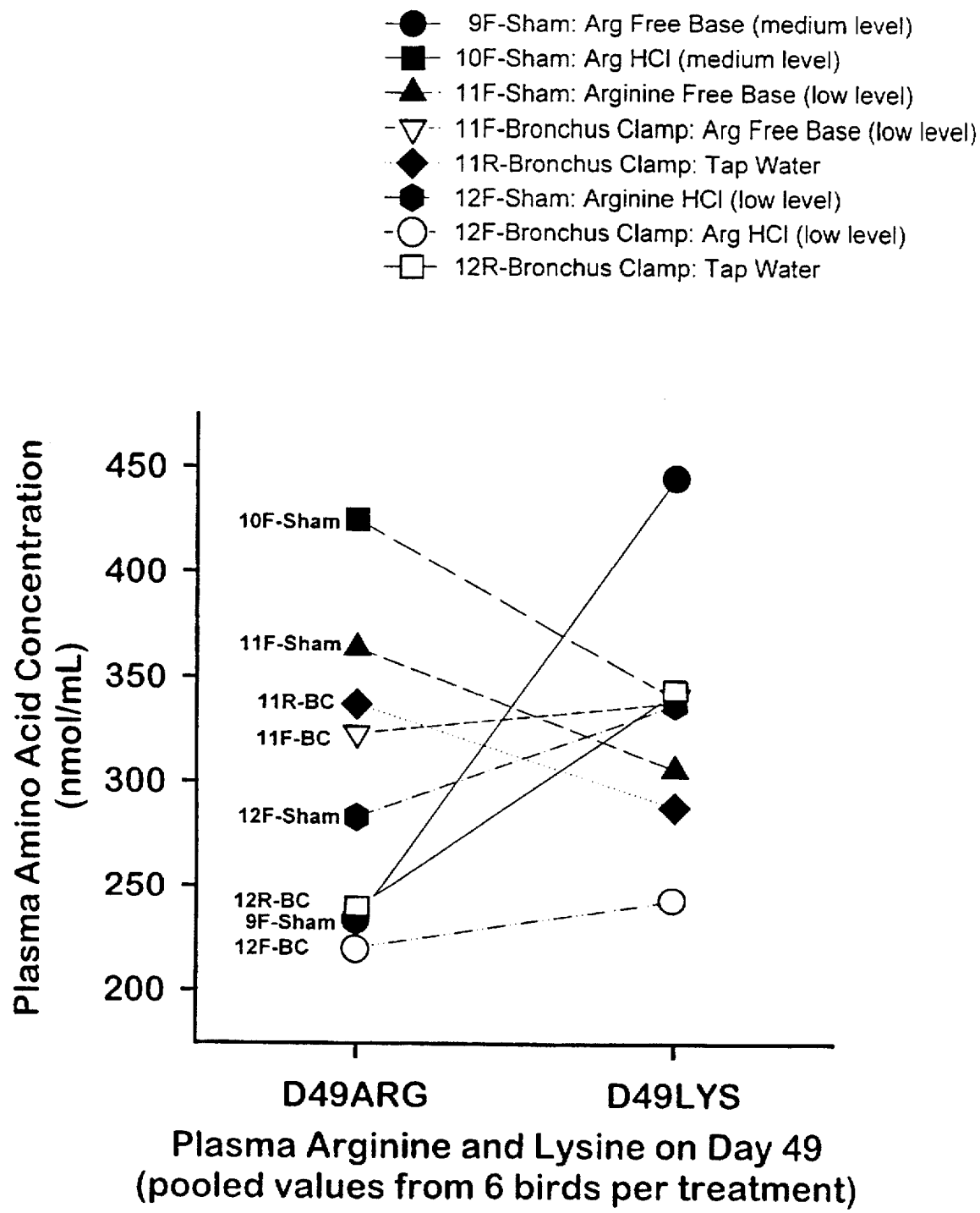
Figure 37:
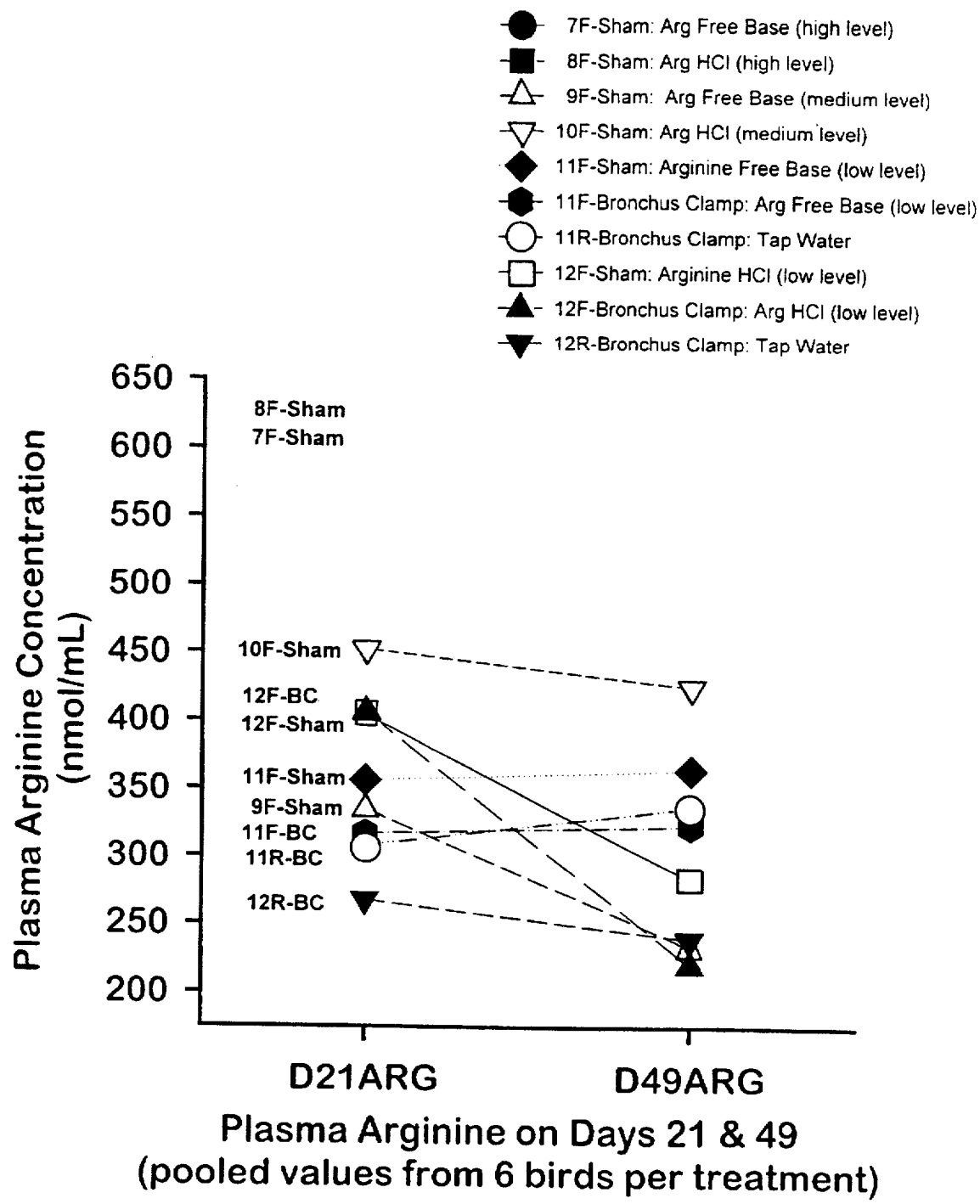
FIG. 37 Plasma Arginine concentration plotted against plasma arginine on days 21 and 49.
Figure 38:
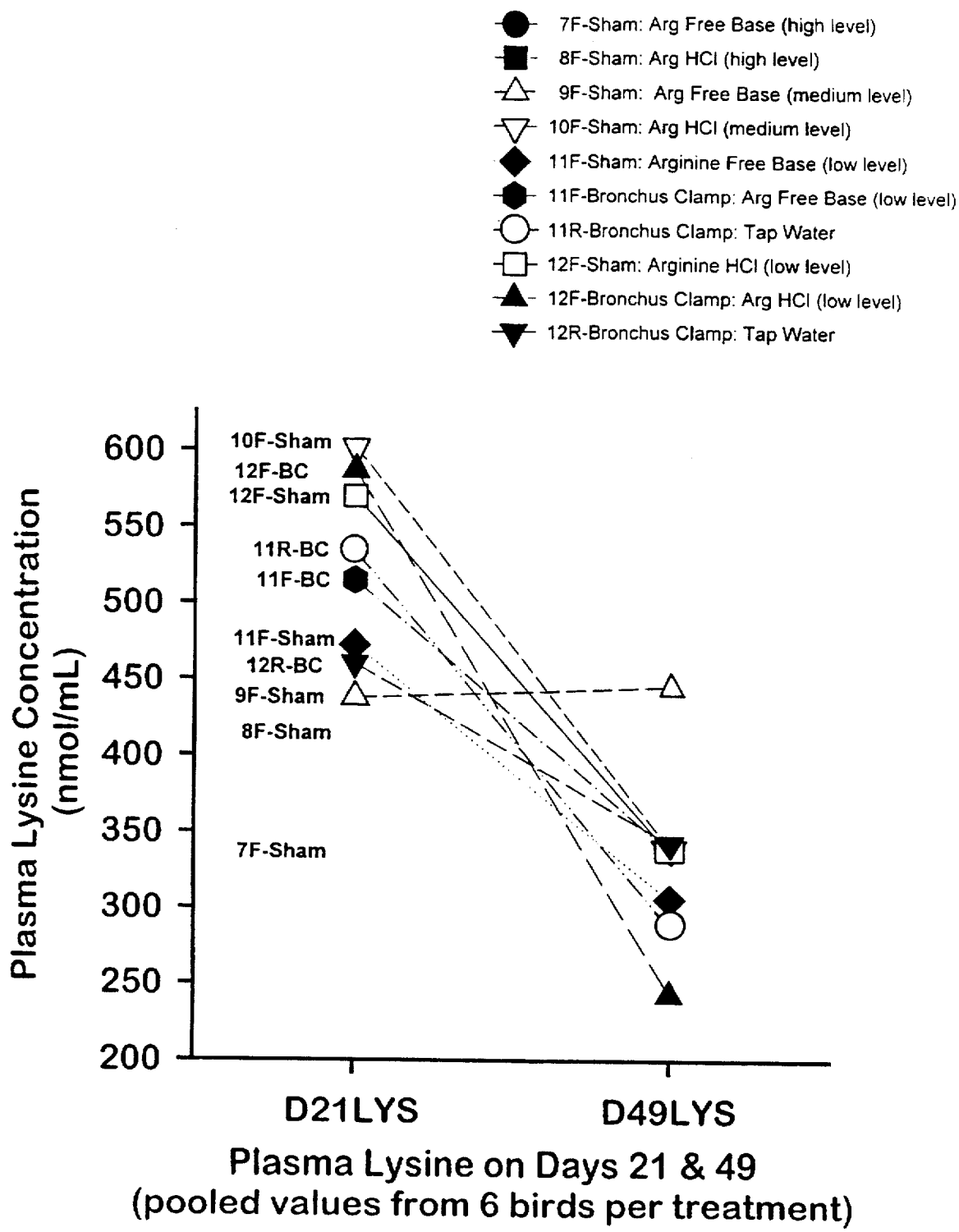
FIG. 38 Plasma Lysine concentration plotted against plasma lysine on days 21 and 49.
Figure 40:
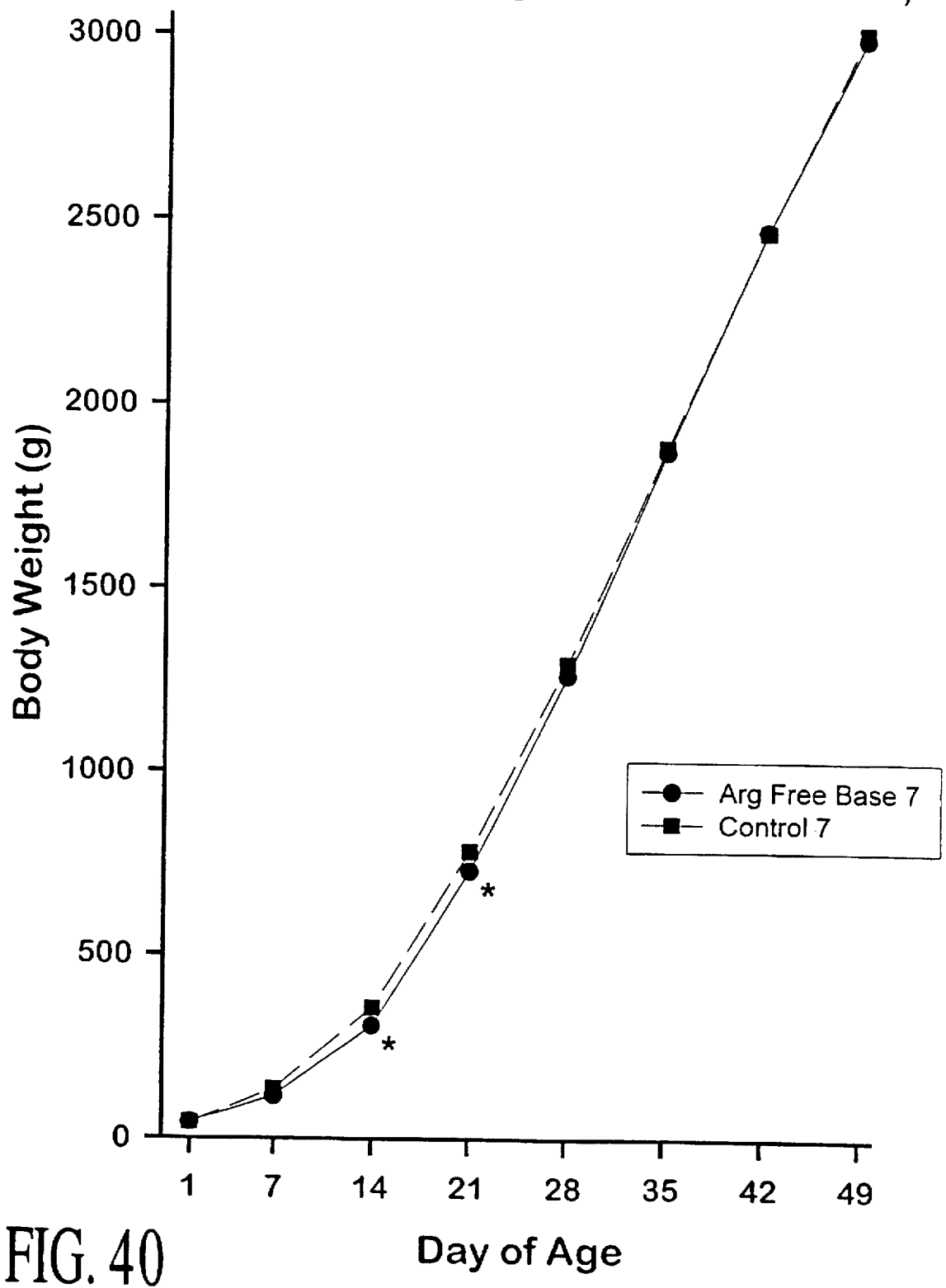
FIGS. 40–50 Growth curves for example 2.
Figure 41:
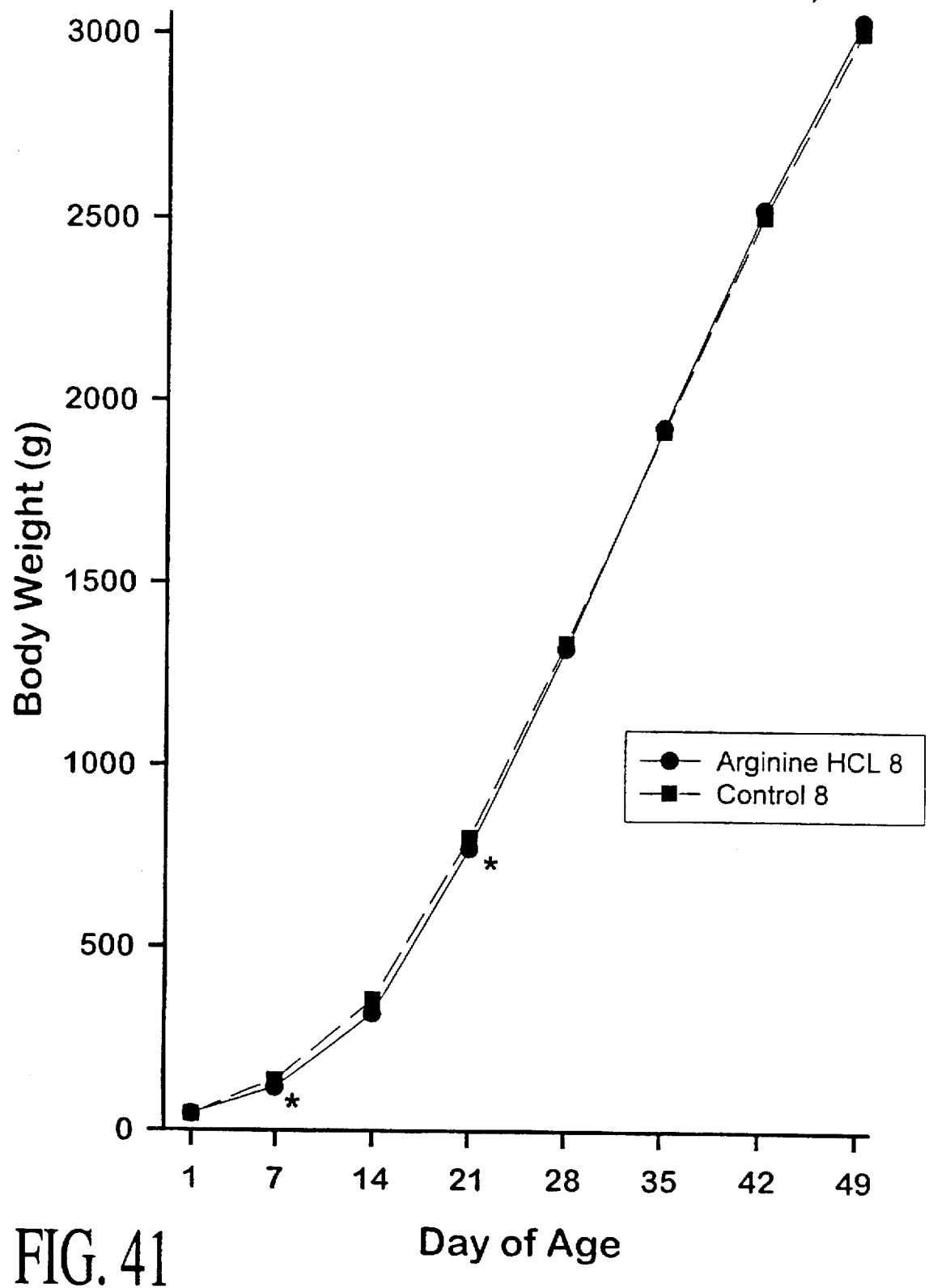
Figure 42:
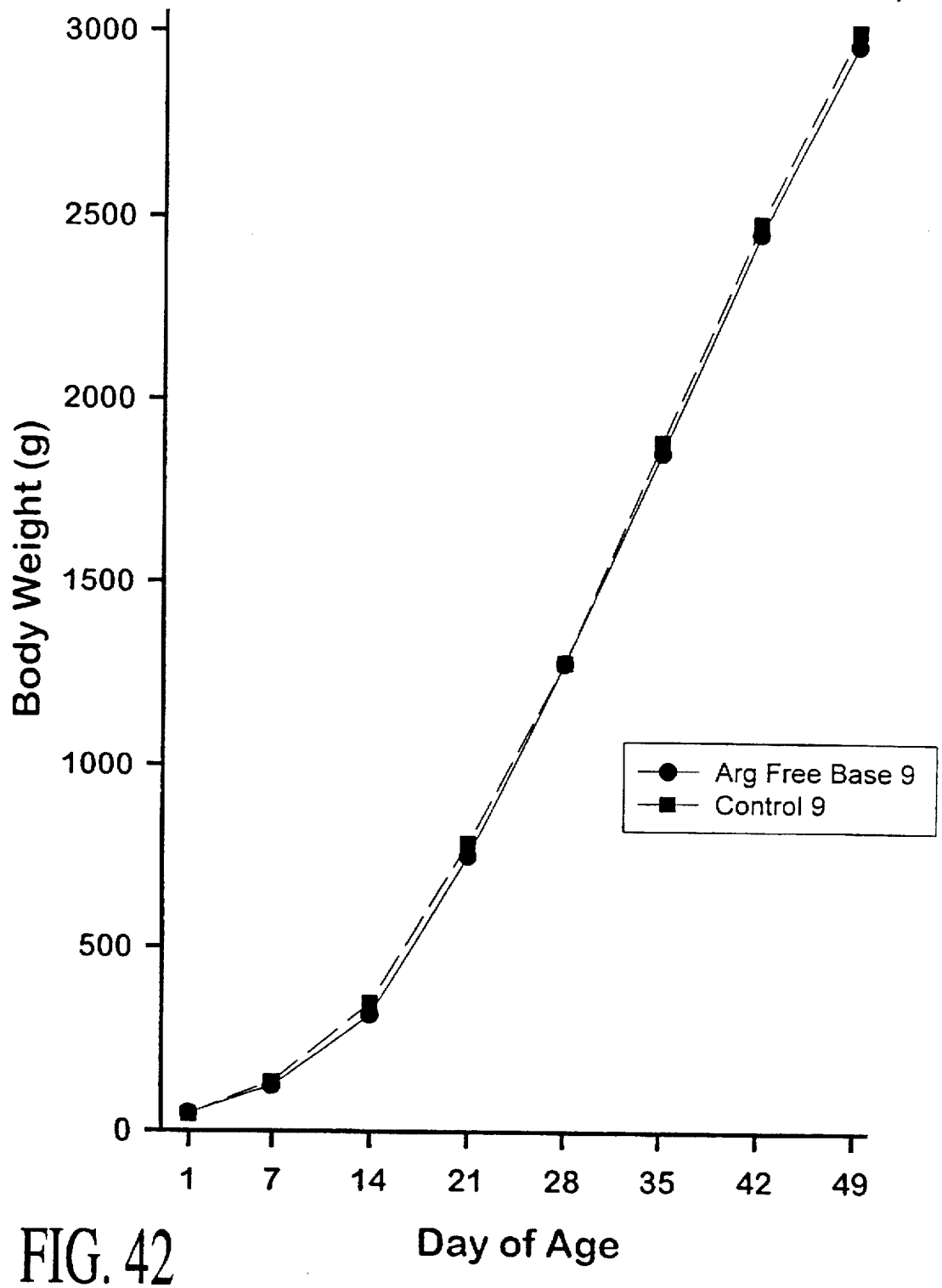
Figure 43:
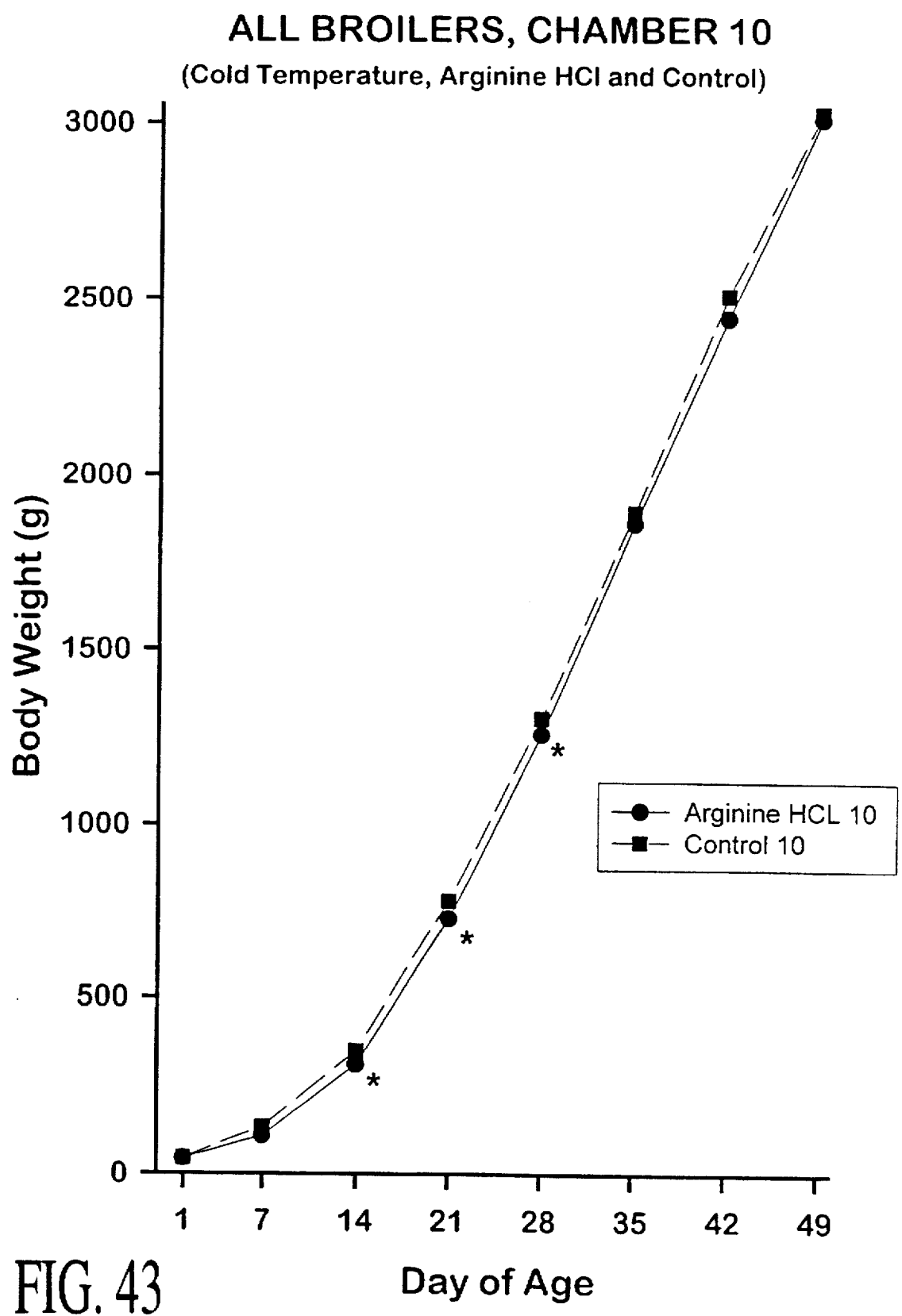
Figure 44:
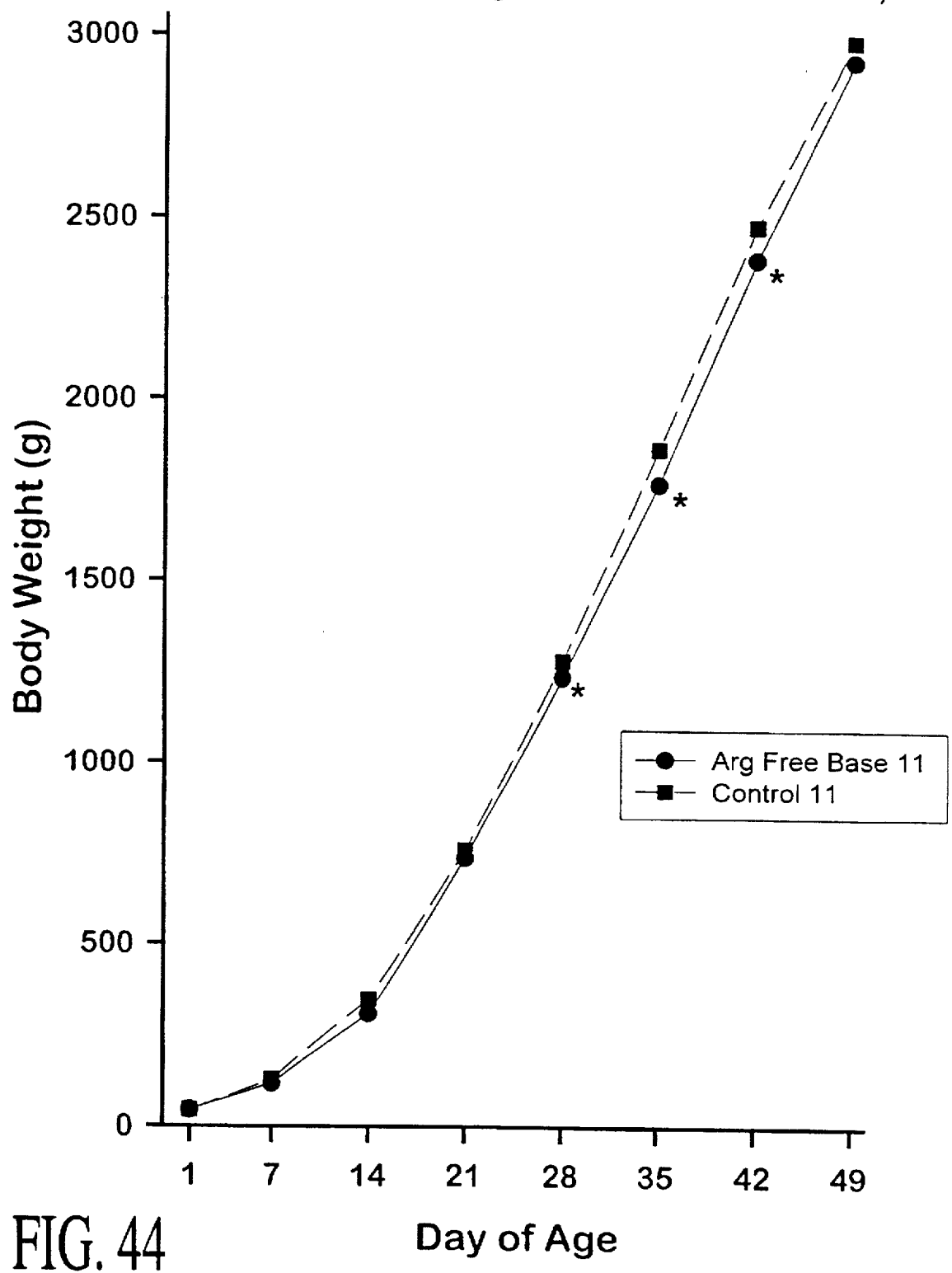
Figure 45:
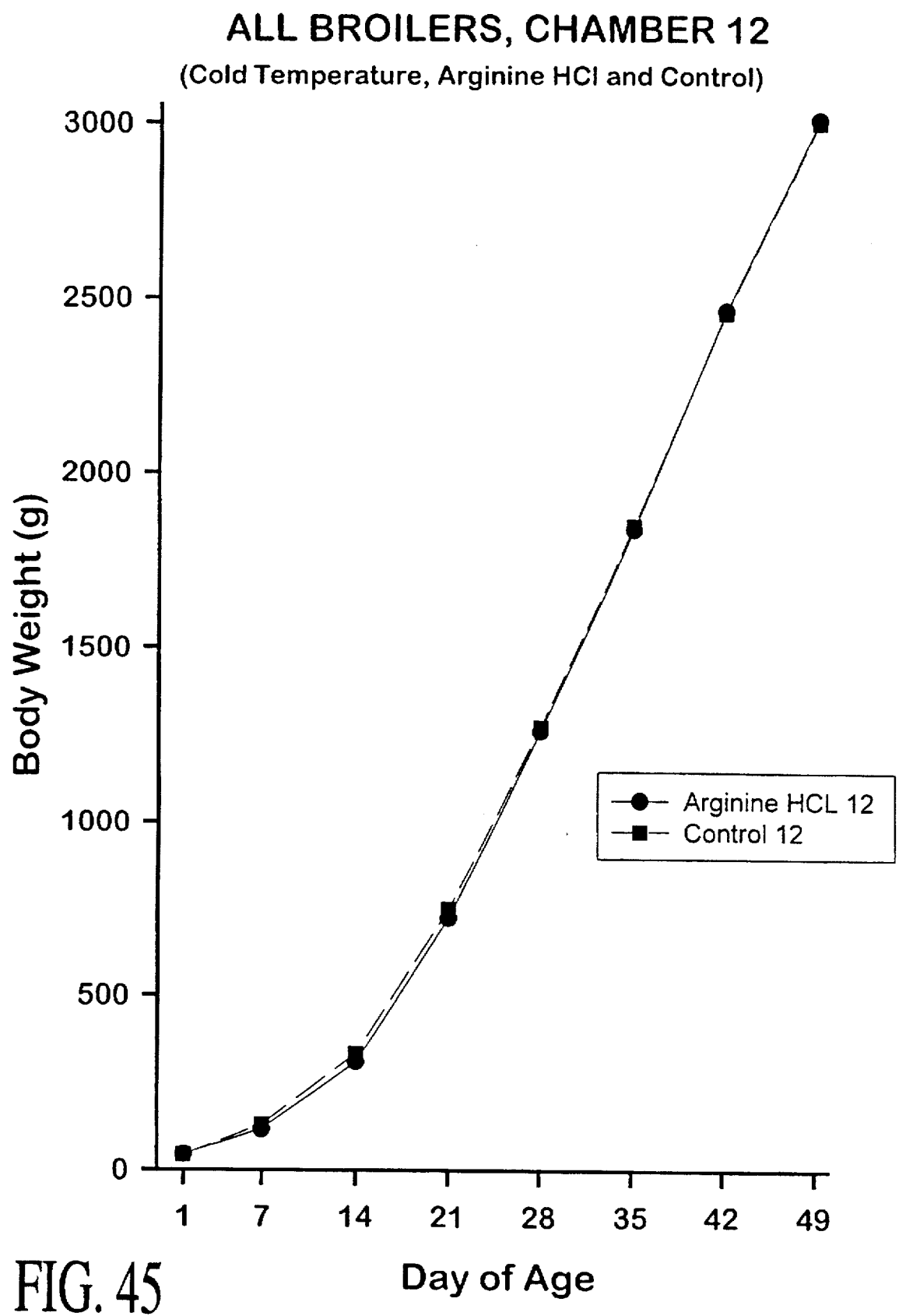
Figure 46:
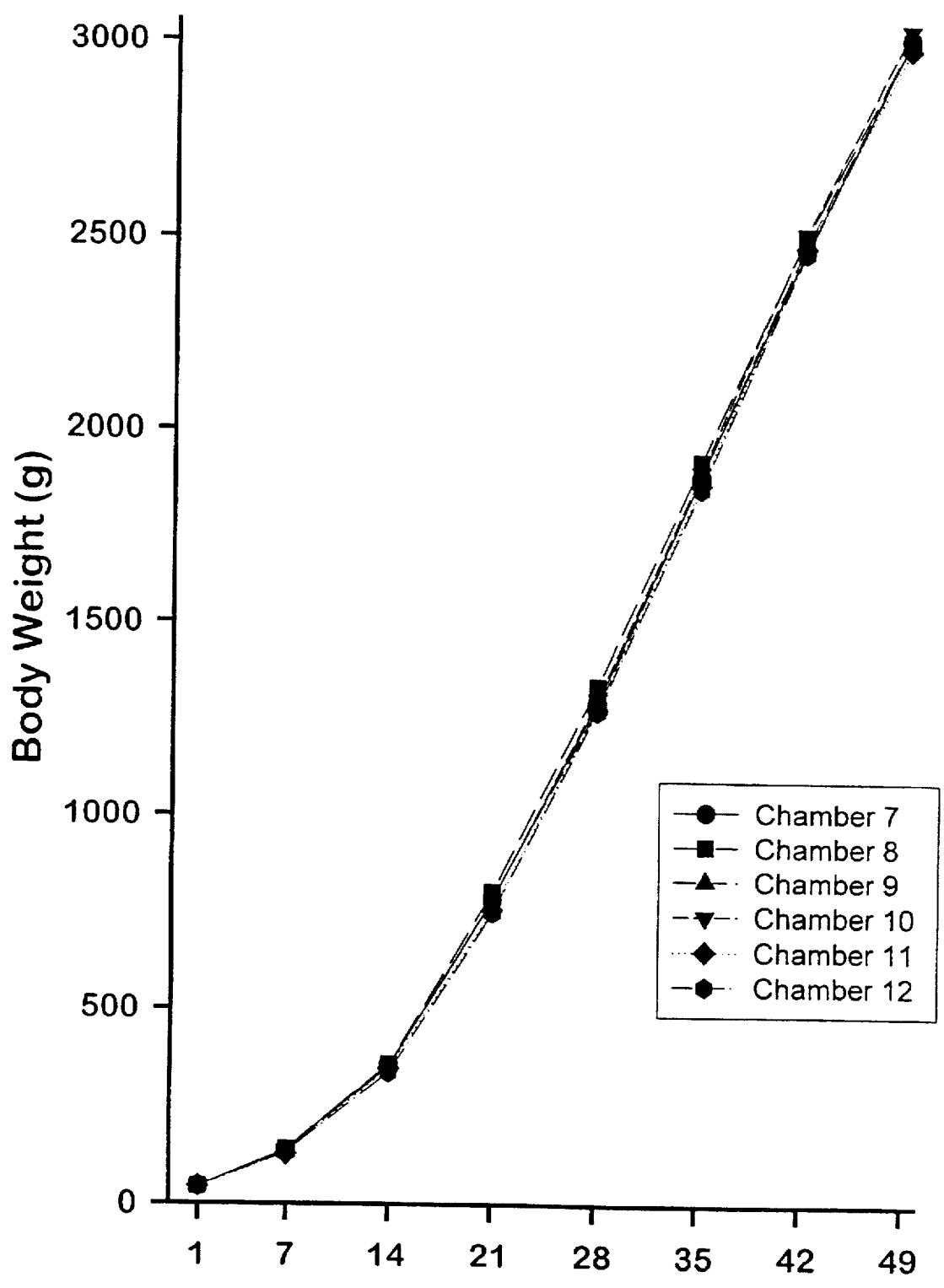
Figure 47:
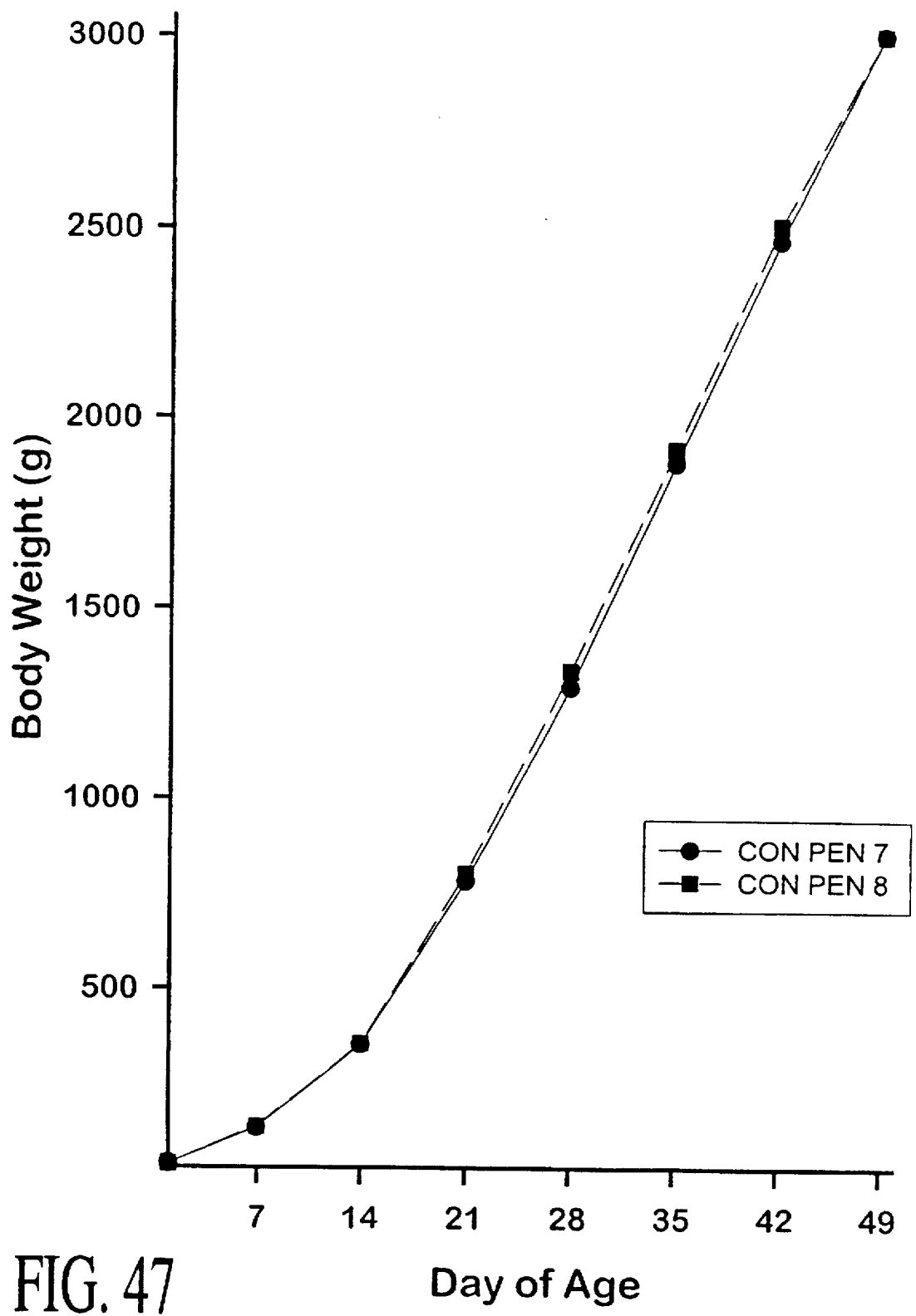
Figure 48:
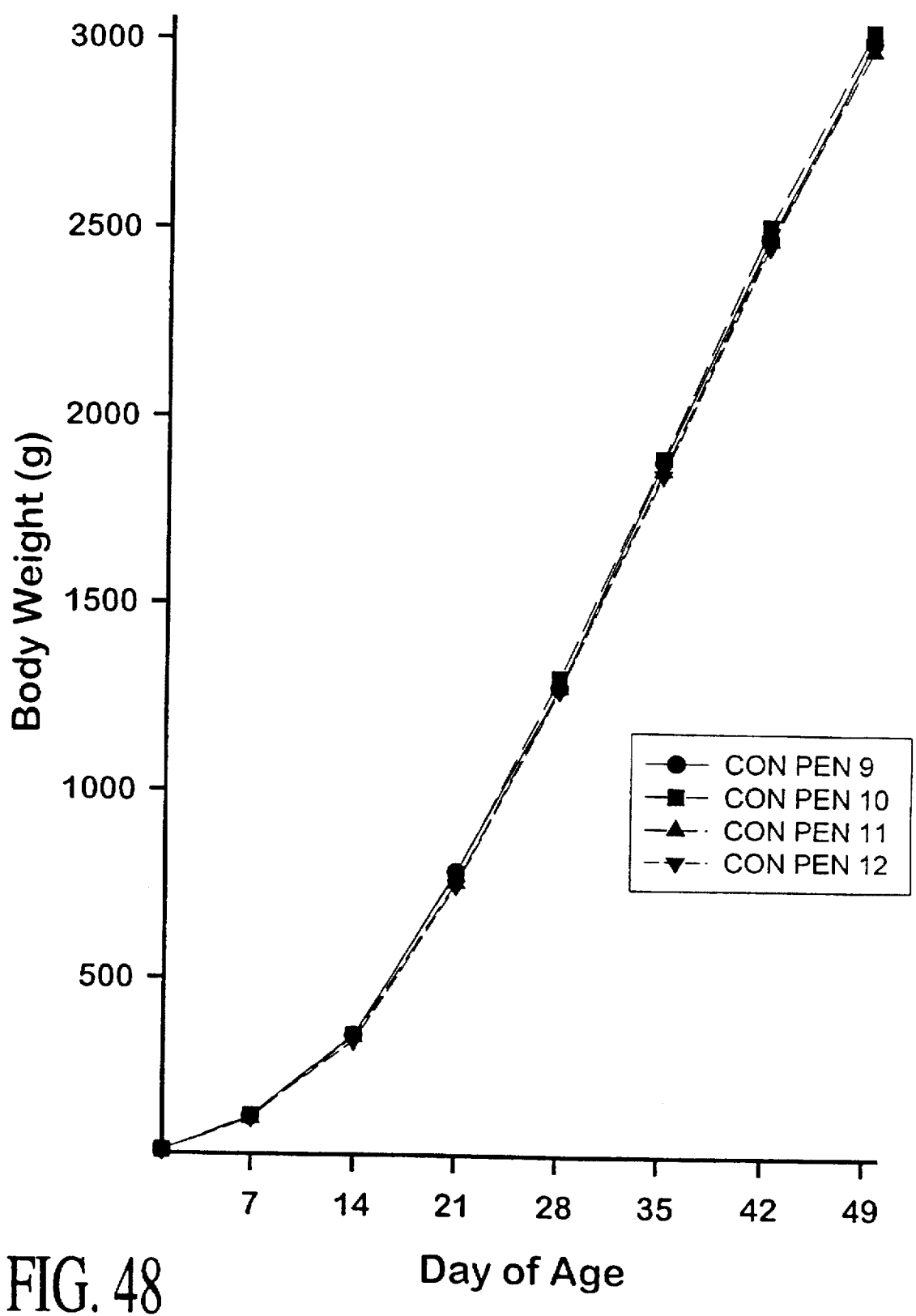
Figure 49:
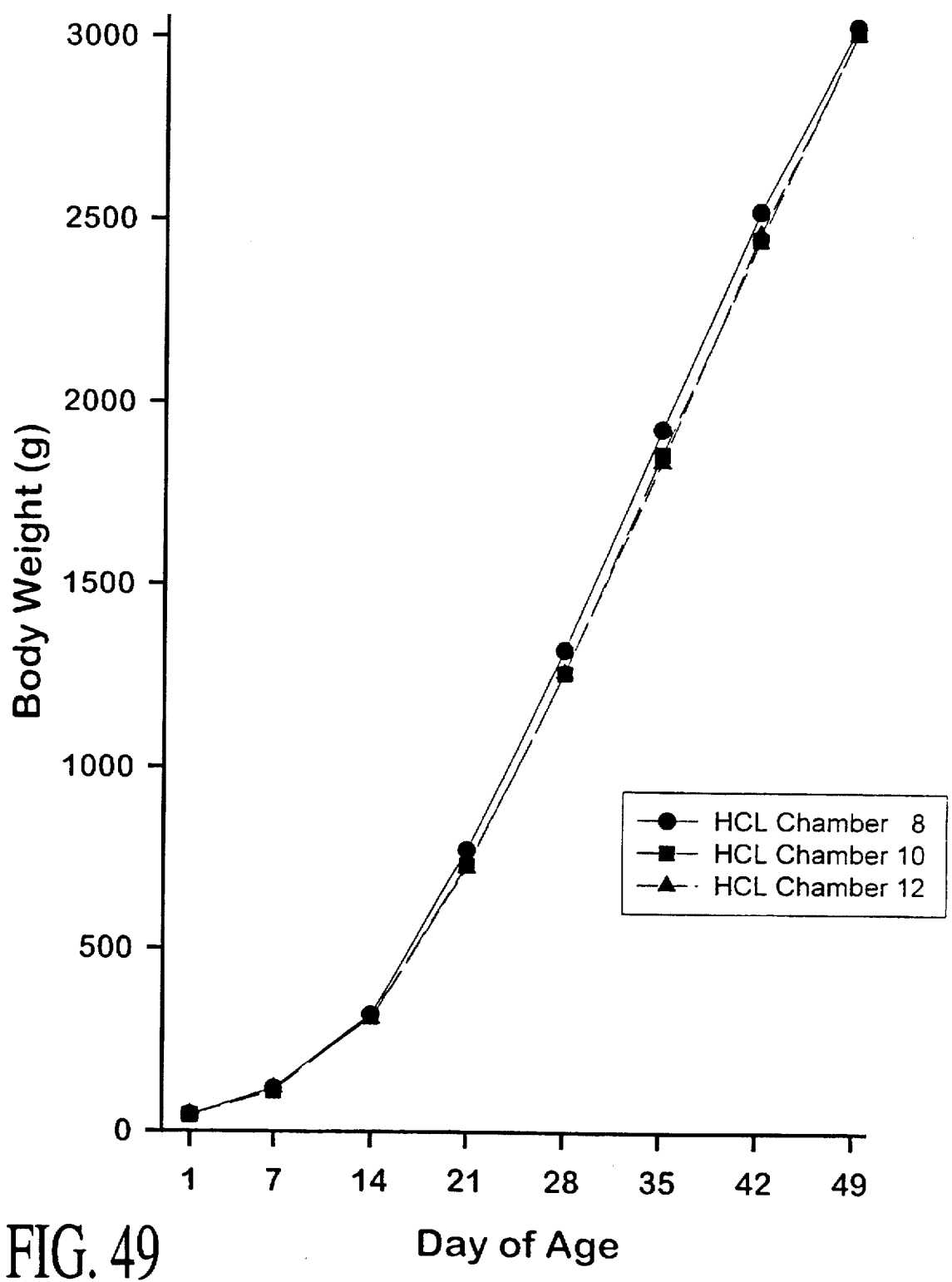
Figure 50:
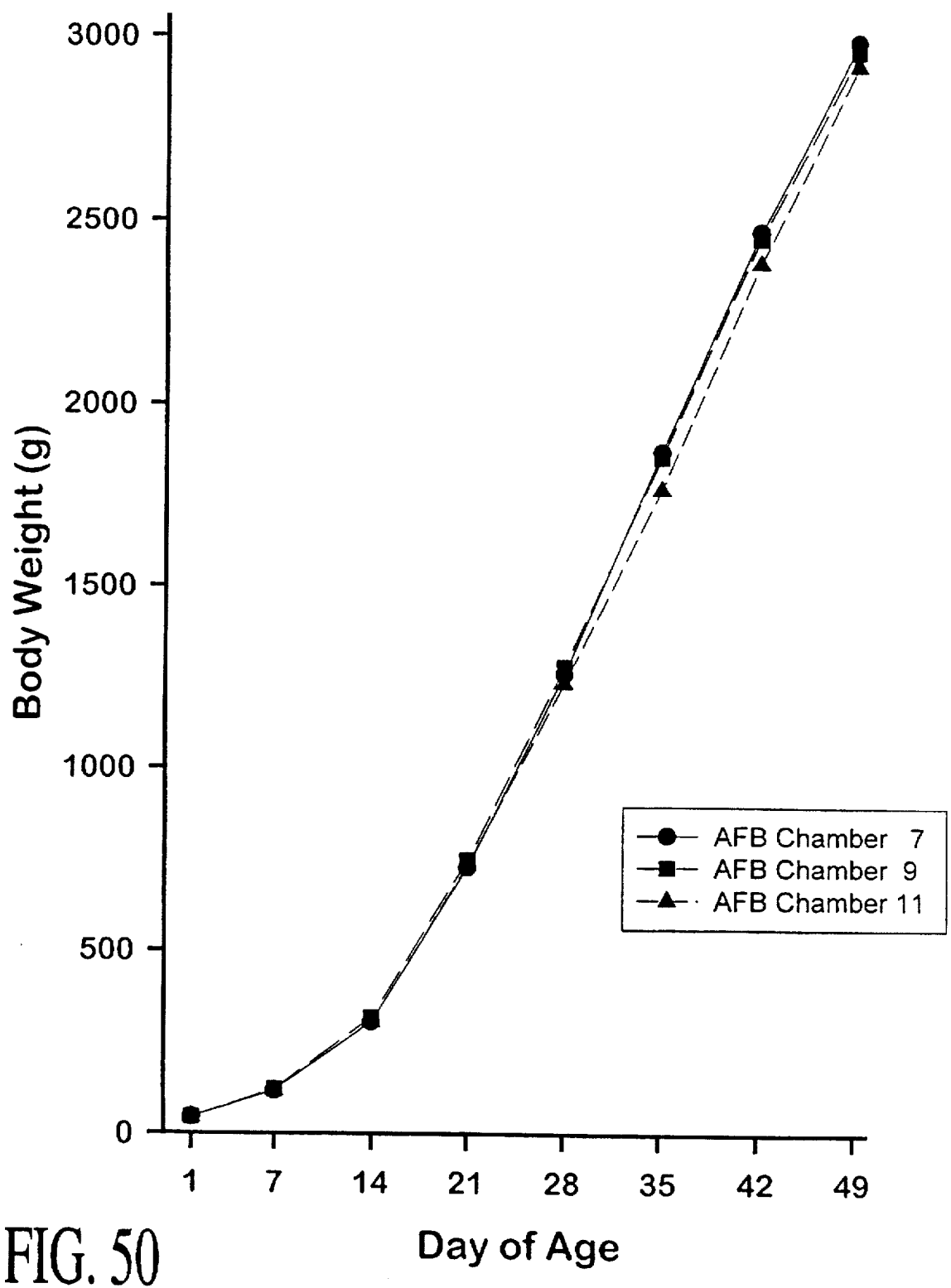
Figure 51:
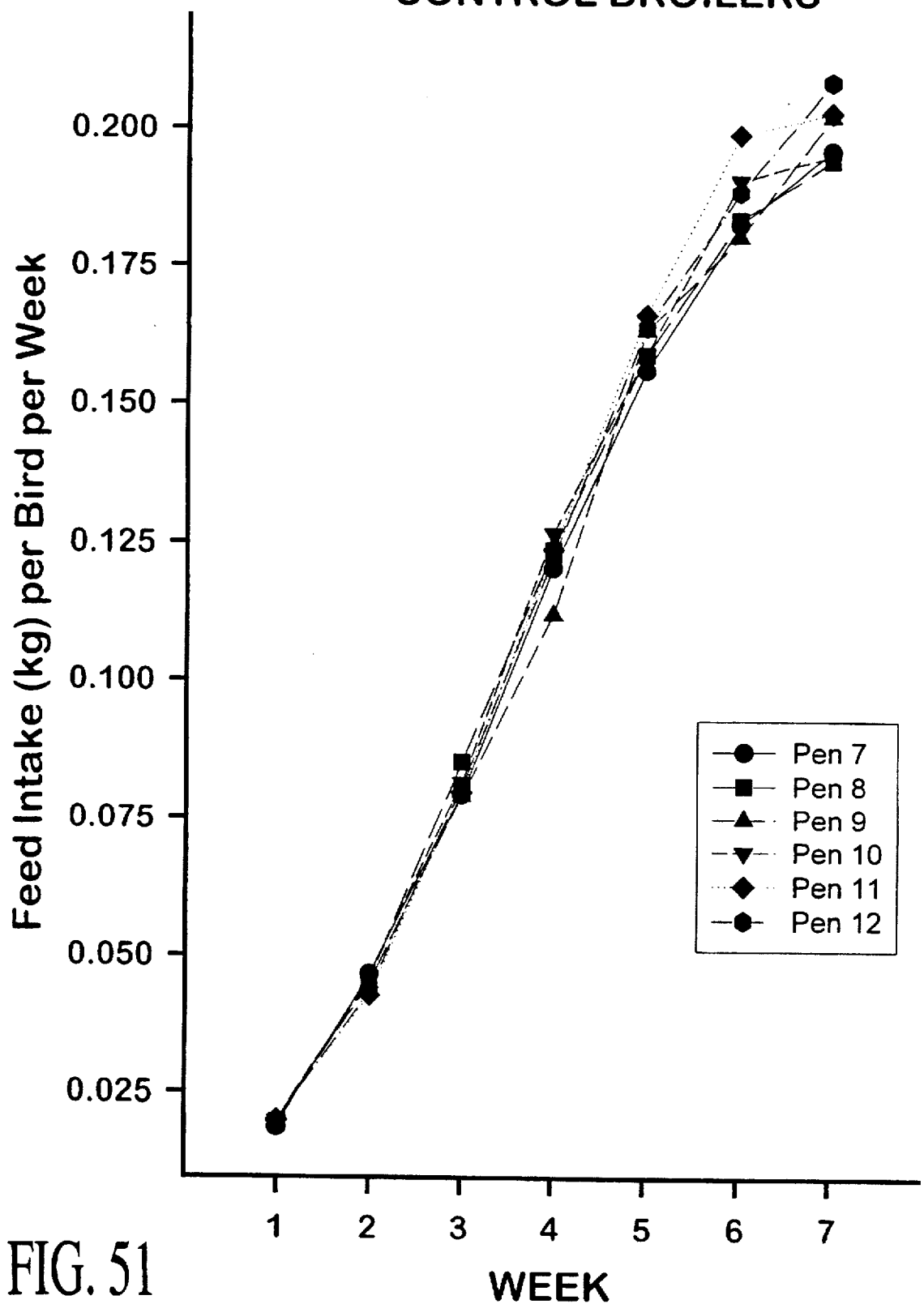
FIGS. 51–58 Feed intake Curves for example 2.
Figure 52:
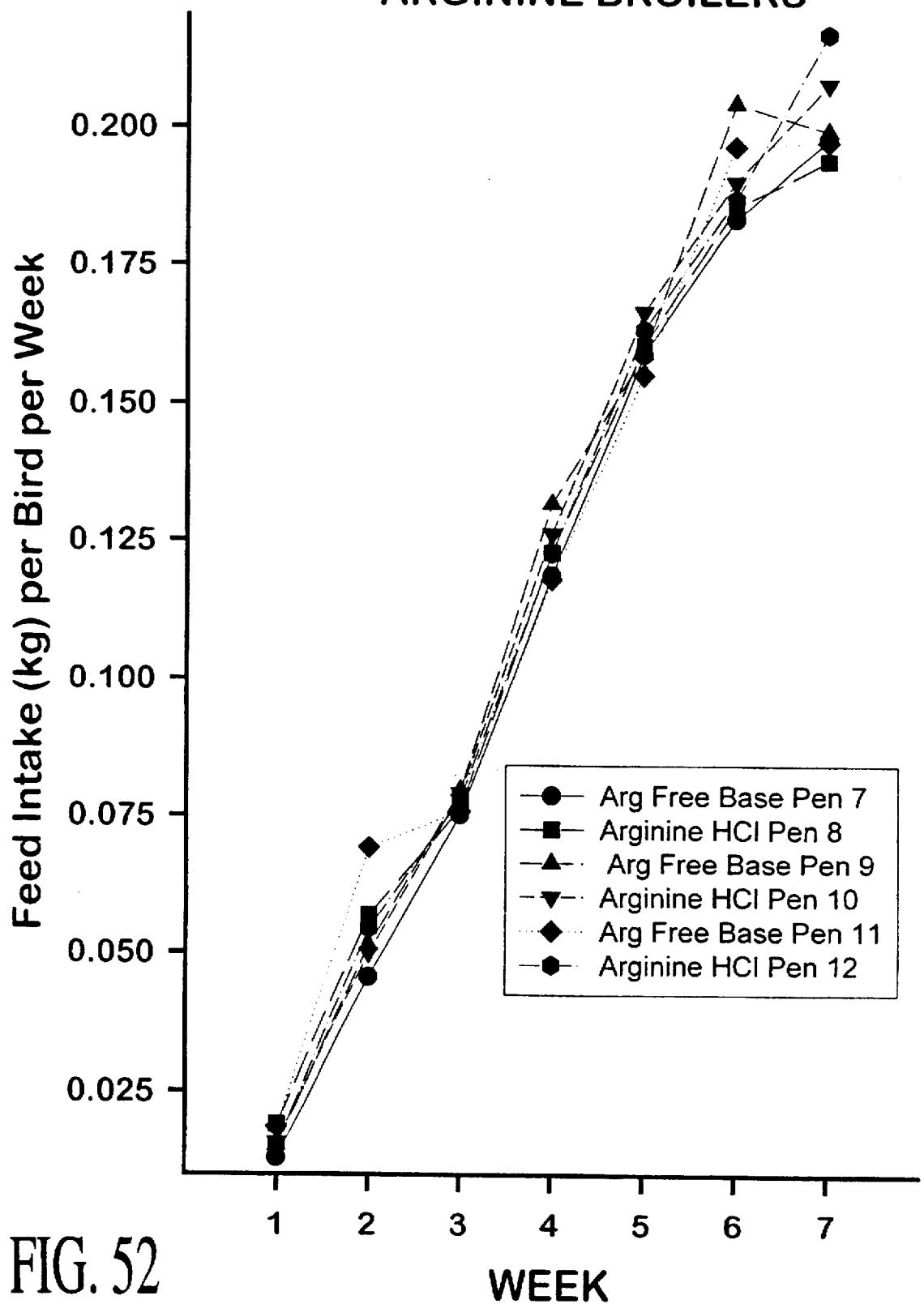
Figure 53:
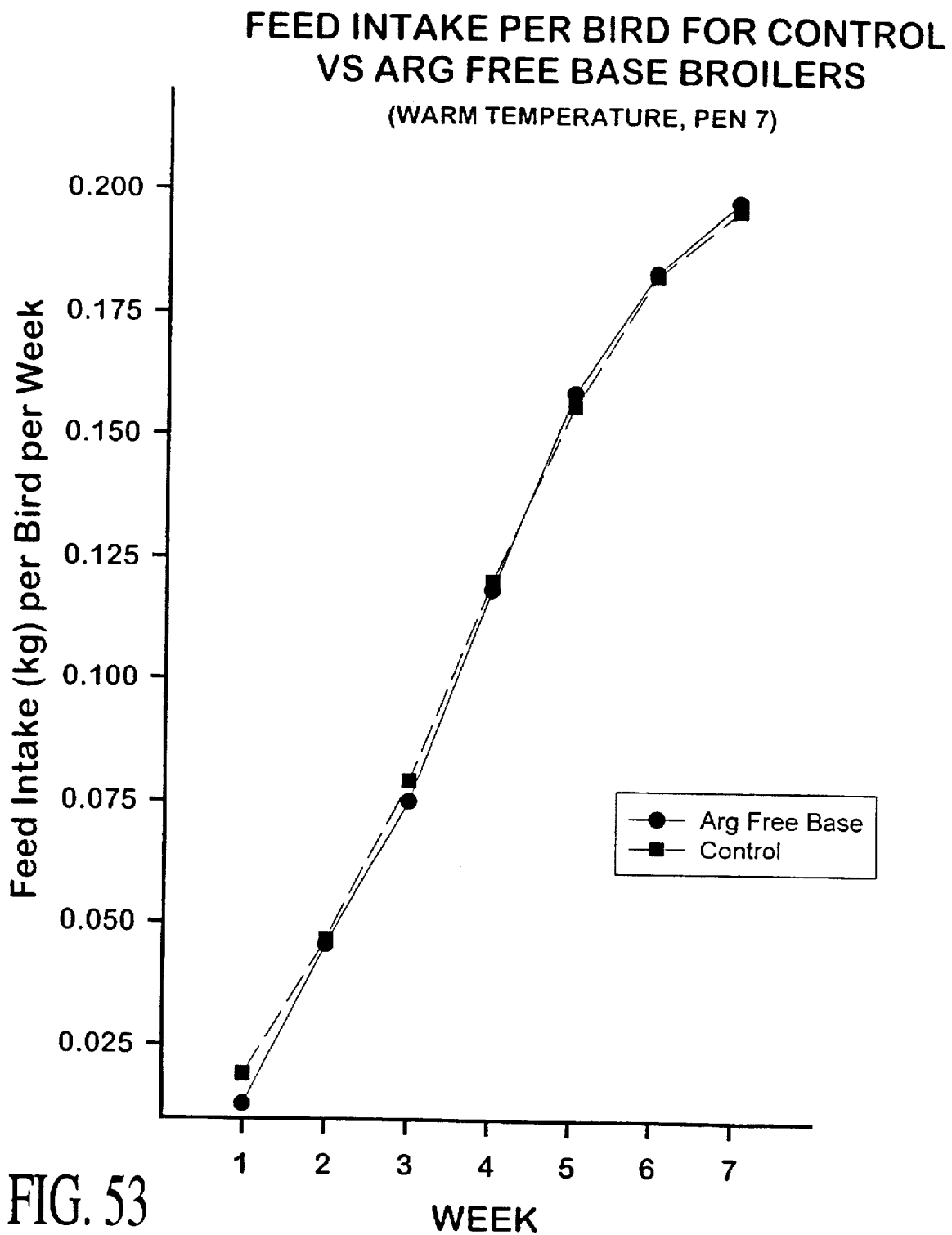
Figure 54:
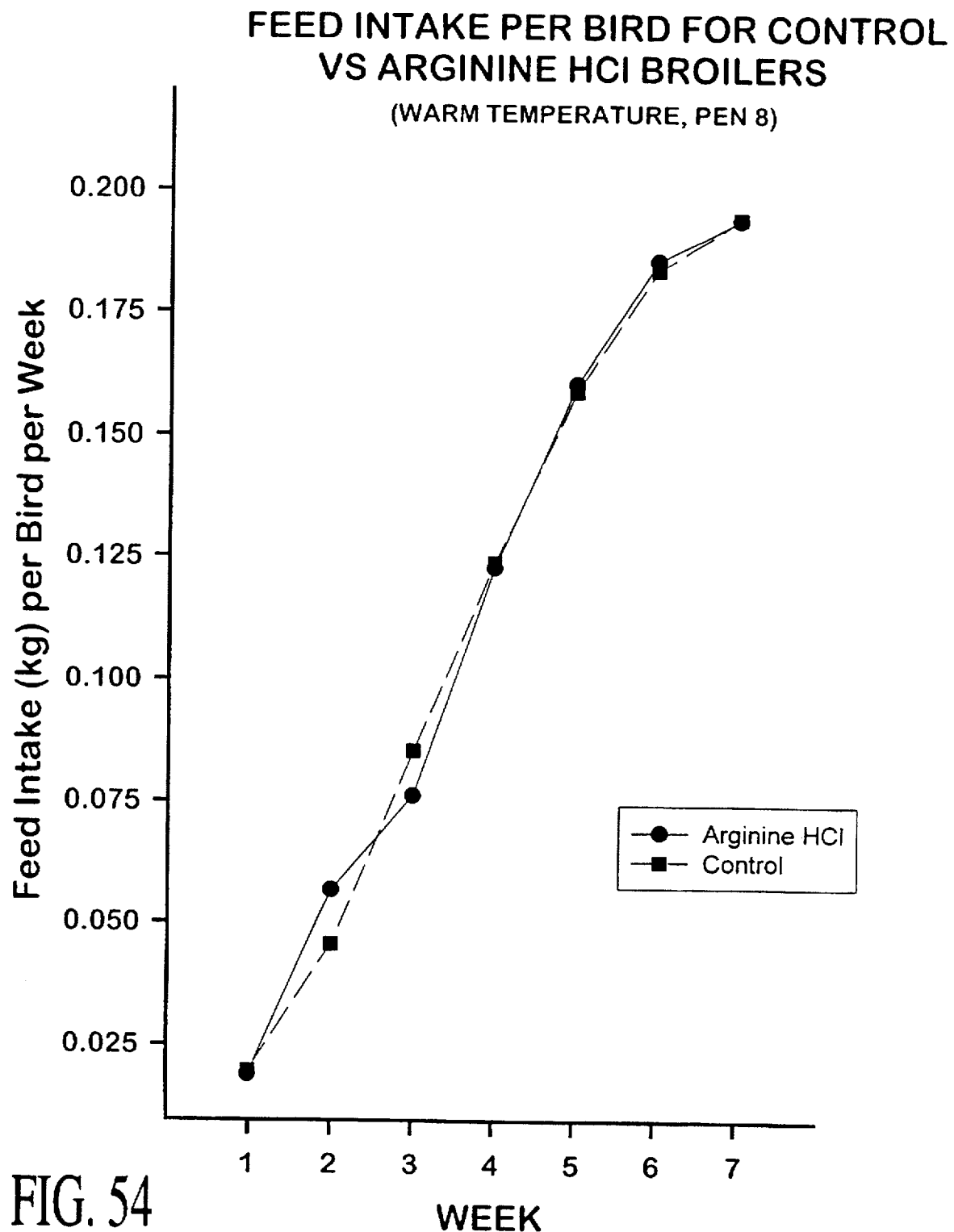
Figure 55:
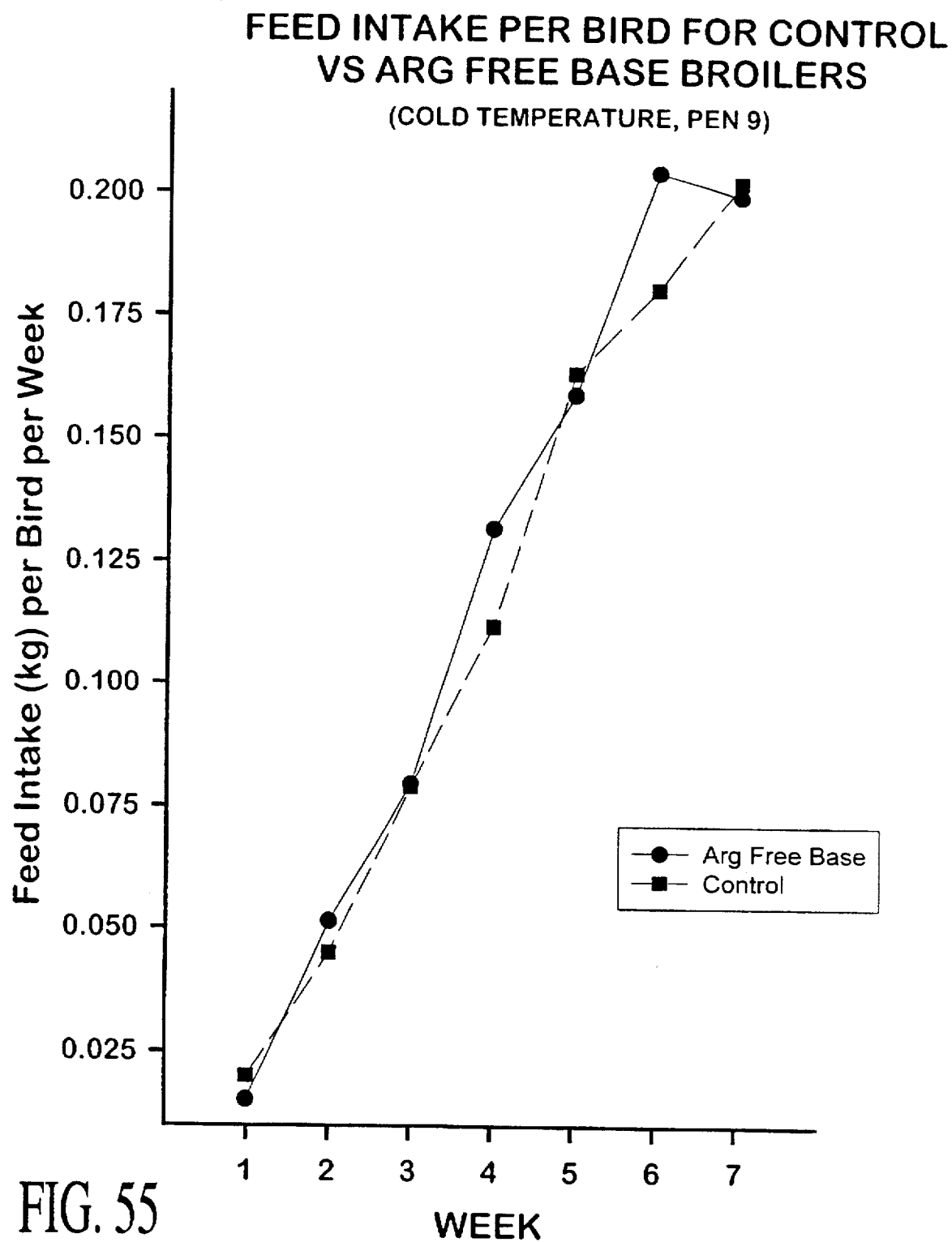
Figure 56:
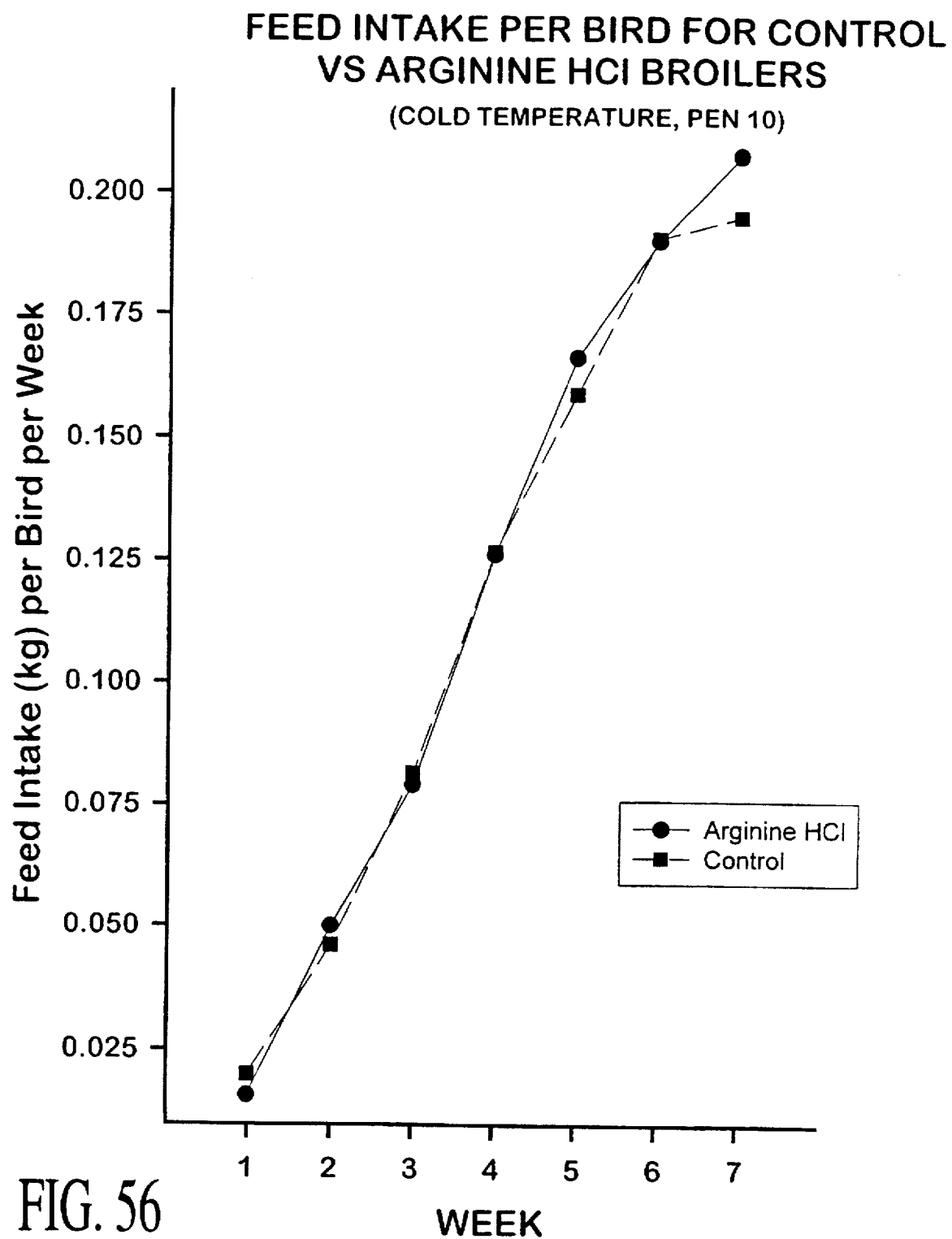
Figure 57:
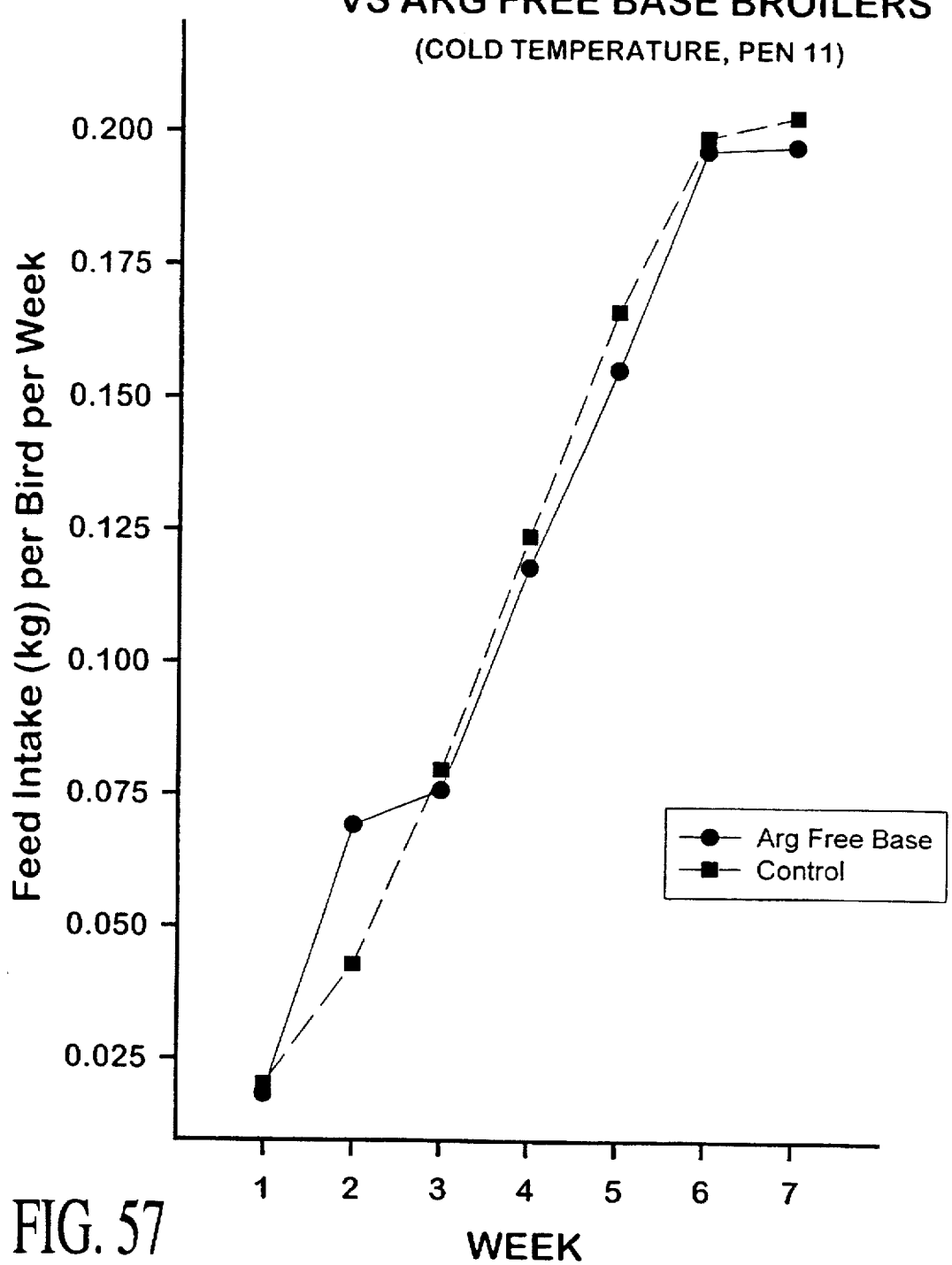
Figure 58:
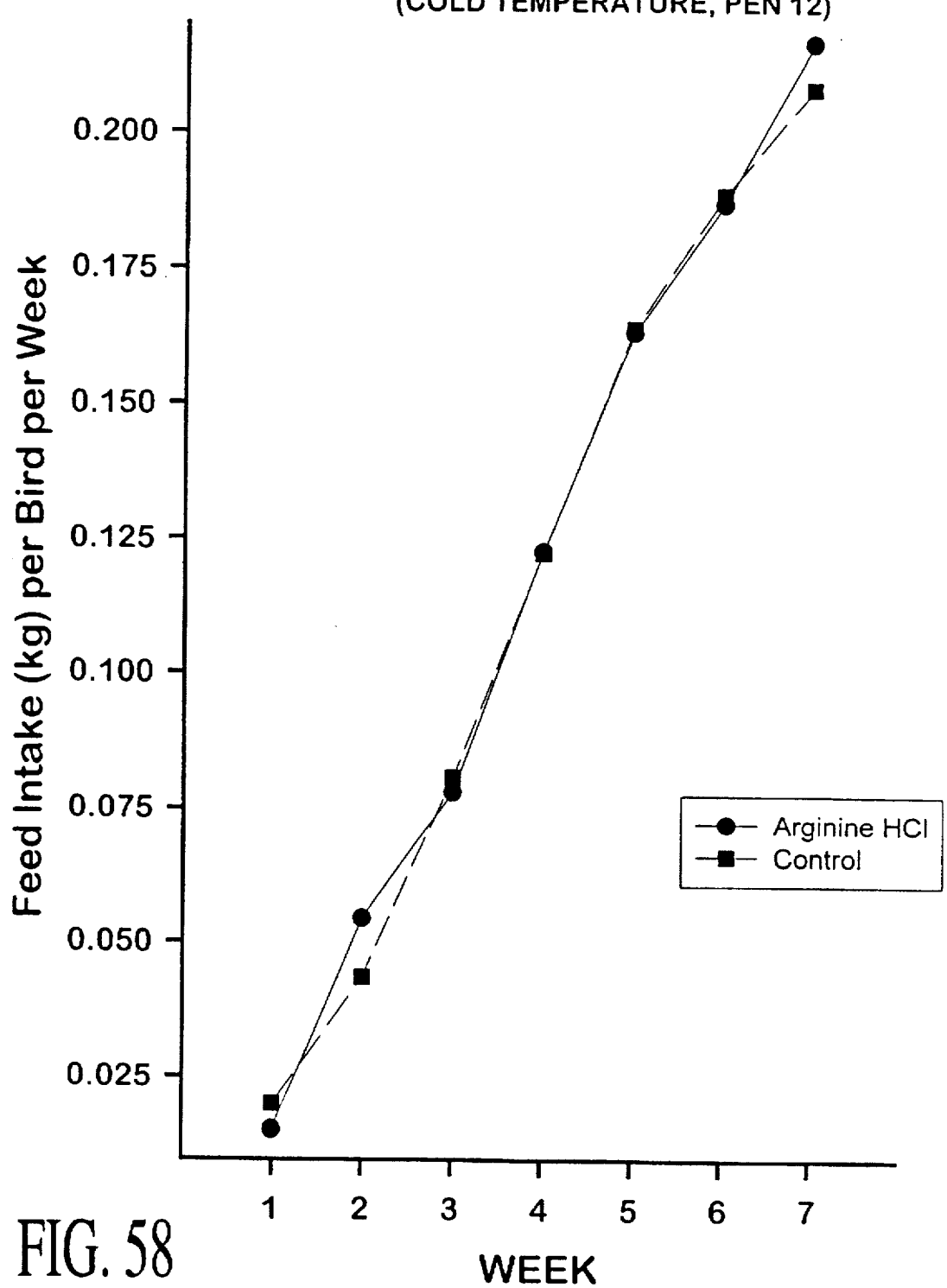
Figure 59:
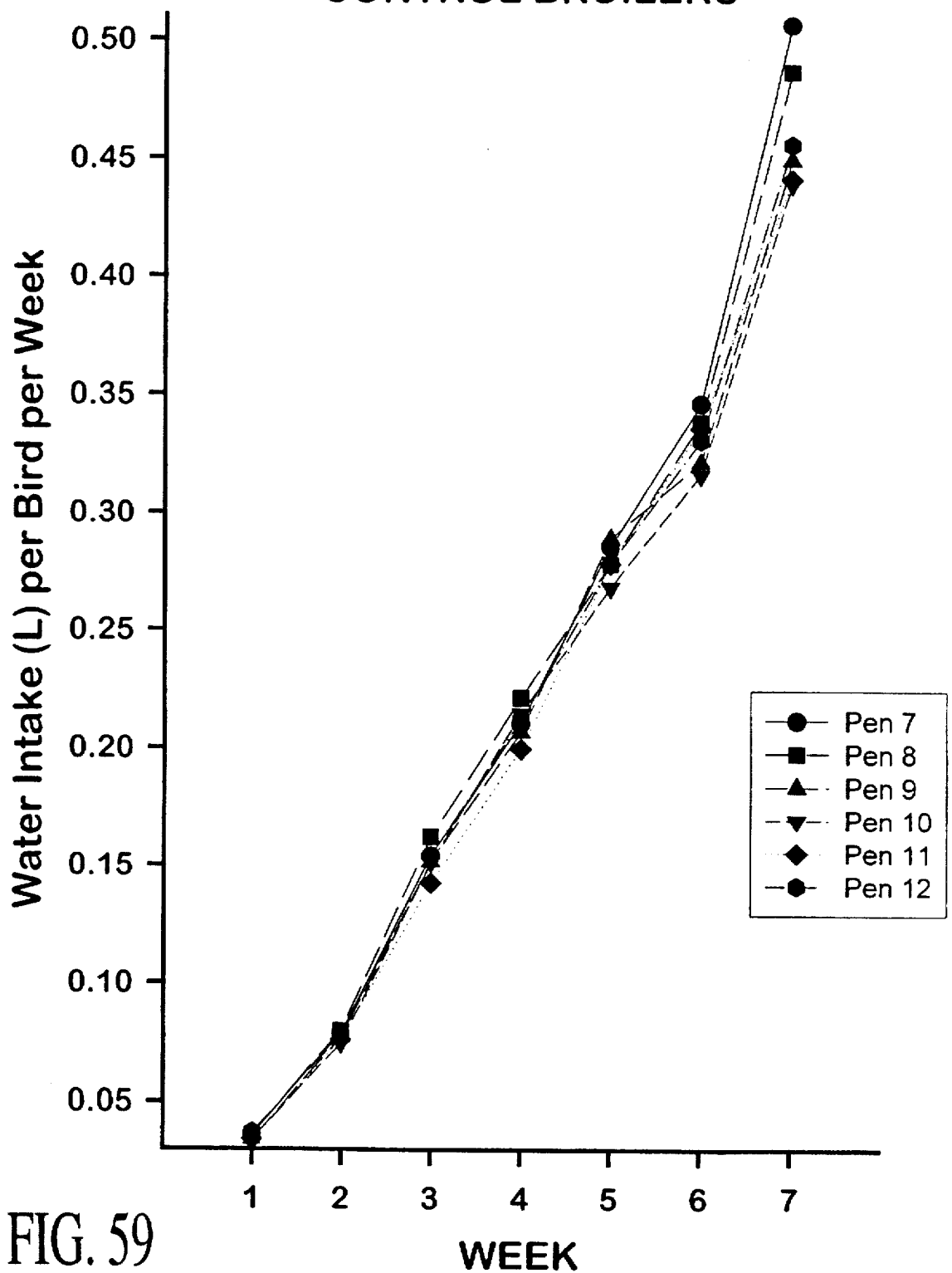
FIGS. 59–66 Water intake Curves for example 2.
Figure 60:
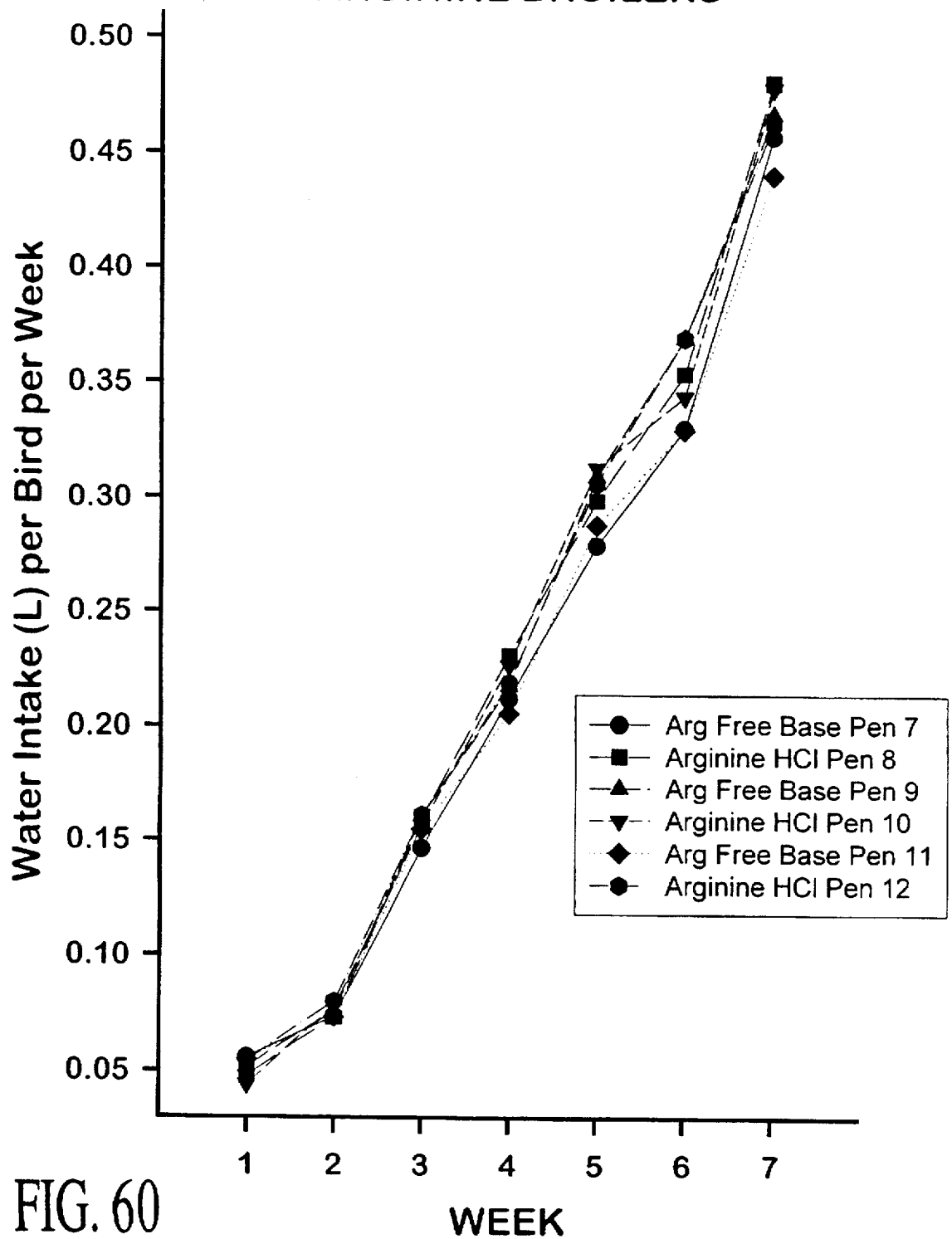
Figure 61:
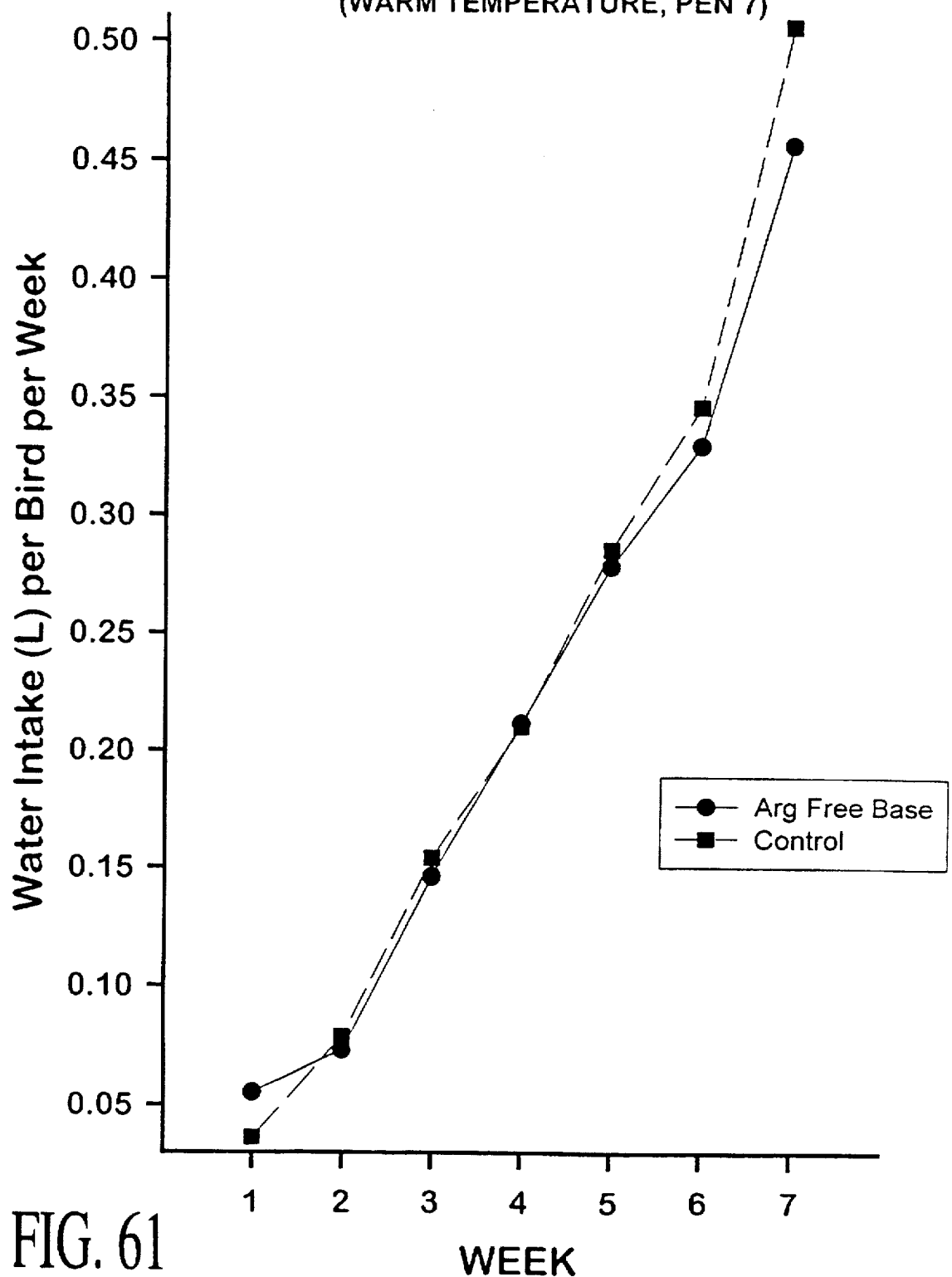
Figure 62:
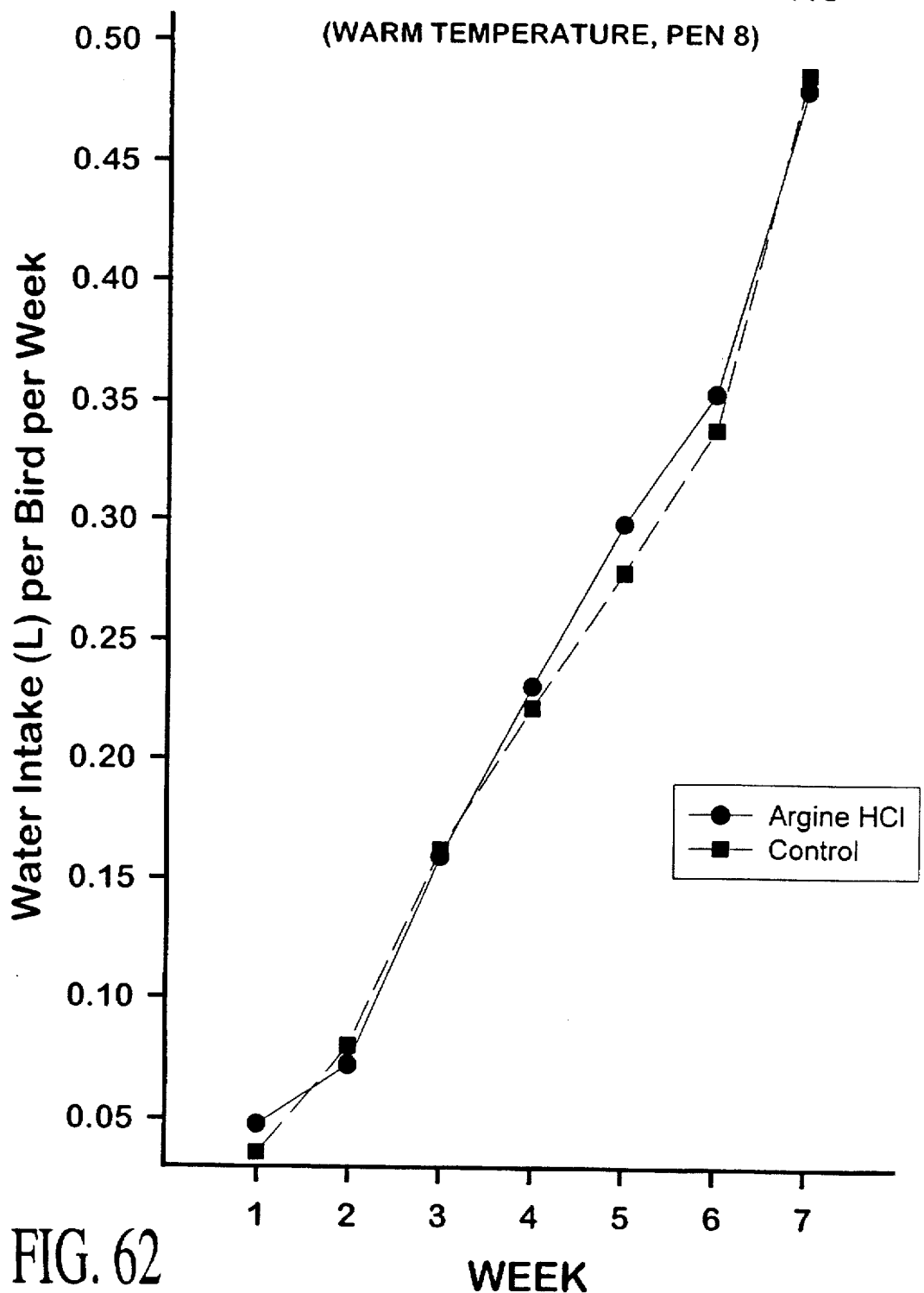
Figure 63:
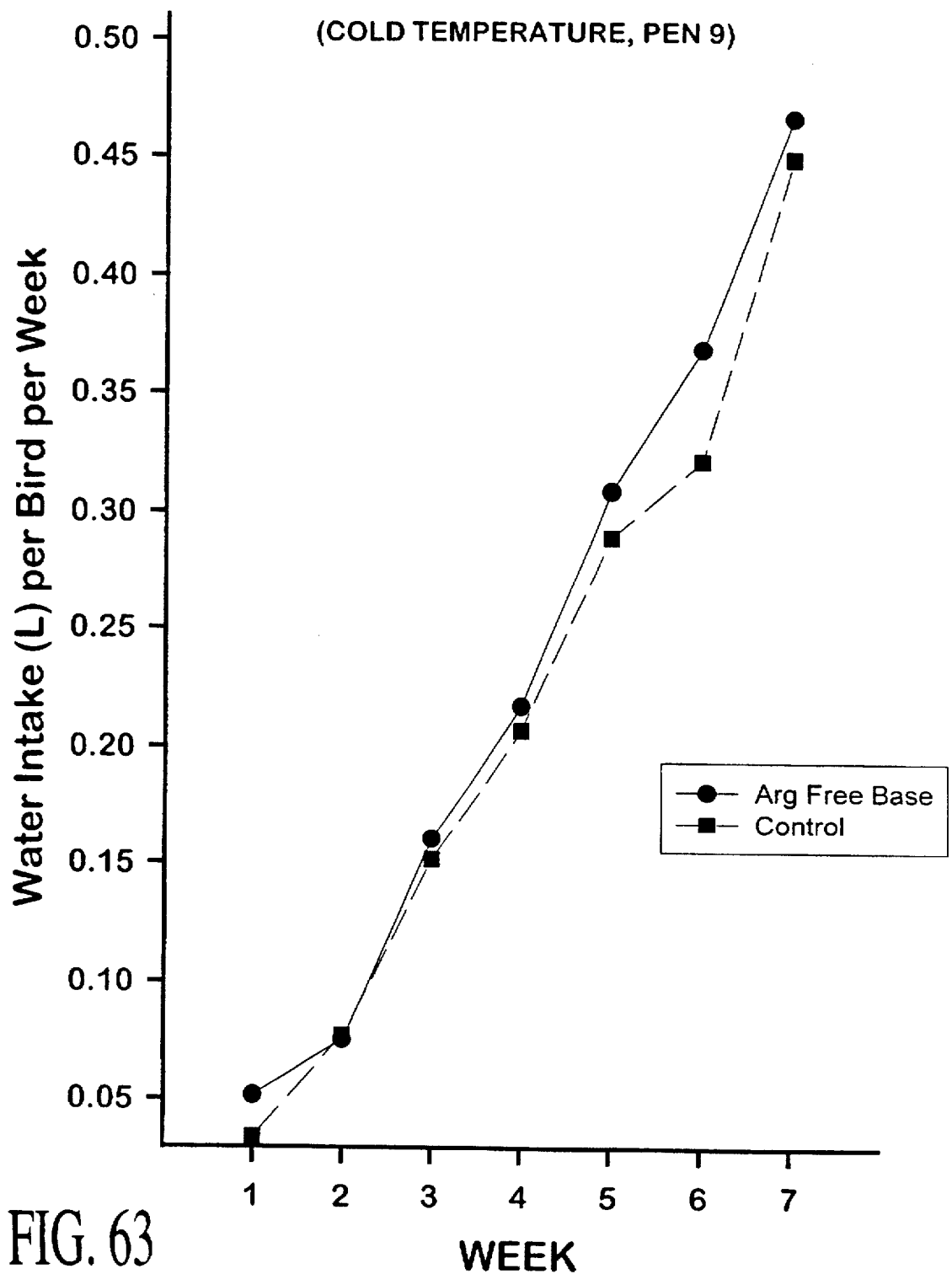
Figure 64:
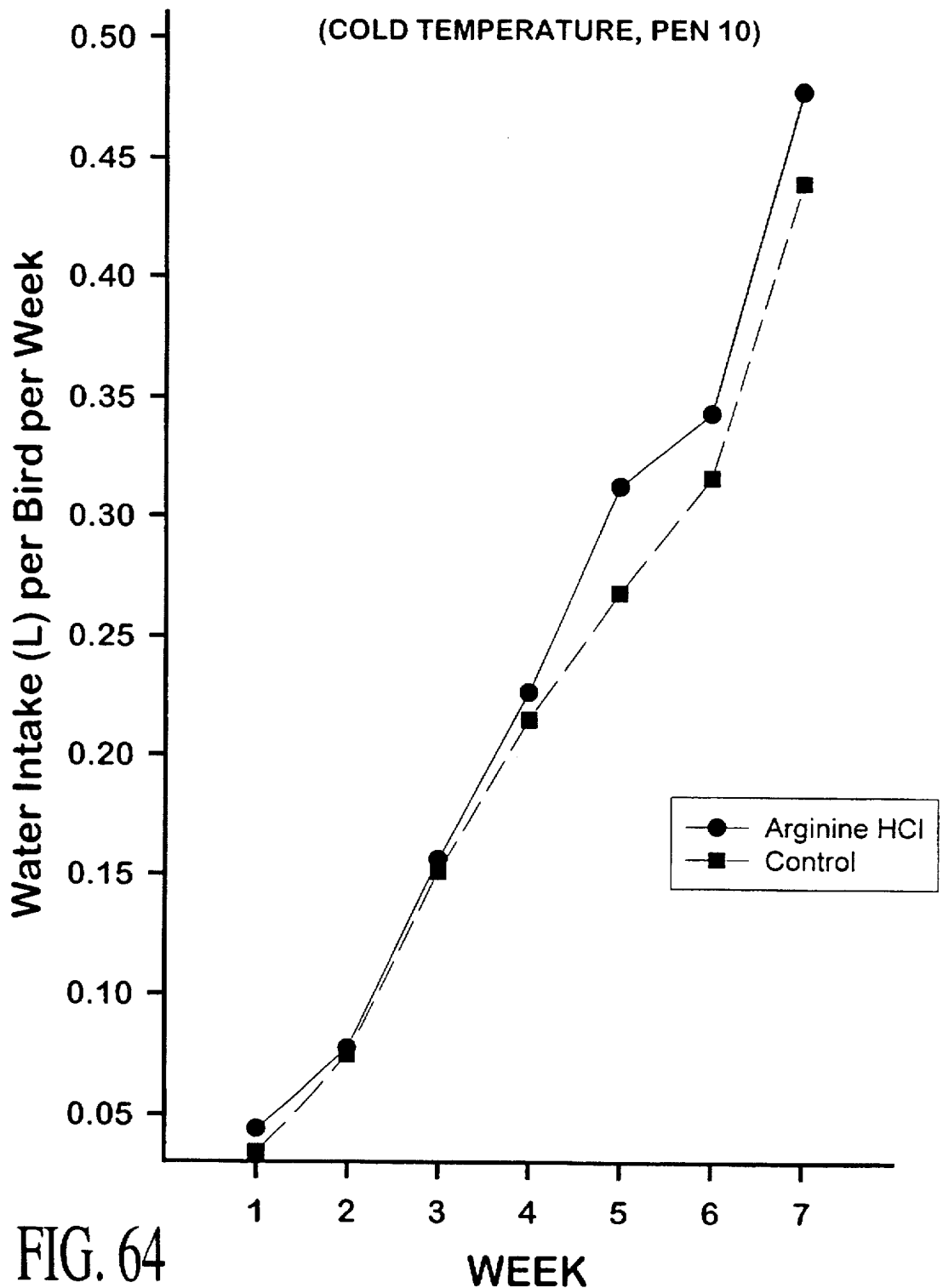
Figure 65:
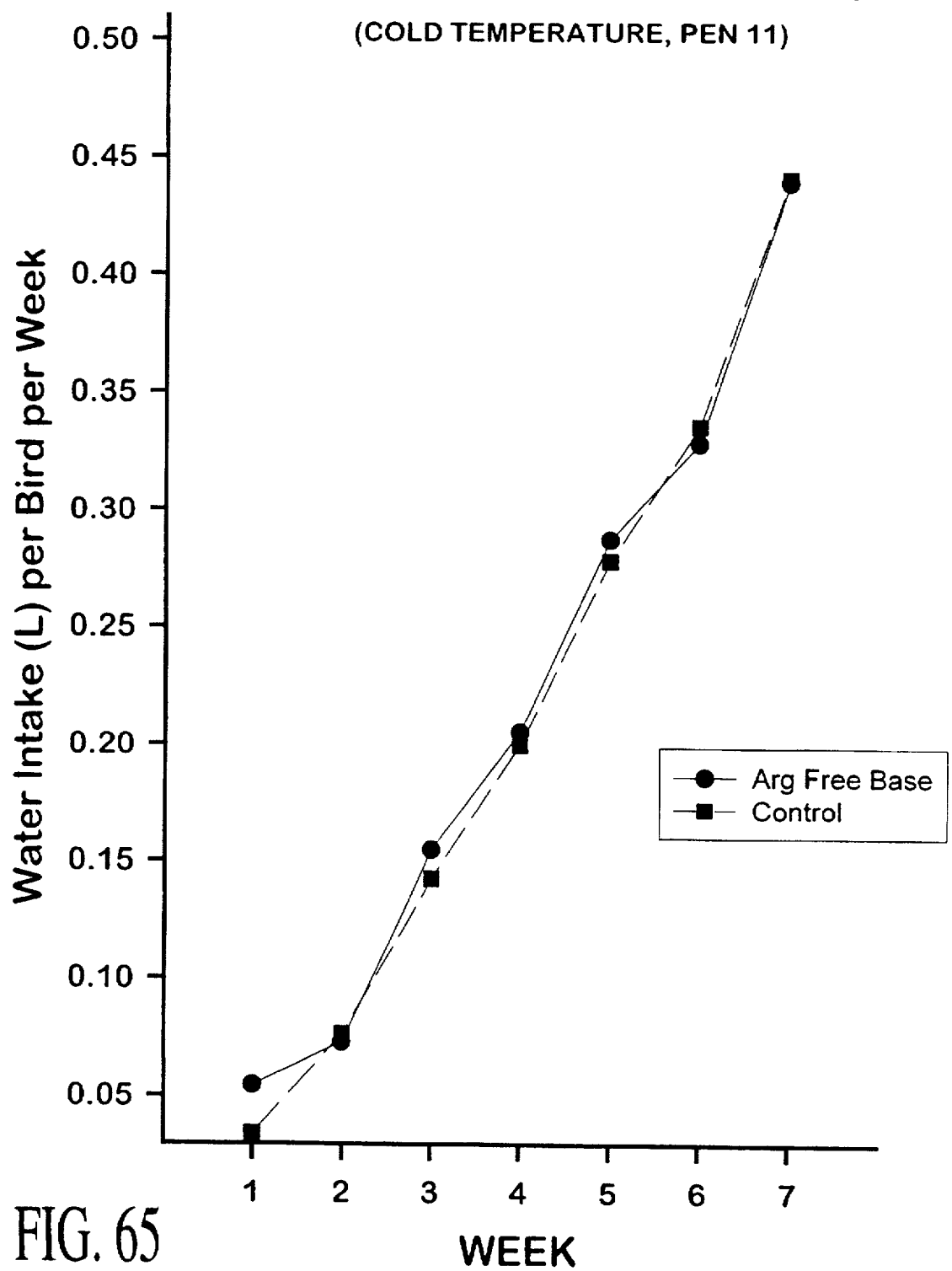
Figure 66:
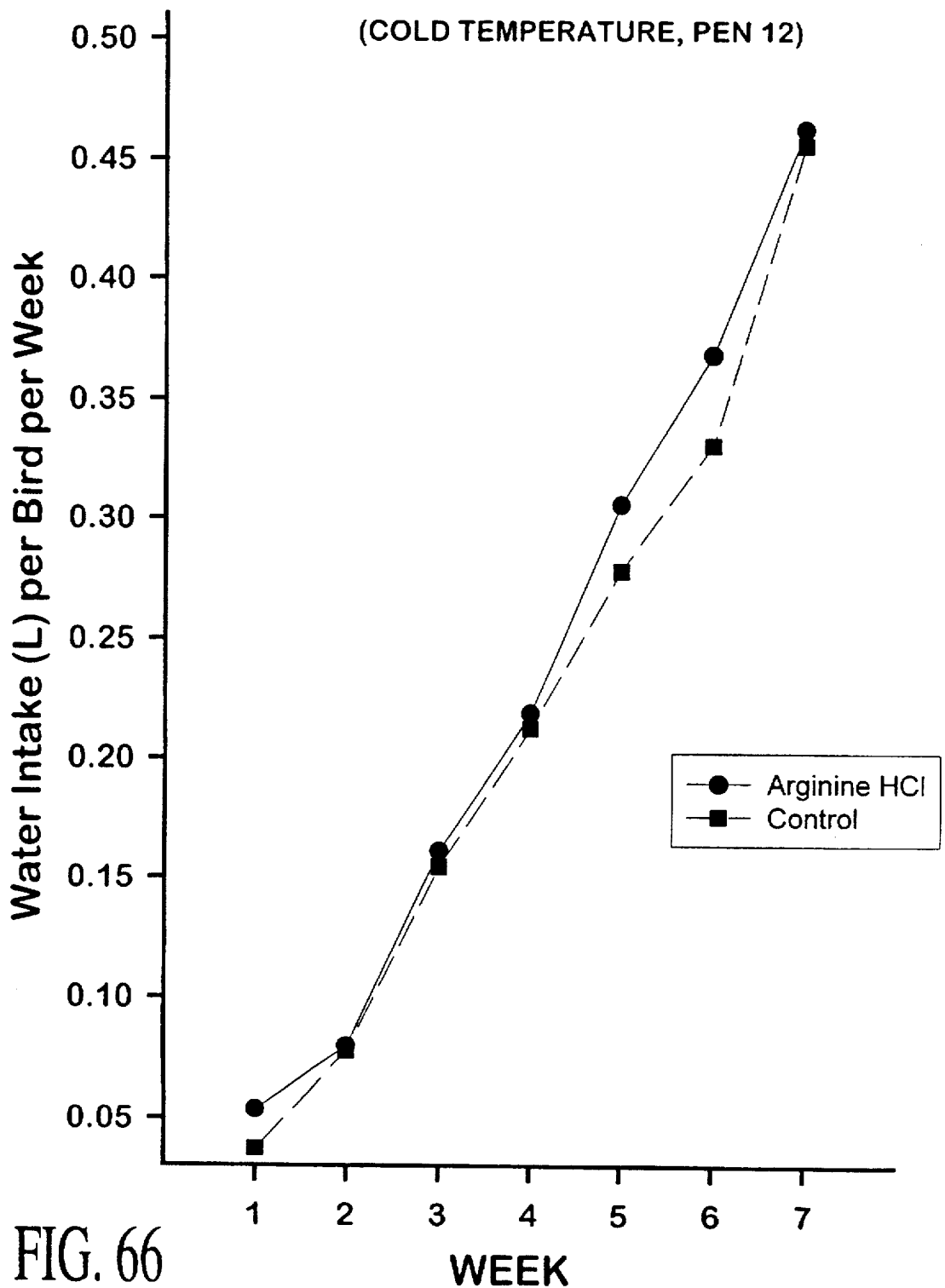

The water treatments were initiated on Day 1 and continued through Day 49. On Days 19–21, unilateral bronchus clamps were surgically implanted in 30 birds per chamber half, whereas the remaining 20 birds per chamber half were sham-operated. The birds were weighed weekly, and feed and water intake were recorded weekly. Plasma samples were collected for amino acid analysis on Days 21 and 49.
Growth Results Growth Results are summarized in FIGS. 2–17 which illustrate the effect of increasing levels of arginine on growth. The growth curves for all Sham broilers on Tap Water were virtually coincident (FIG. 2), as were the growth curves for all Bronchus Clamp broilers (FIG. 3) on Tap Water. Increasing levels of arginine in the drinking water, whether from Arginine HCl or from Arginine Free Base, caused dose-related growth depression in both the SHAM broilers and the Bronchus Clamp Broilers. Comparisons of the Tap Water vs. Arginine Water growth curves within each chamber show the high and medium levels of arginine depressed growth beginning during the first week (FIGS. 6–13, Chambers 7 to 10). However, growth was not depressed when the birds were receiving the 3.0 and 3.4 g/L level of Arginine Free Base, or the 3.6 and 4.2 g/L levels of Arginine HCl (FIGS. 14–17, Chambers 11 and 12).
Water Intake Results Water Intake Results are summarized in FIGS. 18–25 which illustrate water intake per bird. Although some variability is apparent, comparisons of Tap Water vs. Arginine Water intake within each chamber provide no consistent evidence that water intake was reduced by the arginine concentration in the drinking water. The arginine-related growth depression at high and medium levels clearly cannot be attributed to reduced water consumption. Overall trends suggest Arginine HCl triggered higher levels of water intake than Arginine Free Base.
Feed Intake Results Feed Intake Results are summarized in FIGS. 26–33 which illustrate feed intake per bird. The highest levels of Arginine HCl and Arginine Free Base in the drinking water (Chambers 7F and 8F) clearly depressed feed intake when compared with the Tap Water controls (Chambers 7R and 8R, respectively). The medium levels of arginine in the drinking water depressed feed intake marginally (Chambers 9F, 11F), whereas feed intake was not suppressed by the lowest levels of arginine in the drinking water (Chambers 10F, 12F).
Water and Plasma Arginine Values Water and Plasma Arginine Values are shown in FIGS. 34–38. FIG. 34 shows water arginine concentration compared to the target, initial and final water arginine values. FIGS. 35–36 show the plasma amino acid concentration plotted against plasma Arginine and Lysine on Day 21 and Day 49 respectively. FIG. 37 shows Plasma Arginine concentration plotted against plasma arginine on days 21 and 49. FIG. 38 shows Plasma Lysine concentration plotted against plasma lysine on days 21 and 49.

For the medium and low arginine levels in the drinking water, the assayed arginine values closely approximated the intended target arginine concentrations. Also, the medium and low levels of arginine dissolved in water appeared to be highly stable over a period of one week, under the conditions of the experiment. For the Day 21 plasma samples, the concentration of arginine in the drinking water tended to be directly correlated with plasma arginine concentrations. At each level of arginine in the drinking water. Arginine HCl tended to elevate plasma arginine more than Arginine Free base (perhaps partially reflecting the higher rate of water consumption for the arginine-HCl treatments). The lowest plasma arginine levels were obtained in groups 12R and 11R, which received tap water. At the low and medium levels of water supplementation with arginine, plasma lysine tended to increase along with plasma arginine (this does not reflect the higher feed intake observed at decreasing water arginine supplementation). At the highest level of water supplementation, the highest levels of plasma arginine were associated with the lowest levels of plasma lysine. Presumably the large elevation in plasma arginine depressed feed intake, thereby reducing plasma lysine and triggering the severe early growth depression noted in Chambers 7F and 8F. Plasma arginine concentrations generally remained constant through day 49, whereas plasma lysine concentrations decreased in all but one treatment group by Day 49. This observations suggests an age-dependent metabolic transition may occur in plasma amino acid profiles in broilers.

TABLE 1

Chamber 7F
Level 3 Arginine Free Base water treatment.

| Day of Age | Week | Grams of Arginine Free Base per 1 Liter of Water | Grams of Arginine Free Base per 5 Liters of Water | Grams of Arginine Free Base per 10 Liters of water |
|---|---|---|---|---|
| 1–7 | 1 | 12.0 | 60.0 | 120.0 |
| 8–14 | 2 | 12.0 | 60.0 | 120.0 |
| 15–21 | 3 | 13.6 | 68.0 | 136.0 |
| 22–28 | 4 | 14.0 | 70.0 | 140.0 |
| 29–35 | 5 | 15.2 | 76.0 | 152.0 |
| 36–42 | 6 | 15.2 | 76.0 | 152.0 |
| 43–49 | 7 | 15.2 | 76.0 | 152.0 |

TABLE 2

Chamber 8F
Level 3 Arginine HCl water treatment.

| Day of Age | Week | Grams of Arginine HCl per 1 Liter of Water | Grams of Arginine HCl per 5 Liters of Water | Grams of Arginine HCl per 10 Liters of Water |
|---|---|---|---|---|
| 1–7 | 1 | 14.4 | 72.0 | 144.0 |
| 8–14 | 2 | 14.4 | 72.0 | 144.0 |
| 15–21 | 3 | 16.4 | 82.0 | 164.0 |
| 22–28 | 4 | 16.8 | 84.0 | 168.0 |
| 29–35 | 5 | 18.4 | 92.0 | 184.0 |
| 36–42 | 6 | 18.4 | 92.0 | 184.0 |
| 43–49 | 7 | 18.4 | 92.0 | 184.0 |

TABLE 3

Chamber 9F
Level 2 Arginine Free Base water treatment.

| Day of Age | Week | Grams of Arginine Free Base per 1 Liter of Water | Grams of Arginine Free Base per 5 Liters of Water | Grams of Arginine Free Base per 10 Liters of water |
|---|---|---|---|---|
| 1–7 | 1 | 6.0 | 30.0 | 60.0 |
| 8–14 | 2 | 6.0 | 30.0 | 60.0 |
| 15–21 | 3 | 6.8 | 34.0 | 68.0 |
| 22–28 | 4 | 7.0 | 35.0 | 70.0 |
| 29–35 | 5 | 7.6 | 38.0 | 76.0 |

TABLE 3-continued

Chamber 9F
Level 2 Arginine Free Base water treatment.

| Day of Age | Week | Grams of Arginine Free Base per 1 Liter of Water | Grams of Arginine Free Base per 5 Liters of Water | Grams of Arginine Free Base per 10 Liters of water |
|---|---|---|---|---|
| 36–42 | 6 | 7.6 | 38.0 | 76.0 |
| 43–49 | 7 | 7.6 | 38.0 | 76.0 |

TABLE 4

Chamber 10F
Level 2 Arginine HCl water treatment.

| Day of Age | Week | Grams of Arginine HCl per 1 Liter of Water | Grams of Arginine HCl per 5 Liters of Water | Grams of Arginine HCl per 10 Liters of water |
|---|---|---|---|---|
| 1–7 | 1 | 7.2 | 36.0 | 72.0 |
| 8–14 | 2 | 7.2 | 36.0 | 72.0 |
| 15–21 | 3 | 8.2 | 41.0 | 82.0 |
| 22–28 | 4 | 8.4 | 42.0 | 84.0 |
| 29–35 | 5 | 9.2 | 46.0 | 92.0 |
| 36–42 | 6 | 9.2 | 46.0 | 92.0 |
| 43–49 | 7 | 9.2 | 46.0 | 92.0 |

TABLE 5

Chamber 11F
Level 1 Arginine Free Base water treatment.

| Day of Age | Week | Grams of Arginine Free Base per 1 Liter of Water | Grams of Arginine Free Base per 5 Liters of Water | Grams of Arginine Free Base per 10 Liters of water |
|---|---|---|---|---|
| 1–7 | 1 | 3.0 | 15.0 | 30.0 |
| 8–14 | 2 | 3.0 | 15.0 | 30.0 |
| 15–21 | 3 | 3.4 | 17.0 | 34.0 |
| 22–28 | 4 | 3.5 | 17.5 | 35.0 |
| 29–35 | 5 | 3.8 | 19.0 | 38.0 |
| 36–42 | 6 | 3.8 | 19.0 | 38.0 |
| 43–49 | 7 | 3.8 | 19.0 | 38.0 |

TABLE 6

Chamber 12F
Level 1 Arginine HCl water treatment.

| Day of Age | Week | Grams of Arginine HCl per 1 Liter of Water | Grams of Arginine HCl per 5 Liters of Water | Grams of Arginine HCl per 10 Liters of water |
|---|---|---|---|---|
| 1–7 | 1 | 3.6 | 18.0 | 36.0 |
| 8–14 | 2 | 3.6 | 18.0 | 36.0 |
| 15–21 | 3 | 4.1 | 20.5 | 41.0 |
| 22–28 | 4 | 4.2 | 21.0 | 42.0 |
| 29–35 | 5 | 4.6 | 23.0 | 46.0 |
| 36–42 | 6 | 4.6 | 23.0 | 46.0 |
| 43–49 | 7 | 4.6 | 23.0 | 46.0 |

Example 2

The Efficacy of Drinking Water Supplementation with Arginine for Preventing Ascites In Broilers.

Experimental Design

Figure 39:
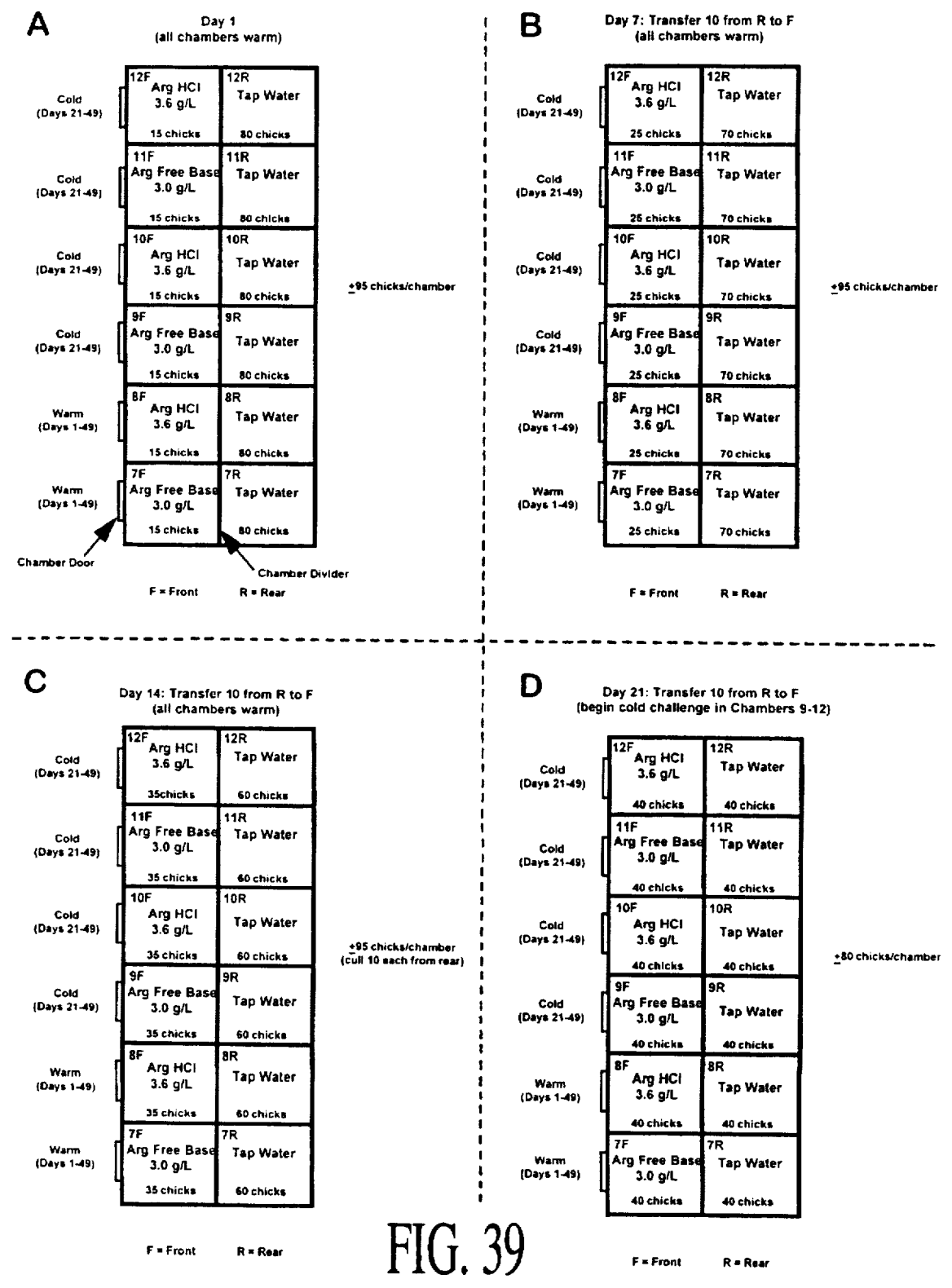

Seven hundred male byproduct chicks of the Hubbard breeder pullet line were wing banded and weighed. Obvious culls and all chicks weighing under 40 g were eliminated. The remaining chicks were distributed evenly among the environmental chambers (±90 chicks per chamber) containing fresh wood shavings litter. The experimental design is summarized in FIG. 39. FIG. 39 shows the chamber assignments on day 1, day 7, day 14 and day 21 with 7F–12F depicting the front half of each chamber, and with 7R–12R depicting the rear half of each chamber. Chamber temperatures were brought to 92° F. prior to the arrival of the chicks. The daily light/dark cycle was 24 hours L for Days 1–5, and 23 hours L/1 hour D thereafter. Each chamber was divided into two compartments, and each compartment was equipped with one Plasson-type waterer, with water supplied from a 20 Liter carboy. Tap water was provided in the rear compartments, whereas water containing either 3.0 g/L Arginine Free Base or equimolar Arg HCl (3.6 g/L) was provided in the front compartment of each chamber. These 0.3% levels of water supplementation appear to be the highest arginine concentrations that can be tolerated if growth suppression is to be minimized at normal temperatures. Given a water:feed intake ratio in normal broilers of approximately 1.8, then the 0.3% level of water supplementation would approximately equal supplementing the feed with 0.54% arginine. Water and feed were provided ad libitum. On Day 1, ten chicks were placed in the front compartment of each chamber (arginine water treatment), and eighty chicks will be placed in the rear compartment of each chamber (tap water treatment). On Days 7, 14, and 21, ten chicks were transferred from the rear to the front of each chamber, providing different ages of exposure as well as different durations of exposure to the supplemental arginine. As shown in FIG. 1, each compartment held 40 chicks at the start of the cold challenge on Day 21. Chamber temperatures were 92° F. for Days 1–5, 85° F. for Days 6–10, 80° F. for Days 11–14, and 75° F. for Days 15–21. Thereafter through Day 49, chamber temperatures were maintained at 75° F. in Chambers 7 and 8, and at 60 to 65° F. in Chambers 9 to 12. A 23% crude protein, 3,000 kcal/kg ME broiler "starter diet" was provided for the seven week duration of the experiment. Body weights were recorded weekly. Cumulative feed and water intake per chamber compartment were recorded. Plasma samples for amino acid profile analysis were collected from six broilers per compartment on Days 28 and 49. All birds that died after day 21 were necropsied, a diagnosis of ascites (presence of abdominal fluid) or non-ascites (all other causes) was made, and body weights and ventricular weights will be recorded. All survivors on day 49 were similarly evaluated.

Growth Results

Growth Results are summarized in FIGS. 40–50 which plot body weight against age for each group of broilers. The growth curves for broilers receiving unsupplemented water (Control) or arginine-supplemented water (Arginine HCl, Arg Free Base) were virtually coincident, revealing no evidence of arginine related growth suppression.

Feed and Water Intake Results

Feed and Water Intake Results are summarized in FIGS. 51–66. FIGS. 51–58 plot feed intake against age for each group of broilers and FIGS. 59–66 plot water intake against age for each group of broilers. Supplementing the drinking water with arginine HCl or arginine free base did not alter feed and water intake when compared with control broilers receiving tap water.

Ascites Mortality

The incidence of ascites was 9.1% (20 of 219 broilers affected) for control broilers supplied with unsupplemented water. Supplementing the water with arginine free base reduced the incidence of ascites to 6.2% (7 of 113 broilers affected), whereas supplementing the water with arginine HCl reduced the incidence of ascites to 3.5% (4 of 115 broilers affected).

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which this invention pertains.

I claim:

1. A method of treating pulmonary hypertension syndrome in an avian, comprising administering to the avian having pulmonary hypertension syndrome, drinking water comprising a sufficient amount of an L-arginine compound to treat pulmonary hypertension syndrome.

2. The method of claim 1 wherein the drinking water comprises at least about 0.01 weight percent L-arginine compound.

3. The method of claim 1 wherein the drinking water comprises at least about 0.1 weight percent L-arginine compound.

4. The method of claim 1 wherein the drinking water comprises at least about 0.25 weight percent L-arginine compound.

5. The method of claim 1 wherein the drinking water comprises at least about 0.5 weight percent L-arginine compound.

6. The method of claim 1 wherein the drinking water comprises at least about 1.0 weight percent L-arginine compound.

7. The method of claim 1 wherein the concentration of L-arginine compound in the drinking water decreases with the increasing age of the avian.

8. The method of claim 1 wherein the L-arginine compound comprises at least one selected from the group consisting of L-arginine, substituted L-arginine and L-arginine salts.

9. The method of claim 8 wherein anions for salts of L-arginine are selected from the group of anions consisting of bromide, fluoride, iodide, borate, hypobromite, hypochlorite, nitrite, nitrate, hyponitrite, sulfate, disulfate, sulfite, sulfonate, phosphate, diphosphate, phosphite, phosphonate, diphosphonate, perchlorate, perchlorite, oxalate, malonate, succinate, lactate, carbonate, bicarbonate, acetate, benzoate, citrate, tosylate, permanganate, manganate, propanolate, propanoate, ethandioate, butanoate, propoxide, chromate, dichromate, selenate, orthosilicate, metasilicate, pertechnetate, technetate, dimethanolate, dimethoxide, thiocyanate, cyanate, isocyanate, and wherein the cations for the salts of L-arginine are selected from the group of cations consisting of hydrogen, sodium, and potassium.

10. The method of claim 1 wherein the administration of the L-arginine compound commences before the avian is five weeks old.

11. The method of claim 1 wherein the administration of the L-arginine compound commences before the avian is three weeks old.

11

12. The method of claim 11 wherein the avian is a chicken, wherein the L-arginine compound comprises L-arginine free base, wherein the L-arginine free base is incorporated into and comprises greater than about 0.25 wt % of the drinking water.

13. A method of treating pulmonary hypertension syndrome in a chicken, comprising orally administering to the chicken having pulmonary hypertension syndrome a drinking water comprising a sufficient amount of an L-arginine compound to treat the pulmonary hypertension syndrome, wherein the administration of the L-arginine compound commences before the avian is five weeks old.

14. The method of claims 13 wherein the administration of the L-arginine compound commences before the avian is three weeks old.

15. The method of claim 14 wherein the L-arginine compound comprises L-arginine free base.

12

16. A method of treating avians comprising:
    (a) monitoring the avians for pulmonary hypertension syndrome or conditions known to cause pulmonary hypertension syndrome;
    (b) administering a drinking water comprising a sufficient amount of an L-arginine compound to treat pulmonary hypertension syndrome to the avians once monitoring of step (a) indicates presence of pulmonary hypertension syndrome or conditions known to cause pulmonary hypertension syndrome.

17. The method of claim 16 wherein the conditions known to cause pulmonary hypertension syndrome comprise any one of temperatures below the avian's thermoneutral zone, poor ventilation, presence of agents of respiratory distress, and high salt foods.

* * * * *